US006552181B1

(12) United States Patent
Dean et al.

(10) Patent No.: US 6,552,181 B1
(45) Date of Patent: Apr. 22, 2003

(54) BASAL CELL CARCINOMA TUMOR SUPRESSOR GENE

(75) Inventors: Michael Carlton Dean, Frederick, MD (US); Heidi Eve Hahn, Washington, DC (US); Carol Wicking, Auchenflower (AU); Jeffrey Christiansen, Yeronga (AU); Peter G Zaphiropoulos, Tullinge (SE); Mae R. Gailani, Guilford, CT (US); Susan Mary Shanley, Norman Park (AU); Abirami Chidambaram, Frederick, MD (US); Igor Vorechovsky, Huddinge (SE); Erika Holmberg-Lindstrom, Solna (SE); Anne Birgitte Unden, Huddinge (SE); Susan Alana Gillies, Newfarm (AU); Kylie Negus, Queenslopes (AU); Ian Mcleod Smyth, Fig Tree Pocket (AU); Carol Leah Pressman, Houston, TX (US); David J. Leffell, New Haven, CT (US); Bernard Gerrard, Frederick, MD (US); Alisa Miriam Goldstein, Rockville, MD (US); Brandon Wainwright, Bardon (AU); Rune Carl-Magnus Toftgard, Skarholmen (SE); Georgia Chenevix-Trench, Toowong (AU); Allen E. Bale, Northford, CT (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/857,636

(22) Filed: May 16, 1997

Related U.S. Application Data
(60) Provisional application No. 60/017,906, filed on May 17, 1996, and provisional application No. 60/019,765, filed on Jun. 14, 1996.

(51) Int. Cl.[7] .............................................. C07H 21/04
(52) U.S. Cl. ................. 536/24.31; 536/23.5; 435/320.1
(58) Field of Search ........................... 536/23.5, 24.31; 435/69.1, 172.3, 320.1, 6; 530/350, 828; 935/9

(56) References Cited

U.S. PATENT DOCUMENTS 5,837,538 A * 11/1998 Scott et al. ................. 536/23.5

FOREIGN PATENT DOCUMENTS

WO        WO96/11260          4/1996

OTHER PUBLICATIONS

Anderson et al. "The Nevoid Basal Cell Carcinoma Syndrome" (1967) *Am. J. Hum. Genet.* 19:12–22.

Bale et al. "Relationship Between Head Circumference and Height in Normal Adults and in the Nevoid Basal Cell Carcinoma Syndrome and Neurofibromatosis Type I" (1991) *Am. J. Med. Genet.* 40:206–210.

Basler and Struhl "Compartment boundaries and the control of Drosophila limb pattern by hedgehog protein" (1994) *Nature* 368:208–214.

Bonifas et al. "Parental origin of chromosome 9q22.3—q31 lost in basal cell carcinomas from basal cell nevus syndrome patients" (1994) *Hum. Mol. Genet.* 3:447–448.

Capdevila et al. "Subcellular localization of the segment polarity protein patched suggests an interaction with the wingless reception complex in Drosophila embyros" (1994) *Development* 120:987–998.

Capdevila et al. "The Drosophila segment polarity gene patched interacts with decapentaplegic in wing development" (1994) *EMBO J.* 13:71–82.

Echelard et al. "Sonic Hedgehog, a Member of a Family of Putative Signaling Molecules, Is Implicated in the Regulation of CNS Polarity" *Cell* 75:1417–1430.

Evans et al. "The incidence of Gorlin syndrome in 173 consecutive cases of medulloblastoma" (1991) *British J. Cancer* 64:959–961.

Evans et al. "Complications of the naevoid basal cell carcinoma syndrome: results of a population based study" (1993) *J. Med. Genet.* 30:460–464.

Farndon et al. "Location of gene for Gorlin syndrome" (1992) *Lancet* 339:581–582.

Farndon et al. "Analysis of 133 Meioses Places the Genes for Nevoid Basal Cell Carcinoma (Gorlin) Syndrome and Fanconi Anemia Group C in a 2.6–cM Interval and Contributes to the Fine Map of 9q22.3" (1994) *Genomics* 23:486–489.

Gailani et al. "Development Defects in Gorlin Syndrome Related to a Putative Tumor Suppressor Gene in Chromosome 9" (1992) *Cell* 69:111–117.

Gailani et al. "Relationship Between Sunlight Exposure and a Key Genetic Alteration in Basal Cell Carcinoma" (1996) *J. Natl. Canc. Inst.* 88:349–354.

Gayther et al. "Germline mutations of the BRCA1 gene in breast and ovarian cancer families provide evidence for a genotype–phenotype correlation" (1995) *Nature Genetics* 11:428–433.

Goldstein et al. "Localization of the Gene for the Nevoid Basal Cell Carcinoma Syndrome" (1994) *Am. J. Hum. Genet.* 54:765–773.

(List continued on next page.)

Primary Examiner—Lorraine Spector
(74) Attorney, Agent, or Firm—Townsend and Townsend and Crew, LLP

(57) ABSTRACT

This invention provides for a tumor suppressor gene inactivation of which is a causal factor in nevoid basal cell carcinoma syndrome and various sporadic basal cell carcinomas. The NBCCS gene is a homologue of the *Drosophila patched* (ptc) gene.

21 Claims, 22 Drawing Sheets

OTHER PUBLICATIONS

Goodrich et al. "Conservation of the hedgehog/patched signaling pathway from flies to mice: induction of a mouse patched gene by Hedgehog" (1996) *Genes & Dev.* 10:301–312.

Gorlin "Nevoid Basal–Cell Carcinoma Syndrome" (1987) *Medicine (Baltimore)* 66:98–113.

Gorlin "Nevoid Basal Cell Carcinoma Syndrome" (1995) *Dermatologic Clinics* 13:113–125.

Gutierrez and Mora "Nevoid basal cell carcinoma syndrome" (1986) *J. Am. Acad. Dermatol.* 15:1023–1029.

Hahn et al. "A Mammalian patched Homolog Is Expressed in Target Tissues of *Sonic hedgehog* and Maps to a Region Associated with Development Abnormalities" (1996) *J. Biol. Chem.* 271(12):12125–12128.

Hahn et al. "DPC4, A Candidate Tumor Suppressor Gene at Human Chromosome 18q21.1" (1996) *Science* 271:350–353.

Harshman et al. "Comparison of the positional cloning methods used to isolate the BRCA1 gene" (1995) *Hum. Mol. Genet.* 4:1259–1266.

Hooper et al. "The Drosophila patched Gene Encodes a Putative Membrane Protein Required for Segmental Patterning" (1989) *Cell* 59:751–765.

Ingham et al. "Role of the *Drosophila patched* gene in positional signalling" (1991) *Nature* 353:184–187.

Ingham "Signalling by hedgehog family proteins in Drosophila and vertebrate development" (1995) *Curr. Opinion Genet. Develop.* 5:492–498.

Jessell et al. "Floor Plate–Derived Signals and The Control of Neural Cell Pattern in Vertebrates" (1990) *Harvey Lect.*, 86:87–128.

Johnson et al. "Ectopic Expression of *Sonic hedgehog* Alters Dorsal–Ventral Patterning of Somites" (1994) *Cell* 79:1165–1173.

Knowles "Molecular genetics of bladder cancer" (1995) *Br. J. Urol.* 75:57–66.

Kozak "Structural Features in Eukaryotic mRNAs that Modulate the Initiation of Translation" *J. Biol. Chem.* 266:19867–19870.

Levanat et al. "A two–hit model for development defects in Gorlin syndrome" (1996) *Nat. Genetics* 12:85–87.

Miller "Biology of basal cell carcinoma (Part III)" (1991) *J. Am. Acad. Dermatol.* 24:161–175.

Nakano et al. "A protein with several possible membrane–spanning domains encoded by the Drosophila segment polarity gene patched" (1989) *Nature* 341:508–513.

Nusslein–Volhard et al. "Mutations affecting segment number and polarity of Drosophila" (1980) *Nature* 287:795–801.

Pericak–Vance "Report on the Fourth International Workshop on Chromosome 9" (1995) *Ann. Hum. Genet.* 59:347–365.

Phillips et al. "The Drosophila segment polarity gene patched is involved in a position–signalling mechanism in imaginal discs" (1990) *Development* 110:105–114.

Pourquie et al. "Control of dorsoventral patterning of somitic derivatives by notochord and floor plate" (1993) *Proc. Natl. Acad. Sci. USA* 90:5242–5246.

Reis et al. "Localisation of gene for the naevoid basal–cell carcinoma syndrome" (1992) *Lancet* 339:617.

Riddle et al. "*Sonic hedgehog* Mediates the Polarizing Activity of the ZPA" (1993) *Cell* 75:1401–1416.

Roelink et al. "Floor Plate and Motor Neuron Induction by Different Concentrations of the Amino–Terminal Cleavage Product of *Sonic hedgehog* Autoproteolysis" (1995) *Cell* 81:445–455.

Roelink et al. "Floor Plate and Motor Neuron Induction by vhh–1, a Vertebrate Homolog of hedgehog Expressed by the Notochord" (1994) *Cell* 76:761–775.

Shanley et al. "Nevoid Basal Cell Carcinoma Syndrome: Review of 118 Affected Individuals" (1994) *Am. J. Med. Genet.* 50:282–290.

Shanley et al. "Fine deletion mapping on the long arm of chromosome 9 in sporadic and familial basal cell carcinomas" (1995) *Hum. Mol. Genet.* 4:129–133.

Springate "The Nevoid Basal Cell Carcinoma Syndrome" (1986) *J. Pediatr. Surg.* 21:908–910.

Strathdee et al. "Cloning of cNDAs for Fanconi's anaemia by functional complementation" (1992) *Nature* 356:763–767.

Tabata and Kornberg "Hedgehog is a Singalling Protein with a Key Role in Patterning Drosophila Imaginal Discs" (1994) *Cell* 76:89–102.

Vaahtokari et al. "The enamel knot as a signaling center in the developing mouse tooth" (1996) *MOD* 54:39–43.

Wicking et al. "Fine Genetic Mapping of the Gene for Nevoid Basal Cell Carcinoma Syndrome" (1994) *Genomics* 22:505–511.

\* cited by examiner

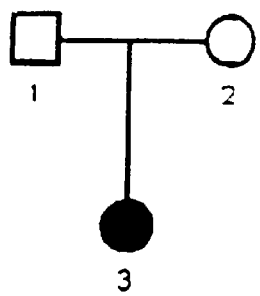
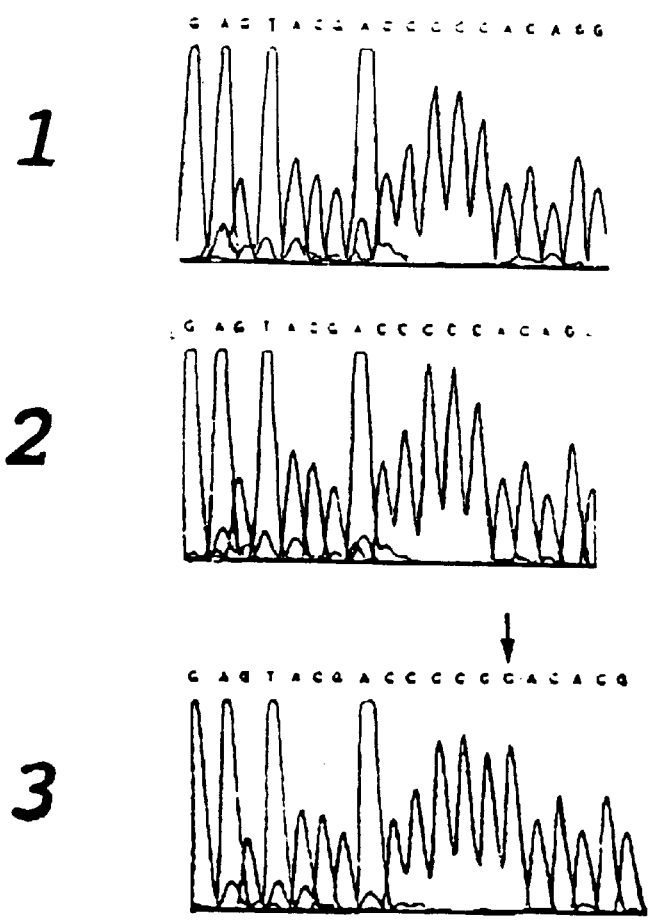
Figure 5

```
GAAGGCGAGC ACCCAGACGG GGGCCCGCCG GGGTCGCGGC CAGCGCCGGG GAAATGCCGC         60

GCCGGGGAGC AGCATGCGCC GGCCTGAGCC CTTCCCTTTG CACTCGGCTG TTTTTTACGT        120

TTAACCAGAA AGGAAGGGAG AGGAGGGAAA GATCCATGTG GCTGCCCTCT TCCGATCACA        180

AATATTGTCG GGAAGGCTAC TGGCCGGAAA GCGCCGCTGT GGCTGAGAGC GAAGTTTCAG        240

AGACTCTTAT TTAAACTGGG TTGTTACATT CAAAAAAACT GCGGCAAGTT CTTGGTTGTG        300

GGCCTCCTCA TATTTGGGGC CTTCGCGGTG GGATTAAAAG CAGCGAACCT CGAGACCAAC        360

GTGGAGGAGC TGTGGGTGGA AGTTGGAGGA CGAGTAAGTC GTGAATTAAA TTATACTCGC        420

CAGAAGATTG GAGAAGAGGC T ATG TTT AAT CCT CAA CTC ATG ATA CAG ACC         471
                        Met Phe Asn Pro Gln Leu Met Ile Gln Thr
                         1                5                  10

CCT AAA GAA GAA GGT GCT AAT GTC CTG ACC ACA GAA GCG CTC CTA CAA         519
Pro Lys Glu Glu Gly Ala Asn Val Leu Thr Thr Glu Ala Leu Leu Gln
            15                  20                  25

CAC CTG GAC TCG GCA CTC CAG GCC AGC CGT GTC CAT GTA TAC ATG TAC         567
His Leu Asp Ser Ala Leu Gln Ala Ser Arg Val His Val Tyr Met Tyr
        30                  35                  40

AAC AGG CAG TGG AAA TTG GAA CAT TTG TGT TAC AAA TCA GGA GAG CTT         615
Asn Arg Gln Trp Lys Leu Glu His Leu Cys Tyr Lys Ser Gly Glu Leu
    45                  50                  55

ATC ACA GAA ACA GGT TAC ATG GAT CAG ATA ATA GAA TAT CTT TAC CCT         663
Ile Thr Glu Thr Gly Tyr Met Asp Gln Ile Ile Glu Tyr Leu Tyr Pro
60                  65                  70

TGT TTG ATT ATT ACA CCT TTG GAC TGC TTC TGG GAA GGG GCG AAA TTA         711
Cys Leu Ile Ile Thr Pro Leu Asp Cys Phe Trp Glu Gly Ala Lys Leu
75                  80                  85                  90

CAG TCT GGG ACA GCA TAC CTC CTA GGT AAA CCT CCT TTG CGG TGG ACA         759
Gln Ser Gly Thr Ala Tyr Leu Leu Gly Lys Pro Pro Leu Arg Trp Thr
                95                  100                 105

AAC TTC GAC CCT TTG GAA TTC CTG GAA GAG TTA AAG AAA ATA AAC TAT         807
Asn Phe Asp Pro Leu Glu Phe Leu Glu Glu Leu Lys Lys Ile Asn Tyr
            110                 115                 120
```

FIG. 8-1

```
CAA GTG GAC AGC TGG GAG GAA ATG CTG AAT AAG GCT GAG GTT GGT CAT      855
Gln Val Asp Ser Trp Glu Glu Met Leu Asn Lys Ala Glu Val Gly His
        125                 130                 135

GGT TAC ATG GAC CGC CCC TGC CTC AAT CCG GCC GAT CCA GAC TGC CCC      903
Gly Tyr Met Asp Arg Pro Cys Leu Asn Pro Ala Asp Pro Asp Cys Pro
        140                 145                 150

GCC ACA GCC CCC AAC AAA AAT TCA ACC AAA CCT CTT GAT ATG GCC CTT      951
Ala Thr Ala Pro Asn Lys Asn Ser Thr Lys Pro Leu Asp Met Ala Leu
155                 160                 165                 170

GTT TTG AAT GGT GGA TGT CAT GGC TTA TCC AGA AAG TAT ATG CAC TGG      999
Val Leu Asn Gly Gly Cys His Gly Leu Ser Arg Lys Tyr Met His Trp
                175                 180                 185

CAG GAG GAG TTG ATT GTG GGT GGC ACA GTC AAG AAC AGC ACT GGA AAA     1047
Gln Glu Glu Leu Ile Val Gly Gly Thr Val Lys Asn Ser Thr Gly Lys
            190                 195                 200

CTC GTC AGC GCC CAT GCC CTG CAG ACC ATG TTC CAG TTA ATG ACT CCC     1095
Leu Val Ser Ala His Ala Leu Gln Thr Met Phe Gln Leu Met Thr Pro
            205                 210                 215

AAG CAA ATG TAC GAG CAC TTC AAG GGG TAC GAG TAT GTC TCA CAC ATC     1143
Lys Gln Met Tyr Glu His Phe Lys Gly Tyr Glu Tyr Val Ser His Ile
        220                 225                 230

AAC TGG AAC GAG GAC AAA GCG GCA GCC ATC CTG GAG GCC TGG CAG AGG     1191
Asn Trp Asn Glu Asp Lys Ala Ala Ala Ile Leu Glu Ala Trp Gln Arg
235                 240                 245                 250

ACA TAT GTG GAG GTG GTT CAT CAG AGT GTC GCA CAG AAC TCC ACT CAA     1239
Thr Tyr Val Glu Val Val His Gln Ser Val Ala Gln Asn Ser Thr Gln
                255                 260                 265

AAG GTG CTT TCC TTC ACC ACC ACG CTG GAC GAC ATC CTG AAA TCC         1287
Lys Val Leu Ser Phe Thr Thr Thr Leu Asp Asp Ile Leu Lys Ser
            270                 275                 280

TTC TCT GAC GTC AGT GTC ATC CGC GTG GCC AGC GGC TAC TTA CTC ATG     1335
Phe Ser Asp Val Ser Val Ile Arg Val Ala Ser Gly Tyr Leu Leu Met
        285                 290                 295

CTC GCC TAT GCC TGT CTA ACC ATG CTG CGC TGG GAC TGC TCC AAG TCC     1383
Leu Ala Tyr Ala Cys Leu Thr Met Leu Arg Trp Asp Cys Ser Lys Ser
300                 305                 310

CAG GGT GCC GTG GGG CTG GCT GGC GTC CTG CTG GTT GCA CTG TCA GTG     1431
Gln Gly Ala Val Gly Leu Ala Gly Val Leu Leu Val Ala Leu Ser Val
315                 320                 325                 330

GCT GCA GGA CTG GGC CTG TGC TCA TTG ATC GGA ATT TCC TTT AAC GCT     1479
Ala Ala Gly Leu Gly Leu Cys Ser Leu Ile Gly Ile Ser Phe Asn Ala
                335                 340                 345

GCA ACA ACT CAG GTT TTG CCA TTT CTC GCT CTT GGT GTT GGT GTG GAT     1527
Ala Thr Thr Gln Val Leu Pro Phe Leu Ala Leu Gly Val Gly Val Asp
            350                 355                 360

GAT GTT TTT CTT CTG GCC CAC GCC TTC AGT GAA ACA GGA CAG AAT AAA     1575
Asp Val Phe Leu Leu Ala His Ala Phe Ser Glu Thr Gly Gln Asn Lys
        365                 370                 375
```

FIG. 8-2

```
AGA ATC CCT TTT GAG GAC AGG ACC GGG GAG TGC CTG AAG CGC ACA GGA      1623
Arg Ile Pro Phe Glu Asp Arg Thr Gly Glu Cys Leu Lys Arg Thr Gly
    380             385                 390

GCC AGC GTG GCC CTC ACG TCC ATC AGC AAT GTC ACA GCC TTC TTC ATG      1671
Ala Ser Val Ala Leu Thr Ser Ile Ser Asn Val Thr Ala Phe Phe Met
395             400                 405                 410

GCC GCG TTA ATC CCA ATT CCC GCT CTG CGG GCG TTC TCC CTC CAG GCA      1719
Ala Ala Leu Ile Pro Ile Pro Ala Leu Arg Ala Phe Ser Leu Gln Ala
                415                 420                 425

GCG GTA GTA GTG GTG TTC AAT TTT GCC ATG GTT CTG CTC ATT TTT CCT      1767
Ala Val Val Val Val Phe Asn Phe Ala Met Val Leu Leu Ile Phe Pro
            430                 435                 440

GCA ATT CTC AGC ATG GAT TTA TAT CGA CGC GAG GAC AGG AGA CTG GAT      1815
Ala Ile Leu Ser Met Asp Leu Tyr Arg Arg Glu Asp Arg Arg Leu Asp
        445                 450                 455

ATT TTC TGC TGT TTT ACA AGC CCC TGC GTC AGC AGA GTG ATT CAG GTT      1863
Ile Phe Cys Cys Phe Thr Ser Pro Cys Val Ser Arg Val Ile Gln Val
    460                 465                 470

GAA CCT CAG GCC TAC ACC GAC ACA CAC GAC AAT ACC CGC TAC AGC CCC      1911
Glu Pro Gln Ala Tyr Thr Asp Thr His Asp Asn Thr Arg Tyr Ser Pro
475             480                 485                 490

CCA CCT CCC TAC AGC AGC CAC AGC TTT GCC CAT GAA ACG CAG ATT ACC      1959
Pro Pro Pro Tyr Ser Ser His Ser Phe Ala His Glu Thr Gln Ile Thr
                495                 500                 505

ATG CAG TCC ACT GTC CAG CTC CGC ACG GAG TAC GAC CCC CAC ACG CAC      2007
Met Gln Ser Thr Val Gln Leu Arg Thr Glu Tyr Asp Pro His Thr His
            510                 515                 520

GTG TAC TAC ACC ACC GCT GAG CCG CGC TCC GAG ATC TCT GTG CAG CCC      2055
Val Tyr Tyr Thr Thr Ala Glu Pro Arg Ser Glu Ile Ser Val Gln Pro
        525                 530                 535

GTC ACC GTG ACA CAG GAC ACC CTC AGC TGC CAG AGC CCA GAG AGC ACC      2103
Val Thr Val Thr Gln Asp Thr Leu Ser Cys Gln Ser Pro Glu Ser Thr
    540                 545                 550

AGC TCC ACA AGG GAC CTG CTC TCC CAG TTC TCC GAC TCC AGC CTC CAC      2151
Ser Ser Thr Arg Asp Leu Leu Ser Gln Phe Ser Asp Ser Ser Leu His
555             560                 565                 570

TGC CTC GAG CCC CCC TGT ACG AAG TGG ACA CTC TCA TCT TTT GCT GAG      2199
Cys Leu Glu Pro Pro Cys Thr Lys Trp Thr Leu Ser Ser Phe Ala Glu
                575                 580                 585

AAG CAC TAT GCT CCT TTC CTC TTG AAA CCA AAA GCC AAG GTA GTG GTG      2247
Lys His Tyr Ala Pro Phe Leu Leu Lys Pro Lys Ala Lys Val Val Val
            590                 595                 600

ATC TTC CTT TTT CTG GGC TTG CTG GGG GTC AGC CTT TAT GGC ACC ACC      2295
Ile Phe Leu Phe Leu Gly Leu Leu Gly Val Ser Leu Tyr Gly Thr Thr
        605                 610                 615

CGA GTG AGA GAC GGG CTG GAC CTT ACG GAC ATT GTA CCT CGG GAA ACC      2343
Arg Val Arg Asp Gly Leu Asp Leu Thr Asp Ile Val Pro Arg Glu Thr
    620                 625                 630
```

FIG. 8-3

```
AGA GAA TAT GAC TTT ATT GCT GCA CAA TTC AAA TAC TTT TCT TTC TAC      2391
Arg Glu Tyr Asp Phe Ile Ala Ala Gln Phe Lys Tyr Phe Ser Phe Tyr
635                 640                 645                 650

AAC ATG TAT ATA GTC ACC CAG AAA GCA GAC TAC CCG AAT ATC CAG CAC      2439
Asn Met Tyr Ile Val Thr Gln Lys Ala Asp Tyr Pro Asn Ile Gln His
                    655                 660                 665

TTA CTT TAC GAC CTA CAC AGG AGT TTC AGT AAC GTG AAG TAT GTC ATG      2487
Leu Leu Tyr Asp Leu His Arg Ser Phe Ser Asn Val Lys Tyr Val Met
                670                 675                 680

TTG GAA GAA AAC AAA CAG CTT CCC AAA ATG TGG CTG CAC TAC TTC AGA      2535
Leu Glu Glu Asn Lys Gln Leu Pro Lys Met Trp Leu His Tyr Phe Arg
            685                 690                 695

GAC TGG CTT CAG GGA CTT CAG GAT GCA TTT GAC AGT GAC TGG GAA ACC      2583
Asp Trp Leu Gln Gly Leu Gln Asp Ala Phe Asp Ser Asp Trp Glu Thr
700                 705                 710

GGG AAA ATC ATG CCA AAC AAT TAC AAG AAT GGA TCA GAC GAT GGA GTC      2631
Gly Lys Ile Met Pro Asn Asn Tyr Lys Asn Gly Ser Asp Asp Gly Val
715                 720                 725                 730

CTT GCC TAC AAA CTC CTG GTG CAA ACC GGC AGC CGC GAT AAG CCC ATC      2679
Leu Ala Tyr Lys Leu Leu Val Gln Thr Gly Ser Arg Asp Lys Pro Ile
                735                 740                 745

GAC ATC AGC CAG TTG ACT AAA CAG CGT CTG GTG GAT GCA GAT GGC ATC      2727
Asp Ile Ser Gln Leu Thr Lys Gln Arg Leu Val Asp Ala Asp Gly Ile
                750                 755                 760

ATT AAT CCC AGC GCT TTC TAC ATC TAC CTG ACG GCT TGG GTC AGC AAC      2775
Ile Asn Pro Ser Ala Phe Tyr Ile Tyr Leu Thr Ala Trp Val Ser Asn
            765                 770                 775

GAC CCC GTC GCG TAT GCT GCC TCC CAG GCC AAC ATC CGG CCA CAC CGA      2823
Asp Pro Val Ala Tyr Ala Ala Ser Gln Ala Asn Ile Arg Pro His Arg
            780                 785                 790

CCA GAA TGG GTC CAC GAC AAA GCC GAC TAC ATG CCT GAA ACA AGG CTG      2871
Pro Glu Trp Val His Asp Lys Ala Asp Tyr Met Pro Glu Thr Arg Leu
795                 800                 805                 810

AGA ATC CCG GCA GCA GAG CCC ATC GAG TAT GCC CAG TTC CCT TTC TAC      2919
Arg Ile Pro Ala Ala Glu Pro Ile Glu Tyr Ala Gln Phe Pro Phe Tyr
                815                 820                 825

CTC AAC GGC TTG CGG GAC ACC TCA GAC TTT GTG GAG GCA ATT GAA AAA      2967
Leu Asn Gly Leu Arg Asp Thr Ser Asp Phe Val Glu Ala Ile Glu Lys
            830                 835                 840

GTA AGG ACC ATC TGC AGC AAC TAT ACG AGC CTG GGG CTG TCC AGT TAC      3015
Val Arg Thr Ile Cys Ser Asn Tyr Thr Ser Leu Gly Leu Ser Ser Tyr
        845                 850                 855

CCC AAC GGC TAC CCC TTC CTC TTC TGG GAG CAG TAC ATC GGC CTC CGC      3063
Pro Asn Gly Tyr Pro Phe Leu Phe Trp Glu Gln Tyr Ile Gly Leu Arg
860                 865                 870

CAC TGG CTG CTG CTG TTC ATC AGC GTG GTG TTG GCC TGC ACA TTC CTC      3111
His Trp Leu Leu Leu Phe Ile Ser Val Val Leu Ala Cys Thr Phe Leu
875                 880                 885                 890
```

FIG. 8-4

```
GTG TGC GCT GTC TTC CTT CTG AAC CCC TGG ACG GCC GGG ATC ATT GTG         3159
Val Cys Ala Val Phe Leu Leu Asn Pro Trp Thr Ala Gly Ile Ile Val
            895                 900                 905

ATG GTC CTG GCG CTG ATG ACG GTC GAG CTG TTC GGC ATG ATG GGC CTC         3207
Met Val Leu Ala Leu Met Thr Val Glu Leu Phe Gly Met Met Gly Leu
            910                 915                 920

ATC GGA ATC AAG CTC AGT GCC GTG CCC GTG GTC ATC CTG ATC GCT TCT         3255
Ile Gly Ile Lys Leu Ser Ala Val Pro Val Val Ile Leu Ile Ala Ser
            925                 930                 935

GTT GGC ATA GGA GTG GAG TTC ACC GTT CAC GTT GCT TTG GCC TTT CTG         3303
Val Gly Ile Gly Val Glu Phe Thr Val His Val Ala Leu Ala Phe Leu
            940                 945                 950

ACG GCC ATC AGC GAC AAG AAC CGC AGG GCT GTG CTT GCC CTG GAG CAC         3351
Thr Ala Ile Ser Asp Lys Asn Arg Arg Ala Val Leu Ala Leu Glu His
955                 960                 965                 970

ATG TTT GCA CCC GTC CTG GAT GGC GCC GTG TCC ACT CTG CTG GGA GTG         3399
Met Phe Ala Pro Val Leu Asp Gly Ala Val Ser Thr Leu Leu Gly Val
            975                 980                 985

CTG ATG CTG GCG GGA TCT GAG TTC GAC TTC ATT GTC AGG TAT TTC TTT         3447
Leu Met Leu Ala Gly Ser Glu Phe Asp Phe Ile Val Arg Tyr Phe Phe
            990                 995                 1000

GCT GTG CTG GCA ATC CTC ACC ATC CTC GGC GTT CTC AAT GGG CTG GTT         3495
Ala Val Leu Ala Ile Leu Thr Ile Leu Gly Val Leu Asn Gly Leu Val
            1005                1010                1015

TTG CTT CCC GTG CTT TTG TCT TTC TTT GGA CCA TAT CCT GAG GTG TCT         3543
Leu Leu Pro Val Leu Leu Ser Phe Phe Gly Pro Tyr Pro Glu Val Ser
            1020                1025                1030

CCA GCC AAC GGC TTG AAC CGC CTG CCC ACA CCC TCC CCT GAG CCA CCC         3591
Pro Ala Asn Gly Leu Asn Arg Leu Pro Thr Pro Ser Pro Glu Pro Pro
1035                1040                1045                1050

CCC AGC GTG GTC CGC TTC GCC ATG CCG CCC GGC CAC ACG CAC AGC GGG         3639
Pro Ser Val Val Arg Phe Ala Met Pro Pro Gly His Thr His Ser Gly
            1055                1060                1065

TCT GAT TCC TCC GAC TCG GAG TAT AGT TCC CAG ACG ACA GTG TCA GGC         3687
Ser Asp Ser Ser Asp Ser Glu Tyr Ser Ser Gln Thr Thr Val Ser Gly
            1070                1075                1080

CTC AGC GAG GAG CTT CGG CAC TAC GAG GCC CAG CAG GGC GCG GGA GGC         3735
Leu Ser Glu Glu Leu Arg His Tyr Glu Ala Gln Gln Gly Ala Gly Gly
            1085                1090                1095

CCT GCC CAC CAA GTG ATC GTG GAA GCC ACA GAA AAC CCC GTC TTC GCC         3783
Pro Ala His Gln Val Ile Val Glu Ala Thr Glu Asn Pro Val Phe Ala
            1100                1105                1110

CAC TCC ACT GTG GTC CAT CCC GAA TCC AGG CAT CAC CCA CCC TCG AAC         3831
His Ser Thr Val Val His Pro Glu Ser Arg His His Pro Pro Ser Asn
1115                1120                1125                1130

CCG AAA CAG CAG CCC CAC CTG GAC TCA GGG TCC CTG CCT CCC GGA CGG         3879
Pro Lys Gln Gln Pro His Leu Asp Ser Gly Ser Leu Pro Pro Gly Arg
            1135                1140                1145
```

FIG. 8-5

| | |
|---|---|
| CAA GGC CAG CAG CCC CGC AGG GAC CCC CCC AGA AAA GGC TTG TGG CCA<br>Gln Gly Gln Gln Pro Arg Arg Asp Pro Pro Arg Lys Gly Leu Trp Pro<br>              1150                        1155                        1160 | 3927 |
| CCC CTC TAC AGA CCG CGC AGA GAC GCT TTT GAA ATT TCT ACT GAA GGG<br>Pro Leu Tyr Arg Pro Arg Arg Asp Ala Phe Glu Ile Ser Thr Glu Gly<br>              1165                        1170                        1175 | 3975 |
| CAT TCT GGC CCT AGC AAT AGG GCC CGC TGG GGC CCT CGC GGG GCC CGT<br>His Ser Gly Pro Ser Asn Arg Ala Arg Trp Gly Pro Arg Gly Ala Arg<br>              1180                        1185                        1190 | 4023 |
| TCT CAC AAC CCT CGG AAC CCA ACG TCC ACT GCC ATG GGC AGC TCC GTG<br>Ser His Asn Pro Arg Asn Pro Thr Ser Thr Ala Met Gly Ser Ser Val<br>1195                        1200                        1205                        1210 | 4071 |
| CCC GGC TAC TGC CAG CCC ATC ACC ACT GTG ACG GCT TCT GCC TCC GTG<br>Pro Gly Tyr Cys Gln Pro Ile Thr Thr Val Thr Ala Ser Ala Ser Val<br>                       1215                        1220                        1225 | 4119 |
| ACT GTC GCC GTG CAC CCG CCG CCT GTC CCT GGG CCT GGG CGG AAC CCC<br>Thr Val Ala Val His Pro Pro Pro Val Pro Gly Pro Gly Arg Asn Pro<br>              1230                        1235                        1240 | 4167 |
| CGA GGG GGA CTC TGC CCA GGC TAC CCT GAG ACT GAC CAC GGC CTG TTT<br>Arg Gly Gly Leu Cys Pro Gly Tyr Pro Glu Thr Asp His Gly Leu Phe<br>               1245                        1250                        1255 | 4215 |
| GAG GAC CCC CAC GTG CCT TTC CAC GTC CGG TGT GAG AGG AGG GAT TCG<br>Glu Asp Pro His Val Pro Phe His Val Arg Cys Glu Arg Arg Asp Ser<br>1260                        1265                        1270 | 4263 |
| AAG GTG GAA GTC ATT GAG CTG CAG GAC GTG GAA TGC GAG GAG AGG CCC<br>Lys Val Glu Val Ile Glu Leu Gln Asp Val Glu Cys Glu Glu Arg Pro<br>1275                        1280                        1285                        1290 | 4311 |
| CGG GGA AGC AGC TCC AAC TGAGGGTGAT TAAAATCTGA AGCAAAGAGG<br>Arg Gly Ser Ser Ser Asn<br>             1295 | 4359 |
| CCAAAGATTG GAAACCCCCC ACCCCCACCT CTTTCCAGAA CTGCTTGAAG AGAACTGGTT | 4419 |
| GGAGTTATGG AAAAGATGCC CTGTGCCAGG ACAGCAGTTC ATTGTTACTG TAACCGATTG | 4479 |
| TATTATTTTG TTAAATATTT CTATAAATAT TTAAGAGATG TACACATGTG TAATATAGGA | 4539 |
| AGGAAGGATG TAAAGTGGTA TGATCTGGGC CTTCTCCACT CCTGCCCCAG AGTGTGGAGG | 4599 |
| CCACAGTGGG GCCTCTCCGT ATTTGTGCAT TGGGCTCCGT GCCACAACCA AGCTTCATTA | 4659 |
| GTCTTAAATT TCAGCATATG TTGCTGCTGC TTAAATATTG TATAATTTAC TTGTATAATT | 4719 |
| CTATGCAAAT ATTGCTTATG TAATAGGATT ATTTTGTAAA GGTTCTGTT TAAAATATTT | 4779 |
| TAAATTTGCA TATCACAACC CTGTGGTAGT ATGAAATGTT ACTGTTAACT TTCAAACACG | 4839 |
| CTATGCGTGA TAATTTTTTT GTTAATGAG CAGATATGAA GAAAGCACGT TAATCCTGGT | 4899 |
| GGCTTCTCTA GGTGTCGTTG TGTGCGGTCC TCTTGTTTGG CTGTGCGTGT GAACACGTGT | 4959 |
| GTGAGTTCAC CATGTACTGT ACTGTGATTT TTTTTTTTGT CTTGTTTTGT TTCTCTACAC | 5019 |
| TGTCTGTAAC CTGTAGTAGG CTCTGACCTA TTCAGGCTGG AAAGCGTCAG GATATCTTTT | 5079 |

FIG. 8-6

```
CTTCGTGCTG GTGAGGGCTG GCCCTAAACA TCCACCTAAT CCTTTCAAAT CAGCCCGGCA    5139

AAAGCTAAAC TCTCCTCGTG TCTACGGGCA TCTGTTATGA TCATTGGCTG CCATCCAGGA    5199

CCCCAATTTG TGCTTCAGGG GGATAATCTC CTTCTCTCGG ATCATTGTGA TGGATGCTGG    5259

AACCTCAGGG TATGGAGCTC ACATCAGTTC ATCATGGTGG GTGTTAGAGA ATTCGGTGAC    5319

ATGCCTAGTG CTGAGCCTTG GCTGGGCCAT GAGAGTCTGT ATAATAAAAA AAGCATGCAG    5379

CATGGTGCCC CTCTTTTGAC CAACACACAC AAGACCCCTC CCCCAACACC CCCAAATTCA    5439

AGAGTGGATG TGGCCCTGTC ACAGGTAGAA AAACCTATTT AGTTAATTCT TTCTTGGCCC    5499

ACAGTCTCCC AGAAATGATG TTTTGAGTCC CTATAGTTTA AAGTCCCTCT CTTAAATGGA    5559

GCAGCTGGTT TGAGGTTTCT AAATCTGTTT GCATTTCTT TAAAATTAAG TGGTGAGCAT     5619

GCATTGTGGT GTAGAGGCAG GCATTATGTA GGATAAGAGC TCCGGGGGA TTCTTCATGC     5679

ACCAGTGTTT AGGGTACGTG CTTCCTAAGT AAATCCAAAC ATTGTCTCCA TCCTCCCCGT    5739

CATTAGTGCT CTTTCAATGT GATGTGGGAA AGCAGGAGGA TGGACACACC CCACTGAAAG    5799

ATGTAGGCAG GGGCAGGTCT CTCAACCAGG CATATTTTTA AAAGTTGCTT CTGTACTGGT    5859

TCTCTTCTTT TGCTCTGAGG TGTGGGCTCC CTCATCTCGT AACCAGAGAC CAGCACATGT    5919

CAGGGAAGCA CCCAGTGTCG GCTCCCCATC CCAATCCACA CCAGCACCTT GTTACAGACA    5979

AGAAGTCAGA GGAAAGGGCG GGGTCCCTGC AGGGCTGAAG CCTAAGCTAC TGTGAGGTGC    6039

TCACAAGTGG CAGCTCCTGT AATCCCTTTT AAATTACGTG GGAATCTTAA CAGAAAGTAA    6099

TGGGCCCCCA GAAATACCCA CAGCATAGGA CNTCAGACCC TGAACTCACC ACAAAATTTT    6159

AAGATGCTGA TTGGGAGCCG CTTGTGGCTG CTGGATGNGT GTGTGTGTGT GTGTGTGTGC    6219

GTGCGTGCGT GTGTGTGTGT GTCTGNTGGG GACCCTGGCC ACCCCCTGC TGCTGTCTTG     6279

GTGCCTGTCA CCCACATGGT CTGCCATCCT AACACCCAGC TCTGCTCAGA AAACGTCCTG    6339

CGTGGAGGAG GGATGATGCA GAATTCTGAA GTCGACTTCC CTCTGGCTCC TGGCGTGCCC    6399

TCGCTCCCTT CCTGAGCCCA GCTCGTGTTG CGCCGGAGGC TGCGCGGCCC CTGATTTCTG    6459

CATGGTGTAG AACTTTCTCC AATAGTCACA TTGGCAAAGG GAGAACTGGG GTGGGCGGGG    6519

GGTGGGGCTG GCAGGGAATT AGCATTTCTC TCTCTCTTTT AATAGTTAA                6568
```

FIG. 8-7

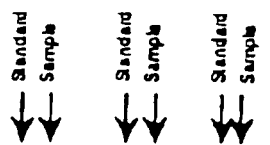

Sequences of Exons 1b and 1a

```
    aTCTTCCGCGAACTGGATGTGGGCAGCGGCGGCCAGCAgAGACcTCGGGACCCCgCGCAA
1   ------------+----------+----------+----------+----------+----------+  60
    tAGAAGGCGCTTGACCTACACCCGTCGCCGCCGGTCGTcTCTGgAGCCCTGGGGcGCGTT

N         N
                                        o         o
                                        t         t
                                        I         I
    TGTGGCAATGGAAGGCGCAgGGTCTGACTCCCCGGCAGCGGCCGCGGCCGCAGCGGCAGC
61  ------------+----------+----------+----------+----------+----------+  120
    ACACCGTTACCTTCCGCGTCCCAGACTGAGGGGCCGTCGCCGGCGCCGGCGTCGCCGTCG

AGCGCCCGCCGTGTGAGCAGCAGCAGCGGCTGGTCTGTCAACCGGAGCCCGAGCCCGAGC
121 ------------+----------+----------+----------+----------+----------+  180
    TCGCGGGCGGCACACTCGTCGTCGTCGCCGACCAGACAGTTGGCCTCGGGCTCGGGCTCG

AGCgAGCGGCCAGCAGCGTCcTCGCAAGCCGAGCGCCCAGGCGCGCCAGGAGCCCGCAGC
181 ------------+----------+----------+----------+----------+----------+  240
    TCGcTCGCCGGTCGTCGCAGgAGCGTTCGGCTCGCGGGTCCGCGCGGTCCTCGGGCGTCG

AGCGGCAGCAGCGCGCCGGGCCGCCCGGGAAGCCTCCGTCCCGCGGCGGCGGCGGCGGC
241 ------------+----------+----------+----------+----------+----------+  300
    TCGCCGTCGTCGCGCGGCCCGGCGGGCCCTTCGGAGGCAGGGCGCCGCCGCCGCCGCCG start
                MuPTC I                                              exon IB
    GGCGGCAAC ATGGCCTCGGCTGGTAAC GCCGCCGAGCCCCAgGACCGCGGCGGCGGCGGC
301 ------------+----------+----------+----------+----------+----------+  360
    CCGCCGTTGTACCGGAGCCGACCATTGCGGCGGCTCGGGGTCCTGGCGCCGCCGCCGCCG AGCGGCTGTATCGGTGCCCCGGGACGGCCGGCTGGAGGCGGGAGGCGCAcACGGACGGGG
361 ------------+----------+----------+----------+----------+----------+  420
    TCGCCGACATAGCCACGGGGCCCTgCCGGCCGACCTCCGCCCTCCGCGTgTGCCTGCCCC GGGCTGCGCCGTGCTGCCGCGCCGGACCGGGACTATCTGCACCGGCCCAGCTACTGCGAC
421 ------------+----------+----------+----------+----------+----------+  480
    CCCGACGCGGCACGACGGCGCGGCCTGGCCCTGATAGACGTGGCCGGGTCGATGACGCTG
                                                              end exon
    GCCGCCTTCGCTCTGGAGCAgATTTCCAAG GTGCATTTCAgACTCTCTCCTCCCACTTTC  IB
481 ------------+----------+----------+----------+----------+----------+  540
    CGGCG GAAGCGAGACCTCGTCTAAA GGTTCCACGTAAAGTCTGAGAGAGGAGGGTGAAAG
          MuPTC RI
    TCTTCCCTCCTCTAACTCTTTGGGATCGCCCCgCCaCACACAAACACACACACTCTCTT
541 ------------+----------+----------+----------+----------+----------+  600
    AGAAGGGAGGAGATTGAGAAACCCTAGCGGGGCGGtGTGTGTTTGTGTGTGTGAGAGAA CCTCTCTCTCTCACAcACACACACATgCtCaCgCtGCTGCCTCCACGAAAAGCAgCAG
601 ------------+----------+----------+----------+----------+----------+  660
    GGAGAGAGAGAGTGTGtGTGTGTGTGTAcGaGtGcGaCGACGGAGGTGCTTTTCGTcGTC
```

FIG. 12A

```
       AGACAAATGGGGATTGAAAAATTCAAACCCTCCCTCTGGTCCTGGGAGGAAAGGGCTGTC
 661   ------------+---------+---------+---------+---------+---------+  720
       TCTGTTTACCCCTAACTTTTTAAGTTTGGGAGGGAGACCAGGACCCTCCTTTCCCGACAG

TGAGGTCCGCAGGGGGTGGAGGTGTGTGTGTGTGCGTGTGTGTGTGTATACACACGCC
 721   ------------+---------+---------+---------+---------+---------+  780
       ACTCCAGGCGTCCCCCACCTCCACACACACACACGCACACACACACATATGTGTGCGG

CTCCCTGGTGTGCCTTTTCCGGAGCACTGGAAAGCCGTCCACGGCGGACCACCTCAAGGG
 781   ------------+---------+---------+---------+---------+---------+  840
       GAGGGACCACACGGAAAAGGCCTCGTGACCTTTCGGCAGGTGCCGCCTGGTGGAGTTCCC

N
                        o
                        t
                        I
       CGGCCGCGGCACTGTCCTGCCCCGTGCCCCCTGCCCTGAACTTCTTCCTCCTGCGCCCCT
 841   ------------+---------+---------+---------+---------+---------+  900
       GCCGGCGCCGTGACAGGACGGGGCACGGGGACGGGACTTGAAGAAGGAGGACGCGGGGA

GCCCCTATTTGCAGCCTAAACTCCTGTACGGCTGCCACATTTCTTAACATCTTGGAAGGG
 901   ------------+---------+---------+---------+---------+---------+  960
       CGGGGATAAACGTCGGATTTGAGGACATGCCGACGGTGTAAAGAATTGTAGAACCTTCCC

GAGCGGAGTGGAGAGAGAGCGGAGAGAGGAAGGGGGGAGGGGAGCCGAAATAAAGGTGGT
 961   ------------+---------+---------+---------+---------+---------+ 1020
       CTCGCCTCACCTCTCTCTCGCCTCTCTCCTTCCCCCCTCCCCTCGGCTTTATTTCCACCA

TTCCTTTTTTGCAGCCAGTTTTGTTGAGCATGAAATCTCTGCTCCATTAAAAAATTATTN
1021   ------------+---------+---------+---------+---------+---------+ 1080
       AAGGAAAAAACGTCGGTCAAAACAACTCGTACTTTAGAGACGAGGTAATTTTTTAATAAN

TCGGAAAAAGATATCCCCCCAGTTTTCCAGGTTTTGAGCCGCCTCTCCTTAGGGCCTGGT
1081   ------------+---------+---------+---------+---------+---------+ 1140
       AgCCTTTTTCTATAGGGGGGTCAAAAgGTCCAAAACTCGGCGGAGAGgAATCCCGGACCA

CGGGGGAGGAAAAGTTGTAAACAAATTGCCACATTAAATTCGCGGTGCGAGTCTGCGGAG
1141   ------------+---------+---------+---------+---------+---------+ 1200
       GCCCCCTCCTTTTCAACATTTGTTTAACGGTGTAATTTAAgCGCCACGCTCAgACGCCTC
                                                         PTC F18  start exon I
       CTGCCGGGTTCATTGTGTNTACGAGGCTCGCTGAAATGTGTGGAATCCAGG|GAAGGCGAG
1201   ------------+---------+---------+---------+---------+---------+ 1260
       GACGGCCCAAgTAACACANATGCTCCGAGCgACTTTACACACCTTAGGTCCCTTCCGCTC

|CACCCAGAC|GGGGGCCCGCCGGGGTCGCGGCCAGCGCCGGGGAAATGCCGCGCCGGGGAG
1261   ------------+---------+---------+---------+---------+---------+ 1320
       GTGGGTCTGCCCCCGGGCGGCCCCAGCGCCGGTCGCGGCCCCTTTACGGCGCGGCCCCTC

CAGCATGCGCCGGCCTGAGCCCTTCCCTTTGCACTCGGCTGTTTTTTACGTTTAACCAGA
1321   ------------+---------+---------+---------+---------+---------+ 1380
       GTCGTACGCGGCCGGACTCGGGAAGGGAAACGTGAGCCGACAAAAAATGCAAATTGGTCT

AAGGAAGGGAGAGGAGGGAAAGATCCATGTGGCTGCCCTCTTCCGATCACAAATATTGTC| end exon I
1381   ------------+---------+---------+---------+---------+---------+ 1440
       TTC|CTTCCCTCTCCTCCCTTTCT|AGGTACACCGACGGGAGAAGGCTAGTGTTTATAACAG
          PTC R18                                  splice
       GTAAGTTGCAGCTGGCTGCCCCACTTCCTAATTCAGCTCACACAG|CCTCTCCCCAC|GCTA
1441   ------------+---------+---------+---------+---------+---------+ 1500
       CATTCAACGTCGACCGACGGGGTGAAGGATTAAGTCGAGTGTGTCGGAGAGGGGTGCGAT
```

FIG. 12B

```
                                              B
                                              a
                             N                m
                             o                H
      PTC F22                t                I
      TGGAAATGCGTCGG|GAGTGAACTCCGGCGGCCGCGCTCACCACGTGGATCCCCACTTACT
1501  ---------+---------+---------+---------+---------+---------+  1560
      ACCTTTACGCAGCCCTCACTTGAGGCCGCCGGCGCGAGTGGTGCACCTAGGGGTGAATGA

ACCATTCTCGGCGGGGGTCCAGTTGGGGGAACCCGCAATATGTTGTTCCAAAGAGCGCTC
1561  ---------+---------+---------+---------+---------+---------+  1620
      TGGTAAGAGCCGCCCCCAGGTCAACCCCCTTGGGCGTTATACAACAAGGTTTCTCGCGAG

GCCCCTAGCGCCCGTCCCCGAGGGTGATGGACAGAGCAGGACTGGTTTGCTGGCTCCTGA
1621  ---------+---------+---------+---------+---------+---------+  1680
      CGGGGATCGCGGGCAGGGGCTCCC|ACTACCTGTCTCGTCCTGAC|CAAACGACCGAGGACT
                              PTC R22
      ACCTTGGGCTCCATCGCTGGGATTACGCAGCCCCTCCCTTCTCAGCTCTGGG|GT
1681  ---------+---------+---------+---------+---------+--  1732
      TGGAACCCGAGGTAGCGACCCTAATGCGTCGGGGAGGGAAGAGTCGAGACCC
                                                          end exon IA
```

FIG. 12C

Sequence of exon 2a.

SEQ ID NO:59:

```
  ┌─ HH57
  B
  a
  m
  H
  I        ←
    GGATCCNNTCACGTGACCCTGACAGTTCCTGCTTATGGCGCGGCAGACCACCCACGCCGA
  1 ---------+---------+---------+---------+---------+---------+  60
    CCTAGGNNAGTGCACTGGGACTGTCAAGGACGAATACCGCGCCGTCTGGTGGGTGCGGCT

G  S  ?  H  V  T  L  T  V  P  A  Y  G  A  A  D  H  P  R  R   -
      D  P  ?  T  *  P  *  Q  F  L  L  M  A  R  Q  T  T  H  A  E  -
       I  ?  S  R  D  P  D  S  S  C  L  W  R  G  R  P  P  T  P  R -

GGGCCATGGAACTGCTTAATAGAAACAGGCTTGTAATTGTGAGTCCGCGCTGCACTCCGC
 61 ---------+---------+---------+---------+---------+---------+ 120
    CCCGGTACCTTGACGAATTATCTTTGTCCGAACATTAACACTCAGGCGCGACGTGAGGCG

G  P  W  N  C  L  I  E  T  G  L  *  L  *  V  R  A  A  L  R   -
      G  H  G  T  A  *  *  K  Q  A  C  N  C  E  S  A  L  H  S  A  -
       A  M  E  L  L  N  R  N  R  L  V  I  V  S  P  R  C  T  P  P -

H
     i                B
     n                s
     d                s
     I                H
     I                I
     I                I
    CGAAAGCTTCCGGCGGCCCAGCGCGCCGGGGTTTTTACACTTTCCGTTCCTTTTGTAAAG
121 ---------+---------+---------+---------+---------+---------+ 180
    GCTTTCGAAGGCCGCCGGGTCGCGCGGCCCCAAAAATGTGAAAGGCAAGGAAAACATTTC

R  K  L  P  A  A  Q  R  A  G  V  F  T  L  S  V  P  F  V  K   -
      E  S  F  R  R  P  S  A  P  G  F  L  H  F  P  F  L  L  *  R  -
       K  A  S  G  G  P  A  R  R  G  F  Y  T  F  R  S  F  C  K  D -

ACGGAGGAGGAGGAGAAGAAGAAGAAGAAAACGGAGGAGAAGAAAAAGACGACAGGGGAG
181 ---------+---------+---------+---------+---------+---------+ 240
    TGCCTCCTCCTCCTCTTCTTCTTCTTTTGCCTCCTCTTCTTTTTCTGCTGTCCCCTC

T  E  E  E  E  K  K  K  K  K  T  E  E  K  K  K  T  T  G  E   -
      R  R  R  R  R  R  R  R  R  K  R  R  R  R  K  R  R  Q  G  R  -
       G  G  G  G  E  E  E  E  E  N  G  G  E  E  K  D  D  R  G  D -

ACAAAGAGACCCGCAGCGACAAGGCAAGGGGGAGACGAGGGAAGACTGGGAGAAGACGGA
241 ---------+---------+---------+---------+---------+---------+ 300
    TGTTTCTCTGGGCGTCGCTGTTCCGTTCCCCCTCTGCTCCCTTCTGACCCTCTTCTGCCT
```

FIG. 13A

```
          T  K  R  P  A  A  T  R  Q  G  G  D  E  G  R  L  G  E  D  G   -
        Q  R  D  P  Q  R  Q  G  K  G  E  T  R  E  D  W  E  K  T  E   -
          K  E  T  R  S  D  K  A  R  G  R  R  G  K  T  G  R  R  R  R  -
             ┌Start exon 2A                                  PTCXFI
      GGAGC GGAGGACGA GGAAAGGGGGGCCAGGGAAAAA AAATTGATGTGAAATCCAAGCC CG
301   ---------+---------+---------+---------+---------+---------+  360
      CCTCGCCTCCTGCTCCTTTCCCCCCGGTCCCTTTTTTTTAACTACACTTTAGGTTCGGGC G  A  E  D  E  E  R  G  A  R  E  K  K  L  M  *  N  P  S  P   -
        E  R  R  T  R  K  G  G  P  G  K  K  N  *  C  E  I  Q  A  R   -
          S  G  G  R  G  K  G  G  Q  G  K  K  I  D  V  K  S  K  P  A  -
                                    E
                                    a
                                    g
                                    I        End exon 2A
      CGCTCCGAGCAGGGGTTGACGGCCGGCTATG GTNAGTGCAGCCAGCGCGGCNGCCGCCGA
361   ---------+---------+---------+---------+---------+---------+  420
      GCGAG GCTCGTCCCCAACTG CCGGCCGATACCANTCACGTCGGTCGCGCCGNCGGCGGCT R  S  E  Q  G  L  T  A  G  Y  G  ?  C  S  Q  R  G  ?  R  R   -
        A  P  S  R  G  *  R  P  A  M  V  S  A  A  S  A  A  A  A  D   -
          L  R  A  G  V  D  G  R  L  W  ?  V  Q  P  A  R  ?  P  P  T  -
      CGCCACCTCGCCTCTCGCGCCNTGCTCCTCGGGCGGCGCGGGGACNCTGGGACNCGGGAC
421   ---------+---------+---------+---------+---------+---------+  480
      GCGGTGGAGCGGAGAGCGCGGNACGAGGAGCCCGCCGCGCCCCTGNGACCCTGNGCCCTG R  H  L  A  S  R  A  ?  L  L  G  R  R  G  D  ?  G  T  R  D   -
        A  T  S  P  L  A  P  C  S  S  G  G  A  G  T  L  G  ?  G  T   -
          P  P  R  L  S  R  ?  A  P  R  A  A  R  G  ?  W  D  ?  G  R  -
      GCCCCNCNCGGCGGACGGANGAGCNAGCCCCGATCGCCGGGCNGGAGGGGCGGGCCNCGC
481   ---------+---------+---------+---------+---------+---------+  540
      CGGGGNGNGCCGCCTGCCTNCTCGNTCGGGGCTAGCGGCCCGNCCTCCCCGCCCGGNGCG A  P  ?  G  G  R  ?  S  ?  P  R  S  P  G  ?  R  G  G  P  R   -
        P  ?  ?  A  D  G  ?  A  S  P  D  R  R  A  G  G  A  G  ?  A   -
          P  ?  ?  R  R  T  ?  E  ?  A  P  I  A  G  ?  E  G  R  A  ?  R  -
                           B
                           a
                           m
                           H
                           I
      GCCNGGGCCGTGGATCCGGGTGGGCTGCGCCGCCTGGGCTCNGGANCNCTGGTCNCGCTC
541   ---------+---------+---------+---------+---------+---------+  600
      CGGNCCCGGCACCTAGGCCCACCCGACGCGGCGGACCCGAGNCCTNGNGACCAGNGCGAG A  ?  A  V  D  P  G  G  L  R  R  L  G  S  G  ?  L  V  ?  L   -
        P  G  P  W  I  R  V  G  C  A  A  W  A  ?  ?  ?  W  S  R  S   -
          ?  G  R  G  S  G  W  A  A  P  P  G  L  ?  ?  ?  G  ?  A  P  -
                                             S
                                             m
                                             a
                                             I
      CTCCNCTCTCNCTCGCACNCCCGGGCCCCCGCCCCCNATGCNATCCCCTCTTGGCNGGGA
601   ---------+---------+---------+---------+---------+---------+  660
      GAGGNGAGAGNGAGCGTGNGGGCCCGGGGGCGGGGGNTACGNTAGGGGAGAACCGNCCCT
```

BASAL CELL CARCINOMA TUMOR SUPRESSOR GENE

CROSS REFERENCE TO RELATED APPLICATIONS

This application is a continuation-in-part of U.S. application Ser. No. 60/017,906, filed on May 17, 1996 and U.S. application Ser. No 60/019,765, filed on Jun. 14, 1996, both of which are herein incorporated by reference for all purposes.

BACKGROUND OF THE INVENTION

This invention pertains to the field of oncology. In particular, this invention pertains to the discovery of a tumor suppressor gene implicated in the etiology of nevoid basal cell carcinoma syndrome (NBCCS) and various cancers including basal cell carcinomas.

Many cancers are believed to result from a series of genetic alterations leading to progressive disordering of normal cellular growth mechanisms (Nowell (1976) *Science* 194:23, Foulds (1958) *J. Chronic Dis.* 8:2). In particular, the deletion or multiplication of copies of whole chromosomes or chromosomal segments, or specific regions of the genome are common (see, e.g., Smith et al. (1991) *Breast Cancer Res. Treat.* 18: Suppl. 1: 5–14; van de Vijer & Nusse (1991) *Biochim. Biophys. Acta.* 1072: 33–50; Sato et al. (1990) *Cancer. Res.* 50: 7184–7189). In particular, the amplification and deletion of DNA sequences containing proto-oncogenes and tumor-suppressor genes, respectively, are frequently characteristic of tumorigenesis. Dutrillaux et al. (1990) *Cancer Genet. Cytogenet.* 49: 203–217.

One cancer-related syndrome that appears to have a strong genetic base is the nevoid basal cell carcinoma syndrome (NBCCS). The nevoid basal cell carcinoma syndrome (NBCCS), also known as Gorlin syndrome and the basal cell nevus syndrome, is an autosomal dominant disorder that predisposes to both cancer and developmental defects (Gorlin (1995) *Dermatologic Clinics* 13: 113–125). Its prevalence has been estimated at 1 per 56,000, and 1–2% of medulloblastomas and 0.5% of basal cell carcinomas (BCCs) are attributable to the syndrome (Springate (1986) *J. Pediatr. Surg.* 21: 908–910; Evans et al. (1991) *British J. Cancer.* 64: 959–961). In addition to basal cell carcinomas (BCCs) and medulloblastomas, NBCCS patients are also at an increased risk for ovarian fibromas, meningiomas, fibrosarcomas, rhabdomyosarcomas, cardiac fibromas and ovarian dermoids (Evans et al. (1991) supra., Evans et al. (1993) *J. Med. Genet.* 30: 460–464; Gorlin (1995) supra.).

Non-neoplastic features, including odontogenic keratocysts (which are most aggressive in the second and third decades of life), pathognomonic dyskeratotic pittina of the hands and feet, and progressive intracranial calcification (usually evident from the second decade) are very common. There is a broad range of skeletal defects (Gorlin (1995) supra.; Shanley et al. (1994) *Am. J. Med. Genet.* 50: 282–290) including rib, vertebral and shoulder anomalies, pectus excavatum, immobile thumbs and polydactyly. Craniofacial and brain abnormalities include cleft palate, characteristic coarse fades, strabismus, dysgenesis of the corpus callosum macrocephaly and frontal bossing (Gorlin (1995) supra.). Generalized overgrowth (Bale et al. (1991) *Am. J. Med. Genet.* 40: 206–210) and acromegalic appearance are common, but growth hormone and IGF1 levels are not elevated.

Implications for the affected individual can be severe, predominantly due to the prolific basal cell carcinomas which can number more than 500 in a lifetime (Shanley et al. (1994) supra). Expression of many features of the syndrome is variable, but the severity tends to breed true within families (Anderson et al. (1967) *Am. J. Hum. Genet.,* 19:12–22). This variation between families may reflect specific phenotypic effects of different mutations, modifier genes, or environmental factors (sunlight exposure is likely to play a role in the age of onset and incidence of basal cell carcinomas). One third to one half of patients have no affected relatives and are presumed to be the product of new germ cell mutations (Gorlin (1995) supra.). Unilateral and segmental NBCCS are attributed to somatic mutation in one cell of an early embryo (Gutierrez and Mora (1986) *J. Am. Acad. Dermatol.* 15: 1023–1029).

The NBCCS syndrome was mapped to one or more genes at chromosome 9q22–31 (Gailani et al. (1992) *Cell* 69: 111–117; Reis et al. (1992) *Lancet* 339: 617; Farndon et al. (1992) *Lancet* 339: 581–2). In addition, it has been demonstrated that the same region is deleted in a high percentage of basal cell carcinomas and other tumors related to the disorder (Gailani et al. (1992) supra.) thus suggesting that the NBCCS gene functions as a tumor suppressor. Inactivation of NBCCS gene(s) may be a necessary if not sufficient event for the development of basal cell carcinomas (Shanley et al. (1995) *Hum. Mol. Genet.* 4: 129–133; Gailani et al. (1996) *J. Natl. Canc. Inst.* 88: 349–354).

Since the original mapping of the gene in 1992, linkage studies have narrowed the NBCCS region to a 4 cM interval between D9S180 and D9S196 (Goldstein et al. (1994) *Am. J. Hum. Genet.* 54: 765–773; Wicking et al. (1994) *Genomics* 22: 505–511). Reported recombination involving an unaffected individual tentatively placed the gene proximal to D9S287 (Farndon et al. (1994) *Genomics* 23: 486–489). The 9q22 region, however, is very gene rich and appeared to contain at least two tumor suppressor genes. In addition, Harshman et al. (1995) *Hum. Mol. Genet.* 4: 1259–1266, showed that different methods of identifying cDNAs from a genomic region result in a surprisingly different array of candidate genes. Thus, prior to this invention the specific NBCCS gene was unknown.

SUMMARY OF THE INVENTION

This invention provides for a nucleic acid sequence (e.g., a cDNA) associated with nevoid basal cell carcinoma syndrome (NBCCS) and with various cancers including various sporadic basal cell carcinomas (BCCs). The NBCCS gene disclosed herein appears to be a tumor-suppressor gene and is a homologue of the *Drosophila patched* (ptc) gene. The human NBCCS gene is therefore also referred to herein as the human PATCHED (PTC) gene.

Absence, partial inactivation (e.g., through haploinsufficiency or mutation), complete inactivation, or otherwise altered expression of the NBCCS (PTC) gene causes or creates a predisposition to NBCCS and/or to the onset of basal cell carcinomas.

In one preferred embodiment, this invention provides an isolated human nucleic acid encoding a nevoid basal cell carcinoma syndrome (NBCCS) (PTC) protein, wherein said nucleic acid specifically hybridizes, under stringent conditions, to a second nucleic acid consisting of a nucleic acid sequence selected from the group consisting of SEQ ID NOS. 1, 58 and 59, in the presence of a human genomic library under stringent conditions. The isolated nucleic acid is at least 30, preferably at least 50, more preferably at least 100, and most preferably at least 200 nucleotides in length.

In another embodiment, the isolated NBCCS nucleic acid has at least 75 percent sequence identity, preferably at least 85 percent, sequence identity, more preferably at least 90% sequence identity and most preferably at least 95 percent or even at least 98% sequence identity across a window of at least 30 nucleotides, preferably across a window of at least 50 nucleotides, more preferably across a window of at least 80 nucleotides, and most preferably across a window of at least 100 nucleotides, 200 nucleotides, 500 nucleotides or even the full length with the nucleic acid of SEQ ID NOS: 1, 58, or 59.

In one embodiment, the isolated human NBCCS nucleic acid is amplified from a genomic library using any of the primer pairs provided in Table 2. In another embodiment, the NBCCS nucleic acid is identified by specific hybridization with any of the nucleic acids amplified from a genomic library using any of the primer pairs provided in Table 2. In a particularly preferred embodiment the nucleic acid is a nucleic acid selected from the group consisting of SEQ ID NO: 1, SEQ ID NOS: 1, 58 and 59.

In another embodiment, this invention provides for an isolated human nevoid basal cell carcinoma syndrome (NBCCS) (PTC) nucleic acid sequence, wherein said nucleic acid encodes a polypeptide subsequence of at least 10 contiguous amino acid residues of the polypeptide encoded by a nucleic acid sequence selected from the group consisting of SEQ ID NOS: 1, 58 and 59, or conservative substitutions of said polypeptide subsequence. The isolated human NBCCS nucleic acid is preferably at least 50, more preferably at least 100, and most preferably at least 200, 400, 500, or even 800 residues (amino acids) in length. In a particularly preferred embodiment, the nucleic acid encodes a polypeptide sequence encoded by a nucleic acid selected from the group consisting of SEQ ID NO: 1, SEQ ID NO: 58, and SEQ. ID NO: 59. Even more preferably, the NBCCS nucleic acid is a nucleic acid selected from the group consisting of SEQ ID NOS: 1, 58 and 59.

In still yet another embodiment, this invention provides an isolated nucleic acid encoding a human nevoid basal cell carcinoma (NBCCS) (PTC) polypeptide comprising at least 10 contiguous amino acids from a polypeptide sequence encoded by a nucleic acid selected from the group consisting SEQ ID NOS: 1, 58 and 59, wherein: said polypeptide, when presented as an antigen, elicits the production of an antibody which specifically binds to a polypeptide sequence encoded by a nucleic acid selected from the group consisting of SEQ ID NOS: 1, 58 and 59, and said polypeptide does not bind to antisera raised against a polypetide encoded by a nucleic acid sequence selected from the group consisting of SEQ ID NOS: 1, 58 and 59 which has been fully immunosorbed with a polypeptide encoded by a nucleic acid sequence selected from the group consisting of SEQ ID NOS: 1, 58 and 59. Even more preferably this NBCCS nucleic acid hybridizes to a clone of the human PTC gene present in a human genomic library under stringent conditions and even more preferably hybridizes to a nucleic acid selected from the group consisting of SEQ ID NOS: 1, 58 and 59.

The invention also provides isolated nucleic acids that include one or more mutations compared to a nucleic acid selected from the group consisting of SEQ ID NOS: 1, 58 and 59. The mutations can be, for example, missense mutations, nonsense mutations, frameshift mutations, and splicing mutations. Alternatively, the mutations can be in regulatory regions that affect expression of the NBCCS gene.

In another embodiment, this invention provides for vectors incorporating any of the above-described nucleic acids. The vectors preferably include the above-described nucleic acid operably linked (under the control of) a promoter; either constitutive or inducible. The vector can also include an initiation and a termination codon.

This invention also provides for an isolated human NBCCS (PTC) polypeptide, said polypeptide comprising a subsequence of at least 10 contiguous amino acids of a polypeptide encoded by a nucleic acid selected from the group consisting of SEQ ID NOS: 1, 58 and 59, or conservative substitutions of said polypeptide subsequence. This NBCCS polypeptide is preferably at least 50, more preferably at least 100, and most preferably at least 200, 400, 500, or even 800 residues (amino acids) in length. The polypeptide can be a polypeptide encoded by a nucleic acid amplified from genomic DNA or an RNA using any of the primers pairs provided in Table 2. In a particularly preferred embodiment, the NBCCS polypeptide is a polypeptide encoded by a nucleic acid selected from the group consisting of SEQ ID NOS: 1, 58 and 59.

This invention also includes an isolated NBCCS (PTC) polypeptide comprising at least 10 contiguous amino acids from a polypeptide sequence encoded by a nucleic acid selected from the group consisting of SEQ ID NOS: 1, 58 and 59, wherein: said polypeptide, when presented as an antigen, elicits the production of an antibody which specifically binds to a polypeptide encoded by a nucleic acid selected from the group consisting of SEQ ID NOS: 1, 58 and 59, and said polypeptide does not bind to antisera raised against a polypeptide encoded by a nucleic acid sequence selected from the group consisting of SEQ ID NOS: 1, 58 and 59 which has been fully immunosorbed with a polypeptide encoded by a sequence selected from the group consisting of SEQ ID NOS: 1, 58 and 59. This polypeptide is preferably at least 50, more preferably at least 100, and most preferably at least 200, 400, 500, or even 800 amino acid residues in length. In a particularly preferred embodiment, this polypeptide is encoded by a nucleic acid selected from the group consisting of SEQ ID NOS: 1, 58 and 59.

The polypeptides of this invention can include conservative substitutions of any of the above-described polypeptides. In a particularly preferred embodiment the above-described nucleic acids and/or proteins, or subsequences thereof, are not a PTC nucleic acid or polypeptide from a Drosophila, a murine, or *C. elegans*.

In another embodiment, this invention provides for anti-NBCCS antibodies. Particularly preferred antibodies specifically bind a polypeptide comprising at least 10, more preferably at least 20, 40, 50, and most preferably at least 100, 200, 400, and even 800 contiguous amino acids, or even the full length polypeptide encoded by a nucleic acid selected from the group consisting of SEQ ID NOS: 1, 58 and 59 wherein: said polypeptide, when presented as an antigen, elicits the production of an antibody which specifically binds to a polypeptide encoded by a nucleic acid selected from the group consisting of SEQ ID NOS: 1, 58 and 59, and said polypeptide does not bind to antisera raised against a polypeptide encoded by a nucleic acid sequence selected from the group consisting of SEQ ID NOS: 1, 58 and 59 which has been fully immunosorbed with a polypeptide encoded by a nucleic acid sequence selected from the group consisting of SEQ ID NOS: 1, 58 and 59. The antibody can be polyclonal or monoclonal. The antibody can also be humanized or human.

This invention also provides for cells (e.g., recombinant cells such as hybridomas or triomas) expressing any of the above-described antibodies.

This invention also provides for methods of detecting a predisposition to nevoid basal cell carcinoma syndrome (NBCCS) or to a basal cell carcinoma. The methods include the steps of i) providing a biological sample of the organism; and ii) detecting a human NBCCS (PTC) gene or gene product in the sample. The provision of a biological sample and detection methods are described herein. In particular, detecting can involve detecting the presence or absence, or quantifying an NBCCS gene or subsequence thereof including any of the above-described nucleic acids. The detecting can also involve detecting the presence or absence or quantifying a NBCCS polypeptide or subsequence thereof including any of the above-described polypeptides. The detecting can involve detecting the presence or absence of normal or abnormal NBCCS nucleic acids or polypeptides. For example, one can detect a predisposition to BCC or NBCCS by detecting the presence of a mutation in a NBCCS nucleic acid. Particularly preferred assays include hybridization assays and/or sequencing for nucleic acids and immunoassays for NBCCS polypeptides.

In another embodiment, this invention provides for pharmacological compositions comprising a pharmaceutically acceptable carrier and a molecule selected from the group consisting of an vector encoding an NBCCS polypeptide or subsequence thereof, an NBCCS polypeptide or subsequence thereof, and an anti-NBCCS antibody as described herein.

This invention also provides for primers for the amplification of one or more exons of the NBCCS (PTC) gene. These primers include, but are not limited to the primers provided in Table 2.

This invention also provides kits for the detection and/or quantification of NBCCS gene or gene product. The kits can include a container containing one or more of any of the above identified nucleic acids, amplification primers, and antibodies with or without labels, free, or bound to a solid support as described herein. The kits can also include instructions for the use of one or more of these reagents in any of the assays described herein.

Finally, this invention also provides therapeutic methods. These include a methods of treating basal cell carcinoma and/or nevoid basal cell carcinoma syndrome and/or solar keratoses in a mammal. The methods can involve transfecting cells of the mammal with a vector expressing a nevoid basal cell carcinoma syndrome (NBCCS) polypeptide such that the cells express a functional NBCCS polypeptide as described herein. The transfection can be in vivo or ex vivo. Ex vivo transfection is preferably followed by re-infusion of the cells back into the organism as described herein. Other methods involve administering to the mammal a therapeutically effective dose of a composition comprising a NBCCS (PTC) polypeptide and a pharmacological excipient as described herein. The methods are preferably performed on mammals such as mice, rats, rabbits, sheep, goats, pigs, more preferably on primates including human patients.

Definitions

The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce $F(ab)'_2$ a dimer of Fab which itself is a light chain joined to $V_H$–$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, *Fundamental Immunology*, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

An "anti-NBCCs" antibody is an antibody or antibody fragment that specifically binds a polypeptide encoded by the NBCCS gene, cDNA, or subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that utilizes an antibody to specifically bind an analyte. The immunoassay is characterized by the use of specific binding properties of a particular antibody to isolate, target, and/or quantify the analyte.

The terms "isolated" "purified" or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, dioxigenin, or haptens and proteins for which antisera or monoclonal antibodies are available (e.g., the peptide of SEQ ID NO:1 can be made detectable, e.g., by incorporating a radio-label into the peptide, and used to detect antibodies specifically reactive with the peptide).

As used herein a "nucleic acid probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The term "target nucleic acid" refers to a nucleic acid (often derived from a biological sample), to which a nucleic acid probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

"Subsequence" refers to a sequence of nucleic acids or amino acids that comprise a part of a longer sequence of nucleic acids or amino acids (e.g., polypeptide) respectively.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

The term "identical" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol. Biol.* 48:443, by the search for similarity method of Pearson and Lipman (1988) *Proc. Natl. Acad. Sci. USA* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

An additional algorithm that is suitable for determining sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915–10919) alignments (B) of 50, expectation (E) of 10, M=5, N=−4, and a comparison of both strands.

The BLAST algorithm performs a statistical analysis of the similarity between two sequences; see, e.g., Karlin and Altschul (1993) *Proc. Nat'l. Acad. Sci. USA* 90: 5873–5787. One measure of similarity provided by the BLAST algorithm is the smallest sum probability (P(N)), which provides an indication of the probability by which a match between two nucleotide or amino acid sequences would occur by chance. For example, a nucleic acid is considered similar to an NBCCS gene or cDNA if the smallest sum probability in a comparison of the test nucleic acid to an NBCCS nucleic acid (e.g., SEQ ID NOS: 1, 58 or 59) is less than about 1, preferably less than about 0.1, more preferably less than about 0.01, and most preferably less than about 0.001.

The term "substantial identity" or "substantial similarity" in the context of a polypeptide indicates that a polypeptide comprises a sequence with at least 70% sequence identity to a reference sequence, or preferably 80%, or more preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

An indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual,* Cold Spring Harbor Publications, New York, for a description of immunoassay formats and conditions that can be used to determine specific immunoreactivity.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins,* W. H. Freeman and Company. In addition, individual substitutions, deletions or additions which alter, add or delete a single amino acid or a small percentage of amino acids in an encoded sequence are also "conservatively modified variations".

The terms human "PTC" or human "NBCCS gene or cDNA" are used interchangeably to refer to the human homologue of the *Drosophila patched* (ptc) gene disclosed herein. As explained below, the human PTC gene is a tumor suppressor gene also involved in the etiology of nevoid basal carcinoma cell syndrome.

A "gene product", as used herein, refers to a nucleic acid whose presence, absence, quantity, or nucleic acid sequence is indicative of a presence, absence, quantity, or nucleic acid composition of the gene. Gene products thus include, but are not limited to, an mRNA transcript, a cDNA reverse transcribed from an mRNA, an RNA transcribed from that cDNA, a DNA amplified from the cDNA, an RNA transcribed from the amplified DNA or subsequences of any of these nucleic acids. Polypeptides expressed by the gene or subsequences thereof are also gene products. The particular type of gene product will be evident from the context of the usage of the term.

An "abnormal PTC (or NBCCS) gene or cDNA" refers to a NBCCS gene or cDNA that encodes a non-functional NBCCS polypeptide, or an NBCCS polypeptide of substantially reduced functionality. Non-functional, or reduced functionality, NBCCS polypeptides are characterized by a predisposition (i.e., an increased likelihood as compared to the "normal" population) for, or the onset of, nevoid basal cell carcinoma syndrome. Similarly, "abnormal PTC (or NBCCS) gene product" refers to a nucleic acid encoding a non-functional or reduced functionality NBCCS polypeptide or the non-functional or reduced functionality NBCCS polypeptide itself. Abnormal NBCCS (PTC) genes or gene products include, for example, NBCCS genes or subsequences altered by mutations (e.g. insertions, deletions, point mutations, etc.), splicing errors, premature termination codons, missing initiators, etc. Abnormal NBCCS polypeptides include polypeptides expressed by abnormal NBCCS genes or nucleic acid gene products or subsequences thereof. Abnormal expression of NBCCS genes includes underexpression (as compared to the "normal" healthy population) of NBCCS e.g., through partial or complete inactivation, haploinsufficiency, etc.

BRIEF DESCRIPTION OF THE DRAWINGS

FIG. 5 shows a frameshift mutation of PTC in a sporadic NBCCS patient. (FIG. 5A) Both parents of an affected individual were free of phenotypic features of NBCCS. (FIG. 5B) Panels marked "1" and "2" show the sequences for the parents. The patient (panel marked "3") was heterozygous for a single stranded conformation polymorphism (SSCP) varient in Exon 12 that was not present in her parents, and sequencing of a PCR product from genomic DNA showed two sequences out of frame following base 2000. The abnormal conformer was sequenced (SEQ ID NO:56) and contained a 1 bp insertion resulting in a premature stop nine amino acids downstream. Sequences of PCR products from both parents were normal (SEQ ID NO: 57) (FIG. 5B, panels 1 and 2).

FIG. 6 shows an ultraviolet B-induced mutation of PTC in a sporadic basal cell carcinoma.

(FIG. 7A) A 14 bp deletion in the remaining allele of a tumor with allelic loss of the NBCCS region (SEQ ID NO:79). Despite the fact that this tumor was removed from the nose, a highly sunlight-exposed area, the mutation cannot be related specifically to ultraviolet radiation. (FIG. 7B) Constitutional DNA had the normal sequence (SEQ ID NO:80).

FIG. 8 shows the nucleotide sequence (SEQ ID NO:1) of the human PTC cDNA (Genbank Accession No. U43148). The sequence of PTC is shown, including the open reading frame and flanking 5' and 3' sequences. The corresponding amino acid sequence is presented in SEQ ID NO:60.

FIG. 9 shows mutations in the human PTC gene in DNA obtained from desmoplastic medulloblastomas D322, D292 and D86.

FIG. 10 shows PTC mRNA levels as determined using a semi-quantitative RT-PCR approach as described in Example 5. 250 ng of RNA in 10 µl was reverse transcribed in the presence of 40 pg of each of the standard RNAs with internal deletions for PTC, $\beta_2$-microglobin and GAPDH. The cDNAs were then amplified with primers for PTC and the housekeeping genes. The products were separated and quantitated on an ABI 373A sequencer. The expression level of the three genes were determined as the ratio of signals of the sample (right peaks) to the specific standards (left peaks).

FIG. 12 shows a section of the NBCCS gene containing exons 1, 1a, and 1b. Sites of forward ("F") and reverse ("R") primers 18 and 22 are indicated, as are the start and end of exon 1 and the end of exon 1a.

FIG. 13 shows a section of the NBCCS gene containing exon 2a. The start and end points of the exon are shown, along with the locations of primers PTCXF1 and PTCXR1, respectively.

DETAILED DESCRIPTION

Figure 1:
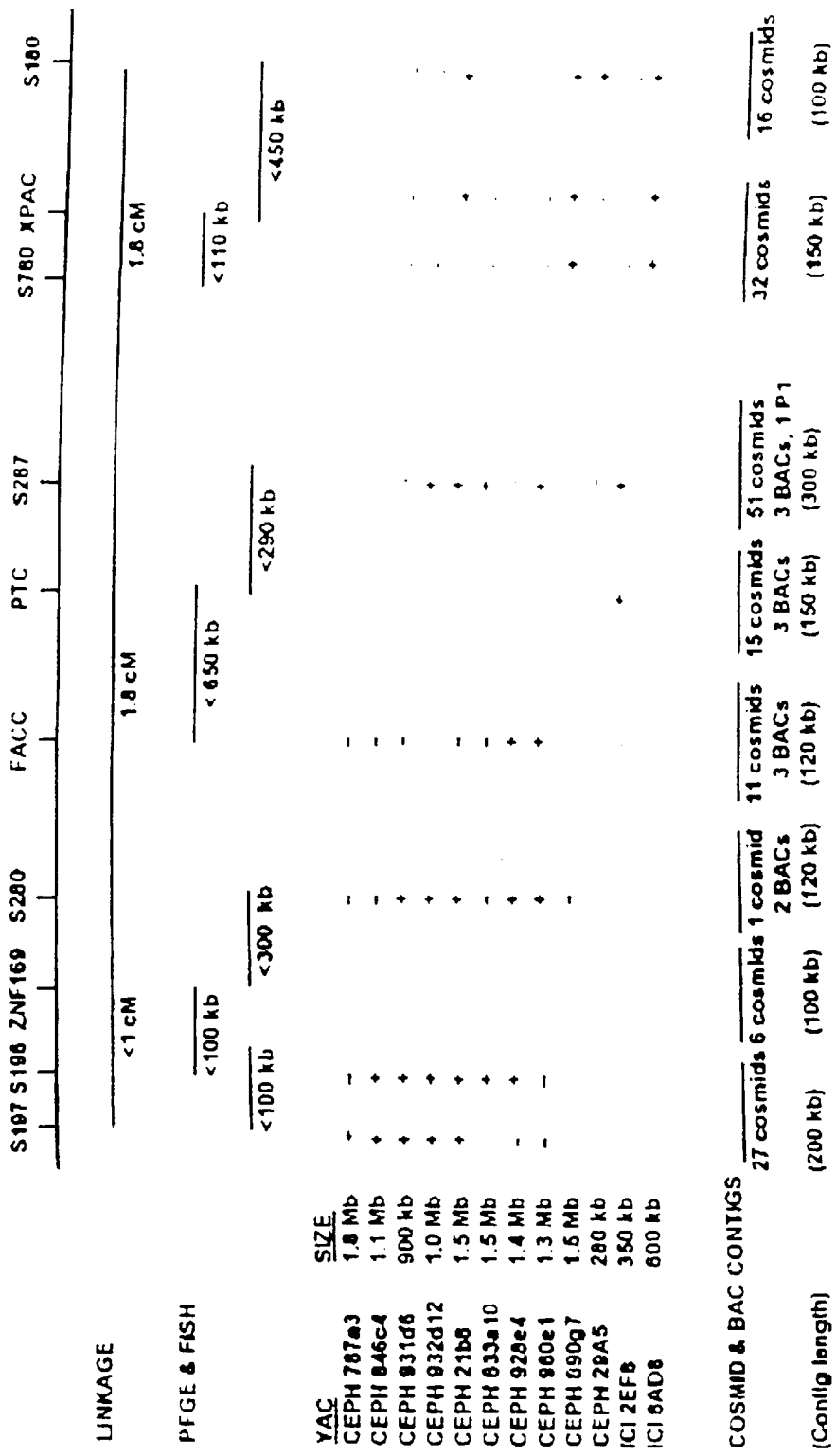
FIG. 1 shows an integrated framework map of the NBCCS region. Both linkage and tumor deletion studies place NBCCS between D9S196 and D9S180 but are conflicting, with regard to whether the gene lies proximal or distal to D9S287. The order of six polymorphic markers, D9S197, D9S196-D9S280-FACC-D9S287-D9S180, is derived from genetic linkage data (Farndon et al., 1994; Pericak-Vance et al., 1995). D9S196 and D9S197 show no measurable recombination. Pulsed-field gel electrophoresis (PFGE) and FISH give a minimum distance of 2 Mb between D9S196 and D9S180. Key information about YAC, BAC, and cosmid contigs in the NBCCS region is shown. In total, 22 overlapping YACs and more than 800 cosmids were isolated from this region. BAC and cosmid contigs covering more than 1.2 Mb have been submitted to the Genome Data Base.

This invention pertains to the discovery of a tumor suppressor gene associated with the etiology of nevoid basal cell carcinoma syndrome. In addition, this invention pertains to the discovery that various cancers, including sporadic basal cell carcinomas (BCCs) can arise with somatic loss of both copies of the same gene.

Nevoid basal cell carcinoma syndrome, also known as Gorlin syndrome and the basal cell nevus syndrome, is an autosomal dominant disorder that predisposes to both cancer and developmental defects (Gorlin (1995) Dermatologic Clinics, 13: 113–125). Its prevalence has been estimated at 1 per 56,000, and 1–2% of medulloblastomas and 0.5% of basal cell carcinomas (BCCS) are attributable to the syndrome (Springate (1986) J. Pediatr. Surg. 21: 908–910; Evans et al. (1991) British J. Cancer., 64: 959–961). In addition to basal cell carcinomas (BCCs) and medulloblastomas, NBCCS patients are also at an increased risk for ovarian fibromas, meningiomas, fibrosarcomas, rhabdomyosarcomas, cardiac fibromas and ovarian dermoids (Evans et al. (1991) supra., Evans et al. (1993) J. Med. Genet. 30: 460–464; Gorlin (1995) supra.).

Implications for the affected individual can be severe, predominantly due to the prolific basal cell carcinomas which can number more than 500 in a lifetime (Shanley et al. (1994) supra). Expression of many features of the syndrome is variable, but the severity tends to breed true within families (Anderson et al. (1967) Am. J. Hum. Genet., 19: 12–22). This variation between families may reflect specific phenotypic effects of different mutations, modifier genes, or environmental factors (sunlight exposure is likely to play a role in the age of onset and incidence of basal cell carcinomas). One third to one half of patients have no affected relatives and are presumed to be the product of new germ cell mutations (Gorlin (1995) supra.). Unilateral and segmental NBCCS are attributed to somatic mutation in one cell of an early embryo (Gutierrez and Mora, (1986) supra.)

I. Uses of the NBCCS (PTC) cDNA.

As indicated above, the NBCCS gene of this invention is a tumor suppressor gene. Defects in the expression of this gene are associated the onset of various cancers, particularly with sporadic basal cell carcinoma in somatic cells. Heritable defects in the expression of the NBCCS gene are a causal factor in the etiology of NBCCS and its attendant developmental abnormalities (see example 2, below).

While basal cell carcinomas and many features of NBCCS are believed to be due to homozygous inactivation of PTC generalized or symmetric features such as overgrowth, macrocephaly, and facial dysmorphology are believed to be due to haploinsufficiency or other mechanisms of partial gene inactivation.

Clearly, detection of defective NBCCS (PTC) gene expression is of clinical value. The presence of an NBCCS (PTC) gene, cDNA, mRNA, protein, or subsequence of the gene, cDNA, or protein in a biological sample is useful, e.g., as a marker to assess in vivo and/or in situ RNA transcription and/or translation, in cancer diagnostics (as in the detection or verification of basal cell carcinoma), in prophpylaxis for NBCCS or BCC as an indication of a heritable predilection for NBCCS or BCC, or in DNA forensic analysis such as DNA fingerprinting. Full-length NBCCS cDNA, individual exons, or subsequences thereof are also useful as probes (particularly when labeled) for the detection of the presence or absence and/or quantitation of normal or abnormal (e.g., truncated or mutated) NBCCS (PTC) DNA or RNA in a biological sample. The labeled probes can also be useful as in fluorescent karyotyping analysis as markers of the NBCCS gene. Because the NBCCS cDNA or subsequences thereof is shown herein to map to human chromosome 9q22.3, one of skill can use the gene, cDNA, or subsequences, as a probe to assess whether there are any gross chromosomal abnormalities in this region of chromosome 9. This is useful, for instance, in in utero screening of a fetus to monitor for the presence of chromosomal abnormalities in particular for a predilection of NBCCS or basal cell carcinomas.

Similarly, the proteins encoded by the NBCCS cDNA can be used as diagnostic markers for NBCCS and/or basal cell carcinomas. The proteins or subsequences thereof can also be used as antigens for raising anti-NBCCS protein antibodies. The antibodies are useful for immunoassays for the detection of normal or abnormal expression of NBCCS proteins, and for the isolation of NBCCS polypeptides (as with affinity chromatography).

Vectors encoding the NBCCS proteins are useful for expressing those proteins to provide immunogens for antibody production. Vectors encoding the NBCCS proteins are also useful for transforming cells in vitro or in vivo to express NBCCS proteins. In vivo transformation of cells to express heterologous NBCCS genes can be used to offset deficient expression of the NBCCS protein.

Cells and/or tissues expressing the NBCCS (PTC) gene may be used to monitor expression levels of NBCCS polypeptides in a wide variety of contexts. For example, where the effects of a drug on NBCCS expression is to be determined the drug will be administered to the transformed (to express NBCCS) organism, tissue, or cell. Expression levels, or expression products will be assayed as described below and the results compared results from to organisms, tissues, or cells similarly treated, but without the drug being tested.

II. The NBCCS (PTC) Gene

A) The Human PTC Gene

SEQ ID NO:1 provides nucleic acid and SEQ ID NO:60 provides polypeptide sequences for the human PTC cDNA of this invention. The sequence of human PTC, as shown, consists of an open reading frame of 3888 nucleotides flanked by 441 and 2240 nucleotides on the 5' end and on the 3' end, respectively (SEQ ID NO: 1, FIG. 8). The open reading frame of human PTC cDNA encodes for a putative protein of 1296 amino acids. The open reading frame starts with an ATG codon that has a moderate match for the translational start consensus sequence in vertebrates (GAGGCTATGT (SEQ ID NO: 6) in PTC versus GCCGC-CATGG (SEQ ID NO: 7) (Kozak (1991) *J. Biol. Chem.* 266: 19867–19870)). This codon codes for the first amino acid of one human form of the PTC protein consisting of 1296 amino acids with a relative molecular weight ($M_r$) of $131 \times 10^3$. It shows 61% sequence identity to its Drosophila counterpart. The open reading frame extends an additional 354 nucleotides upstream of the ATG codon (starting at base pair 88 of the sequence shown in FIG. 8). The 3' untranslated region contains a canonical polyadenylation signal (AATAAA (SEQ ID NO: 8)) as well as mRNA destabilizing (ATTTA (SEQ ID NO: 9)) motifs. These are localized 1031 nucleotides and 175, 371, and 1143 nucleotides after the termination codon, respectively. A second human PTC protein contains an open reading frame that continues right through to the 5' end, and may be initiated by upstream sequences.

B) Isolation of cDNA and/or Probes

The nucleic acids (e.g., NBCCS cDNA, or subsequences (probes)) of the present invention are cloned, or amplified by in vitro methods, such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017, 478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077–1080; Van Brunt (1990) *Biotechnology*, 8: 291–294; Wu and Wallace, (1989) *Gene*, 4: 560; and Barringer et al. (1990) *Gene*, 89: 117.

In one preferred embodiment, the human NBCCS (PTC) cDNA can be isolated by routine cloning methods. The cDNA sequence provided in SEQ ID NO: 1 can be used to provide probes that specifically hybridize to the NBCCS gene, in a genomic DNA sample, or to the NBCCS mRNA, in a total RNA sample (e.g., in a Southern blot). Once the target NBCCS nucleic acid is identified (e.g., in a Southern blot), it can be isolated according to standard methods known to those of skill in the art (see, e.g., Sambrook et al. (1989) *Molecular Cloning: A Laboratory Manual, 2nd Ed.,* Vols. 1–3, Cold Spring Harbor Laboratory; Berger and Kimmel (1987) *Methods in Enzymology, Vol.* 152: *Guide to Molecular Cloning Techniques,* San Diego: Academic Press, Inc.; or Ausubel et al. (1987) *Current Protocols in Molecular Biology,* Greene Publishing and Wiley-Interscience, New York). Methods of screening human cDNA libraries for the NBCCS gene are provided in Example 1.

In another preferred embodiment, the human PTC cDNA can be isolated by amplification methods such as polymerase chain reaction (PCR). Table 2 provides primers suitable for the amplification of all 21 exons of the cDNA. In addition, appropriate PCR protocols are provided in Example 2.

C) Labeling of Nucleic Acid Probes

Where the NBCCS cDNA or its subsequences are to be used as nucleic acid probes, it is often desirable to label the sequences with detectable labels. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In another preferred embodiment, transcription amplification using a labeled nucleotide (e.g. fluorescein-labeled UTP and/or CTP) incorporates a label into the transcribed nucleic acids.

Alternatively, a label may be added directly to an original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

III. Antibodies to the NBCCS Polypeptide(s)

Antibodies are raised to the NBCCS polypeptides of the present invention, including individual, allelic, strain, or species variants, and fragments thereof, both in their naturally occurring (full-length) forms and in recombinant forms. Additionally, antibodies are raised to these polypeptides in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A) Antibody Production

A number of immunogens are used to produce antibodies specifically reactive with NBCCS polypeptides. Recombinant or synthetic polypeptides of 10 amino acids in length, or greater, selected from amino acid sub-sequences of SEQ ID NO 1 are the preferred polypeptide immunogen (antigen) for the production of monoclonal or polyclonal antibodies. In one class of preferred embodiments, an immunogenic peptide conjugate is also included as an immunogen. Naturally occurring polypeptides are also used either in pure or impure form.

Recombinant polypeptides are expressed in eukaryotic or prokaryotic cells (as described below) and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen (antigen), preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired (see, e.g., Coligan (1991) *Current Protocols in Immunology* Wiley/Greene, NY; and Harlow and Lane (1989) *Antibodies: A Laboratory Manual* Cold Spring Harbor Press, NY).

Antibodies, including binding fragments and single chain recombinant versions thereof, against predetermined fragments of NBCCS polypeptides are raised by immunizing animals, e.g., with conjugates of the fragments with carrier proteins as described above. Typically, the immunogen of interest is a peptide of at least about 5 amino acids, more typically the peptide is 10 amino acids in length, preferably, the fragment is 15 amino acids in length and more preferably the fragment is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. These antibodies are screened for binding to normal or modified polypeptides, or screened for agonistic or antagonistic activity, e.g., activity mediated through a NBCCS protein. Specific monoclonal and polyclonal antibodies will usually bind with a $K_D$ of at least about 0.1 mM, more usually at least about 50 $\mu$M, and most preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314).

Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of this invention are also used for affinity chromatography in isolating NBCCS polypeptides. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified NBCCS polypeptides are released.

The antibodies can be used to screen expression libraries for particular expression products such as normal or abnormal human NBCCS protein. Usually the antibodies in such a procedure are labeled with a moiety allowing easy detection of presence of antigen by antibody binding.

Antibodies raised against NBCCS polypeptides can also be used to raise antiidiotypic antibodies. These are useful for detecting or diagnosing various pathological conditions related to the presence of the respective antigens.

B) Human or Humanized (Chimeric) Antibody Production

The anti-NBCCS antibodies of this invention can also be administered to an organism (e.g., a human patient) for therapeutic purposes (e.g., to block the action an NBCCS polypeptide or as targeting molecules when conjugated or fused to effector molecules such as labels, cytotoxins, enzymes, growth factors, drugs, etc.). Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

i) Humanized (chimeric) antibodies.

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding (e.g., anti-NBCCS polypeptide) specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472, 693, 5,354,847, 5,292,867, 5,231,026, 5,204,244, 5,202,238, 5,169,939, 5,081,235, 5,075,431, and 4,975,369).

In general, the procedures used to produce these chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains (or simply as the V or Variable region) may be in either the cDNA or genomic form; (b) cloning the gene segments encoding the constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature*, 312: 643; and anti-tumor antigens: Sahagan et al. (1986) *J. Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565–3567).

In one preferred embodiment, a recombinant DNA vector is used to transfect a cell line that produces an anti-NBCCS antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" which allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an anti-NBCCS antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA which encodes a modification for a monoclonal antibody can be targeted directly to the site of the expressed immunoglobulin gene within a B-cell or hybridoma cell line. DNA constructs for any particular modification may be used to alter the protein product of any monoclonal cell line or hybridoma. Such a procedure circumvents the costly and time consuming task of cloning both heavy and light chain variable region genes from each B-cell clone expressing a useful antigen specificity. In addition to circumventing the process of cloning variable region genes, the level of expression of chimeric antibody should be higher when the gene is at its natural chromosomal location rather than at a random position. Detailed methods for preparation of chimeric (humanized) antibodies can be found in U.S. Pat. No. 5,482,856.

ii) Human antibodies.

In another embodiment, this invention provides for fully human anti-NBCCS antibodies. Human antibodies consist entirely of characteristically human polypeptide sequences. The human anti-NBCCS antibodies of this invention can be produced in using a wide variety of methods (see, e.g., Larrick et al., U.S. Pat. No. 5,001,065, for review).

In one preferred embodiment, the human anti-NBCCS antibodies of the present invention are usually produced initially in trioma cells. Genes encoding the antibodies are then cloned and expressed in other cells, particularly, non-human mammalian cells.

The general approach for producing human antibodies by trioma technology has been described by Ostberg et al. (1983) *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmunized human peripheral B lymphocytes. This fusion generates a xenogenic hybrid cell containing both human and mouse chromosomes (see, Engelman, supra.). Xenogenic cells that have lost the capacity to secrete antibodies are selected. Preferably, a xenogenic cell is selected that is resistant to 8-azaguanine. Cells possessing resistance to 8-azaguanine are unable to propagate on hypoxanthine-aminopterin-thymidine (HAT) or azaserine-hypoxanthine (AH) media.

The capacity to secrete antibodies is conferred by a further fusion between the xenogenic cell and B-lymphocytes immunized against an NBCCS polypeptide or an epitope thereof. The B-lymphocytes are obtained from the spleen, blood or lymph nodes of human donor. If antibodies against a specific antigen or epitope are desired, it is preferable to use that antigen or epitope thereof as the immunogen rather than NBCCS polypeptide. Alternatively, B-lymphocytes are obtained from an unimmunized individual and stimulated with an NBCCS polypeptide, or a epitope thereof, in vitro. In a further variation, B-lymphocytes are obtained from an infected, or otherwise immunized individual, and then hyperimmunized by exposure to an NBCCS polypeptide for about seven to fourteen days, in vitro.

The immunized B-lymphocytes prepared by one of the above procedures are fused with a xenogenic hybrid cell by well known methods. For example, the cells are treated with 40–50% polyethylene glycol of MW 1000–4000, at about 37° C. for about 5–10 min. Cells are separated from the fusion mixture and propagated in media selective for the desired hybrids. When the xenogenic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to an NBCCS polypeptide or an epitope thereof. Triomas producing human antibodies having the desired specificity are subcloned by the limiting dilution technique and grown in vitro in culture medium, or are injected into selected host animals and grown in vivo.

The trioma cell lines obtained are then tested for the ability to bind an NBCCS polypeptide or an epitope thereof. Antibodies are separated from the resulting culture medium or body fluids by conventional antibody-fractionation procedures, such as ammonium sulfate precipitation, DEAE cellulose chromatography and affinity chromatography.

Although triomas are genetically stable they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the especially extensive viral screening required for human cell lines.

The genes encoding the heavy and light chains of immunoglobulins secreted by trioma cell lines are cloned according to methods, including the polymerase chain reaction, known in the art (see, e.g., Sambrook et al., *Molecular Cloning: A Laboratory Manual,* 2nd ed., Cold Spring Harbor, N.Y., 1989; Berger & Kimmel, *Methods in Enzymology, Vol.* 152: *Guide to Molecular Cloning Techniques,* Academic Press, Inc., San Diego, Calif., 1987; Co et al. (1992) *J. Immunol.,* 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al. (1987) *Sequences of Proteins of Immunological Interest,* U.S. Department of Health and Human Services.

In addition to the DNA segments encoding anti-NBCCS immunoglobulins or fragments thereof, other substantially homologous modified immunoglobulins can be readily designed and manufactured utilizing various recombinant DNA techniques known to those skilled in the art such as site-directed mutagenesis (see Gillman & Smith (1979) *Gene,* 8: 81–97; Roberts et al. (1987) *Nature* 328: 731–734). Such modified segments will usually retain antigen binding capacity and/or effector function. Moreover, the modified segments are usually not so far changed from the original trioma genomic sequences to prevent hybridization to these sequences under stringent conditions. Because, like many genes, immunoglobulin genes contain separate functional regions, each having one or more distinct biological activities, the genes may be fused to functional regions from other genes to produce fusion proteins (e.g., immunotoxins) having novel properties or novel combinations of properties.

The recombinant polynucleotide constructs will typically include an expression control sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the human anti-NBCCS immunoglobulins.

These expression vectors are typically replicable in the host organisms either as episomes or as an integral part of the host chromosomal DNA. Commonly, expression vectors will contain selection markers, e.g., ampicillin-resistance or hygromycin-resistance, to permit detection of those cells transformed with the desired DNA sequences.

In general, prokaryotes can be used for cloning the DNA sequences encoding a human anti-NBCCS immunoglobulin chain. *E. coli* is one prokaryotic host particularly useful for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utilization.

Mammalian cells are a particularly preferred host for expressing nucleotide segments encoding immunoglobulins or fragments thereof (see, e.g., Winnacker, *From Genes to Clones,* VCH Publishers, N.Y., 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al. (1986) *Immunol. Rev.* 89: 49), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like (see, e.g., Co et al. (1992) *J. Immunol.* 148: 1149).

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see, generally, Sambrook et al., supra).

Once expressed, human anti-NBCCS immunoglobulins of the invention can be purified according to standard procedures of the art, including HPLC purification, fraction column chromatography, gel electrophoresis and the like (see, generally, Scopes, *Protein Purification,* Springer-Verlag, NY, 1982). Detailed protocols for the production of human antibodies can be found in U.S. Pat. No. 5,506,132.

Other approaches in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas which produces human anti-NBCCS are prepared (see, e.g., U.S. Pat. No. 5,506,132). Other approaches include immunization of murines transformed to express human immunoglobulin genes, and phage display screening (Vaughan et al. supra.).

IV. Expression of NBCCS Polypeptides

A) De novo Chemical Synthesis

The NBCCs proteins or subsequences thereof may be synthesized using standard chemical peptide synthesis techniques. Where the desired subsequences are relatively short (e.g., when a particular antigenic determinant is desired) the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis;* pp. 3–284 in *The Peptides: Analysis, Synthesis, Biology. Vol.* 2: *Special Methods in Peptide Synthesis, Part A.,* Merrifield, et al. *J. Am. Chem. Soc.,* 85: 2149–2156 (1963), and Stewart et al., *Solid Phase Peptide Synthesis, 2nd ed.* Pierce Chem. Co., Rockford, Ill. (1984).

B) Recombinant Expression

In a preferred embodiment, the NBCCS proteins or subsequences thereof, are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the NBCCS proteins or subsequences of this invention may be prepared by any suitable method as described above, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, NBCCS proteins of this invention may be cloned using DNA amplification methods such as polymerase chain reaction (PCR). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired NBCCS sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the Sequence information provided in SEQ ID NO: 1. Appropriate restriction sites can also be added to the nucleic acid encoding the NBCCS protein or protein subsequence by site-directed mutagenesis. The plasmid containing the NBCCS sequence or subsequence is cleaved with the appropriate restriction endonuclease and then ligated into the vector encoding the second molecule according to standard methods.

The nucleic acid sequences encoding NBCCS proteins or protein subsequences may be expressed in a variety of host cells, including *E. coli,* other bacterial hosts, yeast, and various higher eukaryotic cells such as the COS, CHO and HeLa cells lines and myeloma cell lines. As the NBCCS proteins are typically found in eukaryotes, a eukaryote host is preferred. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant NBCCS proteins can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol.* 182: *Guide to Protein Purification.,* Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g, as immunogens for antibody production).

One of skill in the art would recognize that after chemical synthesis, biological expression, or purification, the NBCCS protein(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.,* 268: 14065–14070; Kreitman and Pastan (1993) *Bioconjug. Chem.,* 4: 581–585; and Buchner, et al., (1992) *Anal. Biochem.,* 205: 263–270). Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the NBCCS proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

V. Detection of NBCCS

As indicated above, abnormal (e.g., altered or deficient) expression of the human PTC gene is a causal factor in the development of basal cell carcinomas and, where the alteration is a heritable character, in the etiology of nevoid basal cell carcinoma syndrome and/or the various developmental abnormalities characteristic of this syndrome. It is believed that development of neoplasia requires complete inactivation of the NBCCS gene, however, partial inactivation creates a predisposition, either through haploinsufficiency or through increased susceptibility to complete inactivation (e.g., through a second mutation), to basal cell carcinomas and/or NBCCS.

Thus, it is desirable to determine the presence or absence, or quantify, the expression of NBCCS polypeptides of the nucleic acids encoding the NBCCS polypeptides. This may be accomplished by assaying the gene product; NBCCS polypeptides themselves, or alternatively, by assaying the nucleic acids (DNA or mRNA) that encode the NBCCS polypeptides. In particular, it is desirable to determine whether NBCCS expression is present, absent, or abnormal (e.g. because of an abnormal gene product or because of abnormal expression levels as, for example, with a hemizygous gene). Particularly, where it is desired to determine a heritable propensity for abnormal NBCCS gene expression, it is preferred to assay the host DNA for abnormal NBCCS genes or gene transcripts (mRNAs).

A) Sample Collection and Processing

The NBCCS (PTC) gene or gene product (i.e., mRNA or polypeptide) is preferably detected and/or quantified in a biological sample. As used herein, a biological sample is a sample of biological tissue or fluid that, in a healthy and/or pathological state, contains an NBCCS (PTC) nucleic acid or polypeptide. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect NBCCS genes or gene products in samples from any mammal, such as dogs, cats, sheep, cattle, and pigs.

The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

B) Nucleic Acid Assays

In one embodiment, this invention provides for methods of detecting and/or quantifying human NBCCS (PTC) expression by assaying the underlying NBCCS gene (or a fragment thereof) or by assaying the NBCCS gene transcript (mRNA). The assay can be for the presence or absence of the normal gene or gene product, for the presence or absence of an abnormal gene or gene product, or quantification of the transcription levels of normal or abnormal NBCCS gene product.

i) Nucleic acid sample.

In a preferred embodiment, nucleic acid assays are performed with a sample of nucleic acid isolated from the organism to be tested. In the simplest embodiment, such a nucleic acid sample is the total mRNA isolated from a biological sample. The nucleic acid (e.g., either genomic DNA or mRNA) may be isolated from the sample according to any of a number of methods well known to those of skill in the art. One of skill will appreciate that where alterations in the copy number of the NBCCS gene are to be detected genomic DNA is preferably isolated. Conversely, where expression levels of a gene or genes are to be detected, preferably RNA (mRNA) is isolated.

Methods of isolating total DNA or mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993)).

In a preferred embodiment, the total nucleic acid is isolated from a given sample using, for example, an acid guanidinium-phenol-chloroform extraction method and polyA$^+$ mRNA is isolated by oligo dT column chromatography or by using (dT)n magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis et al. (1990) *PCR Protocols. A guide to Methods and Application.* Academic Press, Inc. San Diego), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), and self-sustained sequence replication (Guatelli et al. (1990) *Proc. Nat. Acad. Sci. USA* 87:1874).

ii) Hybridization assays.

A variety of methods for specific DNA and RNA measurement using nucleic acid hybridization techniques are known to those of skill in the art (see Sambrook et al. supra). For example, one method for evaluating the presence, absence, or quantity of DNA encoding NBCCS proteins in a sample involves a Southern transfer. Briefly, the digested genomic DNA is run on agarose slab gels in buffer and transferred to membranes.

Hybridization is carried out using the nucleic acid probes specific for the target NBCCS sequence or subsequence.

Nucleic acid probes are designed based on the nucleic acid sequences encoding NBCCCS proteins (see SEQ ID NO: 1). The probes can be full length or less than the full length of the nucleic acid sequence encoding the NBCCS protein. Shorter probes are empirically tested for specificity. Preferably nucleic acid probes are 20 bases or longer in length. (See Sambrook et al. for methods of selecting nucleic acid probe sequences for use in nucleic acid hybridization.) Visualization of the hybridized portions allows the qualitative determination of the presence or absence of DNA encoding NBCCS proteins.

Similarly, a Northern transfer may be used for the detection of mRNA encoding NBCCS proteins. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of NBCCS proteins.

A variety of nucleic acid hybridization formats are known to those skilled in the art. For example, common formats include sandwich assays and competition or displacement assays. Hybridization techniques are generally described in "*Nucleic Acid Hybridization, A Practical Approach*," Ed. Hames, B. D. and Higgins, S. J., IRL Press, (1985); Gall and Pardue *Proc. Natl. Acad Sci. U.S.A.* 63: 378–383 (1969); and John et al. *Nature* 223: 582–587 (1969).

For example, sandwich assays are commercially useful hybridization assays for detecting or isolating nucleic acid sequences. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands which bind to labeled antibodies, fluorophores, chemiluminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, P., "Practice and Theory of Enzyme Immunoassays," *Laboratory Techniques in Biochemistry and Molecular Biology,* Burdon, R. H., van Knippenberg, P. H., Eds., Elsevier (1985), pp. 9–20.).

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for determining the level of expression of a gene encoding an NBCCS protein is in situ hybridization. In situ hybridization assays are well known and are generally described in Angerer, et al., *Methods Enzymol.,* 152: 649–660 (1987). In an in situ hybridization assay, cells or tissue specimens are fixed to a solid support, typically a glass slide. If DNA is to be probed, the cells are denatured with heat or alkali. The cells are then contacted with a hybridization solution at a moderate temperature to permit annealing of labeled probes specific to NBCCS proteins. The probes are preferably labeled with radioisotopes or fluorescent reporters. Detection of NBCCS by in situ hybridization is detailed in Example 2.

iii) Amplification based assays.

In another embodiment, the NBCCS gene or gene product can be detected (assayed) using an amplification based assay. In an amplification based assay, all or part of the NBCCS gene or transcript (e.g., mRNA or cDNA) is amplified and the amplification product is then detected. Where there is no underlying gene or gene product to act as a template amplification is non-specific or non-existent and there is no single amplification product. Where the underlying gene or gene product is present, the target sequence is amplified providing an indication of the presence, absence, or quantity of the underlying gene or mRNA.

Amplification-based assays are well known to those of skill in the art (see, e.g., Innis, supra.). The cDNA sequence provided for the NBCCS gene is sufficient to enable one of skill to routinely select primers to amplify any portion of the gene. In addition, Table 2 provides primer pairs for the PCR amplification of each of the 21 exons comprising the NBCCS (PTC) gene. Example 2, below, provides amplification protocols and illustrates detection of the NBCCS (PTC) gene using PCR.

Amplification primers can be selected to provide amplification products that span specific deletions, truncations, and insertions, as discussed below (see, Section iv, below) thereby facilitating the detection of specific abnormalities.

iv) Specific detection of abnormalities (eg., mutations).

Abnormal NBCCS (PTC) genes or gene products are characterized by premature stop codons, deletions, or insertions. Typical abnormal genes (PTC mutations) are illustrated in Tables 3, 5, 6, 7 and 9. Premature stop codons and deletions can be detected by decreased size of the gene or gene product (mRNA transcript or cDNA). Similarly, insertions can be detected by increased size of the gene or gene product. Alternatively, mutations can be determined by sequencing of the gene or gene product according to standard methods.

In addition, amplification assays and hybridization probes can be selected to specifically target particular abnormalities. For example, where the abnormality is a deletion, nucleic acid probes or amplification primers can be selected that specifically hybridize to or amplify, respectively, the nucleic acid sequence that is deleted in the abnormal gene. The probe will fail to hybridize, or the amplification reaction will fail to provide specific amplification, to abnormal versions of the NBCCS (PTC) nucleic acids which have the deletion. Alternatively, the probe or amplification reaction can be designed to span the entire deletion or either end of the deletion (deletion junction). Similarly, probes and amplification primers can be selected that specifically target point mutations or insertions. Methods for detecting specific mutations were described in, for example, U.S. Pat. No. 5,512,441. In the case of PCR, amplification primers can be designed to hybridize to a portion of the NBCCS (PTC) gene but the terminal nucleotide at the 3' end of the primer can be used to discriminate between the mutant and wild-type forms of NBCCS (PTC) gene. If the terminal base matches the point mutation or the wild-type sequence, polymerase dependent extension can proceed and an amplification product is detected. This method for detecting point mutations or polymorphisms was described in detail by Sommer et al., (1989) *Mayo Clin. Proc.* 64:1361–1372. By using appropriate controls, one can develop a kit having both positive and negative amplification products. The products can be detected using specific probes or by simply detecting their presence or absence. A variation of the PCR method uses LCR where the point of discrimination, i.e., either the point mutation or the wild-type bases fall between the LCR oligonucleotides. The ligation of the oligonucleotides becomes the means for discriminating between the mutant and wild-type forms of the NBCCS (PTC) gene.

A variety of automated solid-phase detection techniques are also appropriate for detecting the presence or absence of mutations in the NBCCS (PTC) gene. For instance, very large scale immobilized polymer arrays (VLSIPS™), available from Affymetrix, Inc. in Santa Clara, Calif. are used for the detection of nucleic acids having specific sequences of interest. See, Fodor et al. (1991) *Science*, 251: 767–777; Sheldon et al. (1993) *Clinical Chemistry* 39(4): 718–719, and Kozal et al. (1996) *Nature Medicine* 2(7): 753–759. For example, oligonucleotides that hybridize to all known NBCCS (PTC) mutations can be synthesized on a DNA chip (such chips are available from Affymetrix) and the nucleic acids from samples hybridized to the chip for simultaneous analysis of the sample nucleic acid for the presence or absence of any of the known NBCCS (PTC) mutations. Protocols for detecting mutations are also described in, for example, Tijssen (1993) *Laboratory Techniques in biochemistry and molecular biology—hybridization with nucleic acid probes parts I and II*, Elsevier, N.Y., and Choo (ed) (1994) *Methods In Molecular Biology* Volume 33- *In Situ Hybridization Protocols*, Humana Press Inc., New Jersey (see also, other books in the *Methods in Molecular Biology* series).

iv) Detection of expression levels.

Where it is desired to quantify the transcription level (and thereby expression) of a normal or mutated NBCCS genes in a sample, the nucleic acid sample is one in which the concentration of the mRNA transcript(s) of the NBCCS gene, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired, no elaborate control or calibration is required.

C) NBCCS Polypeptide Assays

The expression of the human NBCCS (PTC) gene can also be detected and/or quantified by detecting or quantifying the expressed NBCCS polypeptide. The NBCCS polypeptides can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay(RIA), enzyme-linked immunosorbent assays (ELISAs), immunofluorescent assays, western blotting, and the like.

In a particularly preferred embodiment, the NBCCS polypeptides are detected in an electrophoretic protein separation, more preferably in a two-dimensional electrophoresis, while in a most preferred embodiment, the NBCCS polypeptides are detected using an immunoassay.

As used herein, an immunoassay is an assay that utilizes an antibody to specifically bind to the analyte (NBCCS polypeptide). The immunoassay is thus characterized by detection of specific binding of a NBCCS polypeptide to an anti-NBCCS antibody as opposed to the use of other physical or chemical properties to isolate, target, and quantify the analyte.

1) Electrophoretic Assays.

As indicated above, the presence or absence of NBCCS polypeptides in a biological sample can be determined using electrophoretic methods. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol.* 182: *Guide to Protein Purification.*, Academic Press, Inc., N.Y.).

2) Immunological Binding Assays.

In a preferred embodiment, the NBCCS polypeptides are detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume* 37: *Antibodies in Cell Biology*, Asai, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte (in this case NBCCS polypeptide or subsequence). The capture agent is a moiety that specifically binds to the analyte. In a preferred embodiment, the capture agent is an antibody that specifically binds NBCCS polypeptide(s). The antibody (anti-NBCCS) may be produced by any of a number of means well known to those of skill in the art as described above in Section III(A).

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled NBCCS polypeptide or a labeled anti-NBCCS antibody. Alternatively, the labeling agent may be a third moiety, such as another antibody, that specifically binds to the antibody/NBCCS complex.

In a preferred embodiment, the labeling agent is a second human NBCCS antibody bearing a label. Alternatively, the second NBCCS antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401–1406, and Akerstrom, et al. (1985) *J. Immunol.*, 135: 2589–2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10°C. to 40° C.

a) Non-Competitive Assay Formats

Immunoassays for detecting NBCCS polypeptide may be either competitive or noncompetitive. Noncompetitive immunoassays are assays in which the amount of captured analyte (in this case NBCCS) is directly measured. In one preferred "sandwich" assay, for example, the capture agent (anti-NBCCS antibodies) can be bound directly to a solid substrate where they are immobilized. These immobilized antibodies then capture NBCCS present in the test sample. The NBCCS thus immobilized is then bound by a labeling agent, such as a second human NBCCS antibody bearing a label. Alternatively, the second NBCCS antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

b) Competitive Assay Formats

In competitive assays, the amount of analyte (NBCCS) present in the sample is measured indirectly by measuring the amount of an added (exogenous) analyte (NBCCS) displaced (or competed away) from a capture agent (anti NBCCS antibody) by the analyte present in the sample. In one competitive assay, a known amount of, in this case, NBCCS is added to the sample and the sample is then contacted with a capture agent, in this case an antibody that specifically binds NBCCS. The amount of NBCCS bound to the antibody is inversely proportional to the concentration of NBCCS present in the sample.

In a particularly preferred embodiment, the antibody is immobilized on a solid substrate. The amount of NBCCS bound to the antibody may be determined either by measuring the amount of NBCCS present in an NBCCS/ antibody complex, or alternatively by measuring the amount of remaining uncomplexed NBCCS. The amount of NBCCS may be detected by providing a labeled NBCCS molecule.

A hapten inhibition assay is another preferred competitive assay. In this assay a known analyte, in this case NBCCS is immobilized on a solid substrate. A known amount of anti-NBCCS antibody is added to the sample, and the sample is then contacted with the immobilized NBCCS. In this case, the amount of anti-NBCCS antibody bound to the immobilized NBCCS is inversely proportional to the amount of NBCCS present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

c) Other Assay Formats

In a particularly preferred embodiment, Western blot (immunoblot) analysis is used to detect and quantify the presence of NBCCS in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind NBCCS. The anti-NBCCS antibodies specifically bind to NBCCS on the solid support. These antibodies may be directly labeled or alternatively may be subsequently detected using labeled antibodies (e.g., labeled sheep antimouse antibodies) that specifically bind to the anti-NBCCS.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41).

d) Scoring of the Assay

The assays of this invention as scored (as positive or negative for NBCCS polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. In a preferred embodiment, a positive test will show a signal intensity (e.g., NBCCS polypeptide quantity) at least twice that of the background and/or control and more preferably at least 3 times or even at least 5 times greater than the background and/or negative control.

e) Reduction of Non-specific Binding

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

f) Labels

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

g) Substrates

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through non-specific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose. acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well-known and is amply illustrated in the literature. See, for example, *Immobilized Enzymes*, Ichiro Chibata, Halsted Press, New York, 1978, and Cuatrecasas (1970) *J. Biol. Chem.* 245 3059).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

C) Evaluation of NBCCS Expression Levels and/or Abnormal Expression

One of skill will appreciate that abnormal expression levels or abnormal expression products (e.g., mutated transcripts, truncated or non-sense polypeptides) are identified by comparison to normal expression levels and normal expression products. Normal levels of expression or normal expression products can be determined for any particular population, subpopulation, or group of organisms according to standard methods well known to those of skill in the art. Typically this involves identifying healthy organisms (i.e. organisms without NBCCS or basal cell carcinomas) and measuring expression levels of the NBCCS (PTC) gene (as described herein) or sequencing the gene, mRNA, or reverse transcribed cDNA, to obtain typical (normal) sequence variations. Application of standard statistical methods used in molecular genetics permits determination of baseline levels of expression, and normal gene products as well as significant deviations from such baseline levels.

D) Detection Kits

The present invention also provides for kits for the diagnosis of organisms (e.g., patients) with a predisposition (at risk) nevoid basal cell carcinoma or for sporadic basal cell carcinomas. The kits preferably include one or more reagents for determining the presence or absence of the NBCCS gene, for quantifying expression of the NBCCS gene, or for detecting an abnormal NBCCS gene or expression products of an abnormal NBCCS gene. Preferred reagents include nucleic acid probes that specifically bind to the normal NBCCS gene, cDNA, or subsequence thereof, probes that specifically bind to abnormal NBCCS gene (e.g., NBCCS containing premature truncations, insertions, or deletions), antibodies that specifically bind to normal NBCCS polypeptides or subsequences thereof, or antibodies that specifically bind to abnormal NBCCS polypeptides or subsequences thereof. The antibody or hybridization probe may be free or immobilized on a solid support such as a test tube, a microtiter plate, a dipstick and the like. The kit may also contain instructional materials teaching the use of the antibody or hybridization probe in an assay for the detection of a predisposition for NBCCS.

The kits may include alternatively, or in combination with any of the other components described herein, an anti-NBCCS antibody. The antibody can be monoclonal or polyclonal. The antibody can be conjugated to another moiety such as a label and/or it can be immobilized on a solid support (substrate).

The kit(s) may also contain a second antibody for detection of NBCCS polypeptide/antibody complexes or for detection of hybridized nucleic acid probes. The kit may contain appropriate reagents for detection of labels, positive and negative controls, washing solutions, dilution buffers and the like.

VI. Modulation of Expression of Endogenous NBCCS Genes

In still another embodiment, this invention provides methods of regulating the expression of endogenous NBCCS genes. The expression of an NBCCS gene product may be increased as a method of preparing mitigating or eliminating the tumorigenic potential of a cell. Conversely, upregulation of NBCCS gene may induce neoplastic transformation and provide a convenient and controllable model system for the study of basal cell carcinomas.

Methods of altering the expression of endogenous genes are well known to those of skill in the art. Typically such methods involve altering or replacing all or a portion of the regulatory sequences controlling expression of the particular gene that is to be regulated. In a preferred embodiment, the regulatory sequences (e.g., the native promoter) upstream of the NBCCS gene is altered.

This is typically accomplished by the use of homologous recombination to introduce a heterologous nucleic acid into the native regulatory sequences. To downregulate expression the NBCCS gene product, simple mutations that either alter the reading frame or disrupt the promoter are suitable. To upregulate expression of the NBCCS gene product, the native promoter(s) can be substituted with heterologous promoter(s) that induce higher than normal levels of transcription.

In a particularly preferred embodiment, nucleic acid sequences comprising the structural gene in question or upstream sequences are utilized for targeting heterologous recombination constructs. Upstream and downstream sequences can be readily determined using the information provided herein. Such sequences, for example, can be extended using 5'- or 3'-RACE. and homologous recombination constructs created with only routine experimentation.

The use of homologous recombination to alter expression of endogenous genes is described in detail in U.S. Pat. No. 5,272,071, WO 91/09955, WO 93/09222, WO 96/29411, WO 95/31560, and WO 91/12650.

VII. NBCCS (PTC) Therapeutics

A) Pharmaceutical Compositions

The NBCCS polypeptides, NBCCS polypeptide subsequences, anti-NBCCS antibodies, and anti-NBCCS antibody-effector (e.g., enzyme, toxin, hormone, growth factor, drug, etc.) conjugates or fusion proteins of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the NBCCS polypeptides and related compounds described of, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for topical administration to treat basal cell carcinomas, or their precursors, solar keratoses. In another embodiment, the compositions are useful for parenteral administration, such as intravenous administration or administration into a body cavity or lumen of an organ. The compositions for administration will commonly comprise a solution of the NBCCS polypeptide, antibody or antibody chimera/fusion dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present NBCCS polypeptides, antibodies or antibody chimer/fusions, or a cocktail thereof (i.e., with other proteins), can be administered for therapeutic treatments. In therapeutic applications, compositions are administered to a patient suffering from a disease (e.g., NBCCS or basal cell carcinoma) in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the NBCCS polypeptides, polypeptide subsequences, anti-NBCCS antibodies and anti-NBCCS-effector chimeras/fusions of the present invention are included a variety of disease conditions caused by nevoid basal cell carcinoma syndrome and/or basal cell carcinomas. Preferred applications include treatment of NBCCS, in particular treatment of the developmental anomalies characteristic of NBCCS and treatment of cancers, in particular basal cell carcinomas.

B) Cellular Transformation and Gene Therapy

The present invention provides packageable human NBCCS (PTC) nucleic acids (cDNAs) for the transformation of cells in vitro and in vivo. These packageable nucleic acids can be inserted into any of a number of well known vectors for the transfection and transformation of target cells and organisms as described below. The nucleic acids are transfected into cells, ex vivo or in vivo, through the interaction of the vector and the target cell. The NBCCS cDNA, under the control of a promoter, then expresses the NBCCS protein thereby mitigating the effects of absent NBCCS genes or partial inactivation of the NBCCS gene or abnormal expression of the NBCCS gene.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies. As an example, in vivo expression of cholesterol-regulating genes, genes which selectively block the replication of HIV, and tumor-suppressing genes in human patients dramatically improves the treatment of heart disease, AIDS, and cancer, respectively. For a review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al, *Gene Therapy* (1994) 1:13 –26.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat No. 5,279,833; Brigham (1991) WO 91/06309; and Felgner et al. (1987) *Proc. Natl. Acad Sci. USA* 84: 7413–7414), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra).

AAV-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invest.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.* 4:2072–2081; Hermonat and Muzyczka (1984) *Proc. Natl. Acad. Sci. USA* 81:6466–6470; McLaughlin et al. (1988) and Samulski et al. (1989) *J. Virol.* 63:03822–3828. Cell lines that can be transformed by rAAV include those described in Lebkowski et al. (1988) *Mol. Cell. Biol.* 8: 3988–3996.

A) Ex vivo Transformation of Cells.

Ex vivo cell transformation for diagnostics, research, or for gene therapy (e.g., via re-infusion of the transformed cells into the host organism) is well known to those of skill in the art. In a preferred embodiment, cells are isolated from the subject organism, transfected with the NBCCS gene or cDNA of this invention, and re-infused back into the subject organism (e.g., patient). Various cell types suitable for ex vivo transformation are well known to those of skill in the art. Particular preferred cells are progenitor or stem cells (see, e.g., Freshney et al., *Culture of Animal Cells, a Manual of Basic Technique, third edition* Wiley-Liss, New York (1994)) and the references cited therein for a discussion of how to isolate and culture cells from patients).

As indicated above, in a preferred embodiment, the packageable nucleic acid encodes an NBCCS polypeptide under the control of an activated or constitutive promoter. The transformed cell(s) express functional NBCCS polypeptide which mitigates the effects of deficient or abnormal NBCCS gene expression.

In one particularly preferred embodiment, stem cells are used in ex-vivo procedures for cell transformation and gene therapy. The advantage to using stem cells is that they can be differentiated into other cell types in vitro, or can be introduced into a mammal (such as the donor of the cells) where they will engraft in the bone marrow. Methods for differentiating CD34$^+$ cells in vitro into clinically important immune cell types using cytokines such a GM-CSF, IFN-γ and TNF-α are known (see, Inaba et al. (1992) *J. Exp. Med.* 176: 1693–1702, and Szabolcs et al. (1995) 154: 5851–5861).

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as CD4$^+$ and CD8$^+$ (T cells), CD45$^+$ (panB cells), GR-1 (granulocytes), and Ia$^d$ (differentiated antigen presenting cells). For an example of this protocol see, Inaba et al. (1992) *J. Exp. Med.* 176: 1693–1702.

In humans, bone marrow aspirations from iliac crests are performed e.g, under general anesthesia in the operating room. The bone marrow aspirations are approximately 1,000 ml in quantity and are collected from the posterior iliac bones and crests. If the total number of cells collected is less than about $2 \times 10^8$/kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g, on affinity columns which bind CD34. After the bone marrow is harvested, the mononuclear cells are separated from the other components by means of Ficoll gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation. The final concentration for the anti-CD34 antibody is 10 μg/ml. After two washes, paramagnetic microspheres (DynaBeads, supplied by Baxter Immunotherapy Group, Santa Ana, Calif.) coated with sheep anti-mouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml is added to release the beads from the CD34+ cells. Alternatively, and preferably, an affinity column isolation procedure can be used which binds to CD34, or to antibodies bound to CD34 (see, the examples below). See, Ho et al. (1995) *Stem Cells* 13 (suppl. 3): 100–105. See also, Brenner (1993) *Journal of Hematotherapy* 2: 7–17.

In another embodiment, hematopoietic stem cells are isolated from fetal cord blood. Yu et al. (1995) *Proc. Natl Acad. Sci. USA* 92: 699–703 describe a preferred method of transducing CD34+ cells from human fetal cord blood using retroviral vectors.

B) In Vivo Transformation

Vectors (e.g., retroviruses, adenoviruses, liposomes, etc.) containing therapeutic nucleic acids can be administered directly to the organism for transduction of cells in vivo. Administration is by any of the routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampules and vials.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis NBCCS predilection or onset or basal cell carcinoma predilection or onset, the physician evaluates circulating plasma levels of the vector, vector toxicities, progression of the disease, and the production of anti-vector antibodies. In general, the dose equivalent of a naked nucleic acid from a vector is from about 1 $\mu$g to 100 $\mu$g for a typical 70 kilogram patient, and doses of vectors which include a retroviral particle are calculated to yield an equivalent amount of therapeutic nucleic acid.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

In a preferred embodiment, prior to infusion, blood samples are obtained and saved for analysis. Between $1 \times 10^8$ and $1 \times 10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion can be repeated every 2 to 3 months. After the first treatment, infusions can be performed on a outpatient basis at the discretion of the clinician. If the reinfusion is given as an outpatient, the participant is monitored for at least 4, and preferably 8 hours following the therapy.

Transduced cells are prepared for reinfusion according to established methods. See, Abrahamsen et al. (1991) *J. Clin. Apheresis*, 6: 48–53; Carter et al. (1988) *J. Clin. Apheresis*, 4:113–117; Aebersold et al. (1988) *J. Immunol. Meth.*, 112: 1–7; Muul et al. (1987) *J. Immunol. Methods* 101:171–181 and Carter et al. (1987) *Transfusion* 27: 362–365. After a period of about 2–4 weeks in culture, the cells should number between $1 \times 10^8$ and $1 \times 10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

EXAMPLES

The following examples are offered to illustrate, but not to limit the present invention.

Example 1

Cloning of a Human Patched Homologue

This example describes the isolation of a complete human PATCHED cDNA sequence which encodes a putative protein of 1172 amino acids, and displays 61% sequence identity to the Drosophila PATCHED protein. Drosophila patched (ptc) is a segment polarity gene required for the correct patterning of larval segments and imaginal discs during fly development (Nakano et al. (1989) *Nature* 341: 508–13; Hooper et al. (1989) *Cell* 59: 751–765). Based on genetic studies, patched is a component of the signaling pathway of the morphogen hedgehog (Basler et al. (1994) *Nature* 368: 208–214; Capdevila et al (1994) *EMBO J.* 13: 71–82; Ingham (1991) *Nature* 353: 184–187). Since patched is a putative membrane-spanning protein, and is expressed in hedgehog responsive cells, it has been proposed to be the hedgehog receptor (Ingham (1991) supra.).

In vertebrates, several hedgehog homologs have been identified. The best characterized of them, sonic hedgehog, has been implicated in the dorsal-ventral patterning of neural tube (Roelink et al. (1994) *Cell* 76: 761–775; Roelink (1995) *Cell* 81: 445–455), in the differentiation of somites (Johnson et al. (1994) *Cell* 79: 1165–1173) and in the establishing of the anterior-posterior axis of the limb bud (Riddle et al. (1993) Cell, 75: 1401–1416). The biochemical basis of hedgehog signaling in vertebrates remains poorly understood and has been hampered largely by the lack of a proven receptor for the molecule.

Experimental Procedures

Cosmid Isolation

Cosmids used in this study were isolated from a human chromosome 9-specific genomic cosmid library (LL09NCO1"P", Biomedical Sciences Division, Lawrence Livermore National Laboratory, Livermore, Calif. 94550) by screening with the YAC clone ICI-2ef8 (UK Human Genome Mapping Project Resource Centre). This clone contains the microsatellite marker D9S287 which has been localized to chromosome 9q22.3 (Povey et al. (1994) *Ann. Hum. Genet.*, 58: 177–250). The isolation of YAC DNA and hybridization was performed as described by Vorechovsky et al. (1994) *Genomics*, 21: 517–24. The localization of the cosmids was confirmed by hybridization to YAC ICI-2ef8 resolved by means of pulse-field gel electrophoresis. The 96 well plate format of the cosmid clones that contain PTC is 42H11, 96F9, 218A8, 226G7.

Library screening

Human cDNA clones were isolated from a fetal brain cDNA library in the lambda ZAPII phage vector (Stratagene, La Jolla, Calif., USA), using standard procedures. The probes were labeled with [$^{32}$P]dCTP by random priming (Redisrime, Amersham). Positive clones were rescued using the 704 helper phage/pBluescript excision system (Rapid Excision Kit, Stratagene) and sequenced. Mouse genomic clones were isolated from a 129SV lambda FixII library (Stratagene). Phage DNA was cut with EcoRI and hybridized with PTC specific probes. Mouse cDNA clones were isolated from an 11.5 dpc mouse embryo (Swiss male) library constructed in lambda gt10. Hybridization was performed at 55° C. Positive clones were subcloned into pBluescript II SK (Stratagene) digested with NotI.

Sequencing

Templates for sequencing were prepared from overnight cultures of rescued cDNA clones and/or EcoRI cosmid fragments subcloned in pBluescript KS(+) using a plasmid purification kit (Qiagen). Sequencing was performed with the Taq Dyedeoxy Terminator Cycle sequencing kit (Applied Biosystems) according to the manufacturer's instructions. Sequencing reactions were resolved on an ABI 373A automated sequencer. Sequence analysis was performed using the GCG software. BLAST searches were performed with the NCBI network service. PTC sequences have been deposited in GENBANK under accession #U43148.

Northern hybridization

Expression of human PTC mRNA was examined by Northern hybridization of human tissue blots (Clontech) using cDNA probes labeled with [$^{32}$P]dCTP. Hybridization solution contained 5×SSPE, 10×Denhardt's solution, 100 mg/ml denatured, sheared herring sperm DNA, 50% formamide and 2% SDS. Washes were performed at 60° C. with 2×SSC and 0.1% SDS.

Chromosomal localization

The chromosomal localization of human PTC was identified by PCR analysis of DNA panels obtained from human-hamster hybrid cells. The panel consisted of both whole chromosome 9 hybrids and deletion hybrids of 9q22.3. The primers used were PTC1 (5'-TTG CAT AAC CAG CGA GTCT-3' (SEQ ID NO: 2)) and PTC2 (5'-CAA ATG TAC GAG CAC TTC AAGG-3' (SEQ ID NO: 3)). Murine Ptc was mapped by means of interspecific backcross mapping. The panels were provided by the Jackson Laboratory (Bar Harbor, Me.) and are the BSB panel from a cross (C57BL/6J×M. spretus)×C57BL/6J and a similar BSS panel made up of DNA from the reciprocal backcross (C57BL/6JEi×SPRET/Ei)×SPRET/Ei. Mapping was performed by means of SSCP (single strand conformation polymorphism) analysis with the primers W18F3 (5'-CTG TCA AGG TGA ATG GAC-3' (SEQ ID NO: 4) and W18R3 (5'-GGG GTT ATT CTG TAA AAGG-3' (SEQ ID NO: 5)). PCR reactions were performed in the presence of [$^{32}$P]dCTP. The samples were resolved on a 6% acrylamide gel (2.6% cross-linking) at 4° C. at 70 watts within 1.5 hours. Genetic linkage was performed by segregation analysis.

In Situ Hybridization

Whole mount in situ hybridization on mouse embryos and subsequent sectioning was performed as described by Christiansen, et al. (1995) *Mech. Dev.* 51: 341–50. The mouse Ptc probe was a 706 bp NotI/PstI cDNA fragment from the 5' end of the gene, subcloned in pBluescriptII SK. The probe was linearized with SacII, the overhang blunted by incubation with 5 U/mg Klenow at 22° C. for 15 minutes, and antisense RNA synthesized by transcribing with T7 RNA polymerase.

Results and Discussion

Cloning of a Human PTC Homolog

Cosmids used in this study were isolated from a human chromosome 9-specific genomic cosmid library using the YAC clone ICI-2ef8. This clone contains the microsatellite marker D9S287 which has been localized to chromosome 9q22.3. Sequencing of a 1.8 kb EcoRI fragment of cosmid 42H11 yielded an open reading frame with significant homology to three consecutive stretches of the Drosophila ptc protein. Using the 1.8 kb EcoRI fragment as a probe the complete human and partial mouse PTC cDNA sequences were isolated.

The sequence of the human PTC cDNA consists of an open reading frame of 3888 nucleotides; also sequenced were 441 and 2240 nucleotides on the 5' end and on the 3' end, respectively (SEQ ID NO: 1 FIG. 8). The open reading frame of human PTC cDNA encodes for a putative protein of 1296 amino acids. This open reading frame is initiated by an ATG codon that has a moderate match for the translational start consensus sequence in vertebrates (GAGGCTAUGT (SEQ ID NO:6) PTC versus GCCGCCATGG (SEQ ID NO:7) (Kozak (1991) *J. Biol. Chem.*, 266: 19867–19870)). Assuming that this codon encodes for the first amino acid of the protein, human ptc consists of 1296 amino acids with a relative molecular weight ($M_r$) of 131× 10$^3$. It shows 61% sequence identity to its Drosophila counterpart. Upstream of the ATG, the open reading frame extends for another 354 nucleotides (starting at base pair 88 of the sequence shown in FIG. 8). The 3' untranslated region contains a canonical polyadenylation signal (AATAAA (SEQ ID NO: 8)) as well as MRNA destabilizing ATTTA (SEQ ID NO: 9) motifs. These are localized 1031 nucleotides and 175, 371, and 1143 nucleotides after the termination codon, respectively.

An alternative transcript is observed that splices from exon 3 to exon 2a. The open reading frame ends in exon 2a (see, SEQ ID NO: 59) but does not contain an AUG. Exon 2 can splice to one of three different first exons. Exon 1b (see SEQ ID NO: 58) is homologous to the described first exon of the mouse mRNA and has an ATG followed by ORF. Exon 1a has ORF through the entire length and a potential splice acceptor site (see, e.g., SEQ ID NO: 58). Exon 3 contains the first in-frame ATG for all the transcripts except the one initiating in exon 1b. A map of the promoter region of NBCCS (PCT) is provided in FIG. 3.

Hydropathy analysis (Kyte et al. (1982) *J. Mol. Biol.*, 157: 105–32) of the entire open reading frame of human PTC predicts the presence of eight main hydrophobic stretches. Distribution of the hydrophobic blocks is remarkably well conserved between species indicating that human PTC, like its Drosophila counterpart, is an integral membrane protein.

Chromosomal Localization of PTC

Chromosomal localization of human PTC on 9q22.3 was confirmed by PCR analysis of chromosome 9 hybrids, and deletion hybrids of 9q22.3, human-hamster hybrid DNA panels. The primers used (PTC1, PTC2) were derived from a sequence of a 1.8 kb EcoRI fragment of cosmid 42H11. Primer PTC1 is derived from an exon sequence and PTC2 from an intron sequence. All DNA hybridization and cDNA sequencing data suggest that human PTC is a single copy gene. Murine Ptc maps to a short region of chromosome 13, close to the murine Facc locus (no recombination out of 188 meioses). This region contains the mouse mutations flexed tail (f) and purkinje cell degeneration (pcd), and it is syntenic with human 9q22-q31. Both f and pcd involve abnormal development of cells of the bone or brain and could be allelic to Ptc.

Expression of PTC

Northern blot analysis revealed five distinct PTC transcripts in all human tissues examined. Expression of these transcripts appears to be differentially regulated. During mouse embryogenesis, expression of Ptc is first detected at E 8.0 dpc in ventral neuroepithelial tissue in two separate domains along the midline. Expression persists in ventral neural cells through to 9.5 dpc and transcripts are also detected in lateral mesenchyme surrounding the neural tube. Ptc transcription is detected in the somites soon after the time of their appearance and follows a rostro-caudal gradient of expression. Somite expression is restricted to epithelial cells within the medial aspects of each somite. Expression of Ptc is also detected in the posterior ectoderm of each limb bud from 10.0 dpc to 12.5 dpc. This region corresponds to surface ectoderm that covers the ZPA. Other sites of Ptc expression during this period include the inner surfaces of the branchial arches which flank the oropharyngeal region, cells surrounding the placodes of the vibrissae and the genital eminence.

The expression pattern of Ptc points to a close relationship between Ptc and the hedgehog family of morphogens. This relationship was originally established in *Drosophila* (Ingham et al (1991) *Nature*, 353: 184–187). In vertebrates, the best characterized hedgehog homolog, sonic hedgehog, has been implied in the induction of the floorplate and motor neurons within the ventral neural tube (Jessell et al. (1990)

*Harvey Lect.*, 86: 87–128; Yamada et al (1993), 73: 673–686) as well as in the differentiation of sclerotome within the somites (Pourquie et al. (1993) *Proc. Natl. Acad. Sci. USA*, 90: 5242–5246). In the limb bud, sonic hedgehog expression in the mesenchymal 'zone of polarizing activity' triggers anterior-posterior patterning of the limb (Riddle et al (1993) *Cell*, 75: 1401–1416). Our data show that vertebrate PTC is expressed in all major target tissues of sonic hedgehog, such as the ventral neural tube, somites and tissues surrounding the zone of polarizing activity of the limb bud. The striking spatial complementarity and temporal coincidence of the sonic hedgehog and Ptc expression patterns suggest that both genes might be members of a common signaling pathway.

The localization of PTC in the region containing the nevoid basal cell carcinoma syndrome (NBCCS) gene is intriguing. NBCCS is an autosomal dominant disorder which predisposes affected individuals to basal cell carcinomas of the skin, medulloblastomas and various other tumors (Gorlin (1987) *Medicine* (Baltimore) 66: 98–113). Recent genetic studies have placed the gene for the nevoid basal cell carcinoma syndrome to chromosome 9q22.3, between the markers Fanconi anaemia complementation group A (Farndon et al. (1994) *Genomics*, 23: 486–489) and D9S287 (Pericak-Vance (1995) *Ann. Hum. Genet.*, 59: 347–365). Several lines of evidence suggest that PTC is a candidate gene for the nevoid basal cell carcinoma syndrome. Ptc expression is compatible with the congenital defects commonly found in NBCCS patients. Frequent symptoms in newborns and infants are developmental anomalies of the spine and ribs (Gorlin (1987 supra.). These malformations could be due to a PTC deficiency, expression of which coincides spatially and temporally with the development of the neural tube and of the somites. In addition, Ptc expression in the surface ectoderm surrounding the ZPA is consistent with limb abnormalities often observed in the patients with NBCCS (Gorlin (1987 supra.). PTC expression in all adult tissues points to a pleiotropic role of PTC in adult signal transduction pathways. Defects in these signaling pathways could account for the symptoms which develop postnatally.

Example 2

Mutations of the Human Homologue of Drosophila Patched in Nevoid Basal Cell Carcinoma Syndrome The nevoid basal cell carcinoma syndrome (NBCCS) is an autosomal dominant disorder characterized by multiple basal cell carcinomas (BCCs), pits of the palms and soles, keratocysts of the jaw, and a variety of other tumors and developmental abnormalities. NBCCS was mapped to chromosome 9q22.3 and both familial and sporadic BCCs display loss of heterozygosity for markers in this region, consistent with the gene being a tumor suppressor. Example 1 describes the isolation of a human sequence (PTC) with strong; homology to the Drosophila segment polarity gene. This example shows that human PTC is expressed in many of the tissues affected in NBCCS patients. Single-stranded conformation polymorphism analysis and sequencing revealed mutations of PTC in patients with the syndrome and in related tumors. The data indicate that human PTC is also an NBCCS gene and that a reduction in expression of this gene leads to the developmental abnormalities observed in the syndrome and that complete loss of patched function contributes to transformation of certain cell types.

Experimental Procedures
Subjects and samples

DNA samples were collected from 363 individuals in 128 NBCCS kindreds. Patients were examined by a clinical geneticist, and diagnosis of Gorlin syndrome was based on at least two major features of the syndrome; e.g., jaw cysts, palmar pits, multiple basal cell carcinomas, and a family history of typical Gorlin syndrome. Lymphoblastoid cell lines were made from at least one affected member of 82 kindreds. 252 basal cell carcinomas were collected as either fresh or paraffin-embedded specimens.

Short Tandem Repeat Polymorphisms

For linkage analysis and tumor deletion studies, PCR reactions were performed in 50 $\mu$L volumes containing 100 ng of template DNA, 200 M dNTPs, 1.5 MM $MgCl_2$, 0.25 mM spermidine, 10 pM of each primer, I Ci $^{32}$P dCTP (Amersham, Arlington Heights, Ill., USA), and 1.25 Units Taq polymerase (Promega, Madison, Wis., USA) in Promega buffer (10 mM TrisHCl, pH 9, 50 mM KCl, 0.1% Triton X-100). An Ericomp Dual Block thermocyler was set with the following parameters for 25 cycles: 94° C., 1 min, 55° C., 30 sec, 72° C., 2 min. PCR products were analyzed on an 5% polyacrylamide gels. Autoradiography was carried out at −70° C. with Kodak XAR film. Loci in the NBCCS region that were typed are shown in FIG. 1, and primer sequences are available from the Genome Data Base (http://gdbwww.gdb.org).

Pulsed-field Gel Electrophoresis (PFGE)

Cultured lymphoblastoid cells were embedded in LMP agarose (Bio Rad, Hercules Calif., USA) at a concentration of approximately $2 \times 10^6/220$-1 block, and DNA was extracted according to standard methods (Sambrook et al. supra.) Quarter blocks were digested with SacII, MluI, NotI, BssHI, NruI, and SfiI under conditions recommended by the manufacturer (New England Biolabs, Beverly, Mass., USA). Electrophoresis was carried out with the Bio Rad CHEF DR 11 apparatus using, 1% agarose gels run for 20 hours at 200 volts with a pulse time of 75 sec. For higher resolution of fragments under 500 kb, a 25 second pulse time was used.

Transfer to nylon membranes (Du Pont Gene Screen Plus, Du Pont, Co., Boston, Mass., USA) was performed according to the manufacturer's instruction after exposure of the gel to UV (6–7 mW/$cm^2$) for two minutes. Probes were labeled to a specific activity of approximately $10^9$ DPM/g, with $dCT^{32}P$ (Amersham) by the random primed synthesis method (Boehringer Mannheim Kit, Boehringer Mannheim Corp., Indianapolis, Ind., USA). Hybridization was carried out for 18 hours at 65° C. in 0.5 M sodium phosphate (pH 7.2), 7% SDS, 1% BSA, 1 mM EDTA and 200 $\mu$g/ml herring sperm. For probes containing repetitive sequences, sheared, sonicated human placental DNA (Sigma Chemical Co., St. Louis, Mo., USA) was added to the hybridization solution (500 $\mu$g/ml) and preassociated with the probe at 65° C. for 45 minutes prior to hybridization to the filter. Filters were washed in 0.1×SSC with 1% SDS at 65° C. and exposed to autoradiographic film with an intensifying screen at −70° C. from 12 hours to three days. Probes that detected similar sized fragments on different blots were directly compared for comigrating fragments by hybridization to the same blot. Blots were stripped in 0.4N NaOH for 30 min at room temperature between uses.

Fluorescence in situ Hybridization

Cosmid clones were labeled by nick translation with biotin-11-dUTP, dioxigenin-11-dUTP, or both, and hybridized to metaphase and interphase chromosomes under suppression conditions. Biotinylated probes were detected with 5 $\mu$g/ml of fluorescein isothiocyanate (FITC)-conjugated avidin DCS. Dioxigenin labeled probes were detected with 2 $\mu$g/ml anti-dioxigenin Fab conjugated to rhodamine. The chromosomes were counterstained with 200 ng/ml of 4,6-diamidino-2-phenylindole-dihydrochloride (DAPI). Images were obtained using a microscope coupled to a cooled CCD camera. The digitalized images were processed, pseudocolored and merged and the distances between signals were measured.

Cosmid and BAC Screening

A gridded chromosome 9 cosmid library (LL09NCO1) was replicated onto nylon filters (Gene Screen Dupont Plus, Du Pont Co.) and screened according to the recommendations of the Human Genome Center, Lawrence Livermore National Laboratory. Positive coordinates were streaked out to single colonies and confirmed to contain the appropriate markers by PCR or hybridization. Gridded BAC filters were screened by hybridization according to the manufacturer's recommendations (Research Genetics, Huntsville, Ala., USA). Because of the small chance of chimerism in cosmids and BACS, fragments from the ends of contigs were mapped with a panel of human-hamster somatic cell hybrids to confirm their localization on chromosome 9q22.

Isolation of cDNAs

Four methods were used to isolate candidate cDNAs. Direct cDNA selection (Parimoo et al. (1991) *Proc. Natl. Acad. Sci., USA,* 88: 9623–9627) was applied to pools of cosmids and BACs. Following two rounds of selection, the PCR products were size fractionated and cloned into PCRII (Invitrogen, Leek NV, Netherlands). Transformants were gridded into 96 well plates, and replica filters were probed with the genomic template DNA to identify cDNAs that hybridized the correct genomic region.

Exon trapping, was performed using the method developed by Buckler et al. (1991) *Proc. Natl. Acad. Sci. USA,* 88: 4005–4009, and later modified by Church et al. (1994) *Nature Genetics,* 6: 98. BamH1/GblII digests of pools of 5 or 6 cosmids were cloned into the BamH1 site of the splicing vector pSPL3b (Burn et al. (1995) *Gene,* 161: 183–187). Trapped DNAs were sequenced and mapped back to the NBCCS candidate region by hybridization to the cosmids from which they were derived.

For HTF island cloning, YACs were size fractionated by pulsed field gel electrophoresis, excised from the gel, and digested with BssHII. Subsequently vectorette linkers were added and PCR amplification was performed using a vectorette primer and a 5' Alu primer (Valdes et al. (1994) *Proc. Natl. Acad Sci.,* 91: 5377–5381). After an initial denaturation at 100° C. for 5 min, 30 amplification cycles were performed with denaturation for 1 min at 98° C., annealing for 1 min at 60° C., and extension for 3 min at 72° C. Ten units of Taq polymerase were used in a total volume of 100 $\mu$l consisting of 50 mM KCl, 10 mM Tris pH 9, 2 mM MgCl$_2$, 0.1% Triton and 200 $\mu$M dNTP. The PCR products were electrophoresed on a 1% agarose gel, in order to determine their size, and subsequently cloned into the PGEM T vector (Promega) by a shotgun procedure.

For sequence sampling, the ends of chromosome 9 specific cosmids or cosmid subclones were directly sequenced (Smith et al. (1994) *Nature Genetics* 7: 40–47. Sequencing was performed on an ABI 373 DNA sequencer. The resulting, end sequences were manually trimmed, examined for simple sequence repeats, and used to search the DNA sequence databases. Both nucleotide and amino acid searches were performed. In addition sequences were examined for potential coding regions by GRAIL (Uberbacher and Mural (1991) *Proc. Natl. Acad. Sci. USA* 88: 11261–11265.

Short cDNA fragments obtained by the methods outlined above were extended by screening brain or epidermal cDNA libraries and by rapid amplification of cDNA ends (Marathon kit, Clontech, Palo Alto, Calif., USA).

Intron/exon Structure of the Human Patched Gene

Oligonucleotides were chosen at approximately 150 bp intervals spanning the cDNA of the human patched gene. PCR products were generated from cosmids 226G7, 42H11, 55A16, or 96F9. Reactions were performed in a 50 $\mu$l volume containing 25 pmol of various oligonucleotide combinations, 200 $\mu$mol dNTPs, 1.5 mM, or 1.85 mM, or 2.2 mM MgCl$_2$, 5 U Taq polymerase, and amplified for 35 cycles of 94° C. for 30 s, 55° C. for 30 s 72° C. for 2.5 min. Some samples were amplified by long range PCR using the Expand Long Template PCR system (Boehringer Mannheim) according to the manufacturer's instructions. PCR products were resolved on a 1% agarose gel and isolated by a DNA purification kit (Jetsorb, Genomed, Bad Oeynhausen, Germany). Sequencing of PCR fragments was performed with the Taq Dyedeoxy Terminator Cycle Sequencing, kit (Applied Biosystems, Foster City, Calif., USA). Sequencing, reactions were resolved on an ABI 373A automated sequencer. Positions of introns have been determined by predicted splice donor or splice acceptor sites.

Mutation Detection

A combined SSCP (Orita et al. (1989) *Ann. Hum. Genet.* 59: 347–365) and heteroduplex analysis (White et al (1992) *Genomics,* 12: 301–306) approach was used using optimized conditions (Glavac and Dean (1993) *Hum. Mutation,* 2: 404–414). DNA samples (100 ng) were amplified in PCR buffer containing, 1.5 mM MgCl, and $^{32}$P-dCTP for 35 cycles of 94° C., 30 sec, 55° C., 30 sec, 72° C., 30 sec. Products were diluted 1:3 in stop solution, denatured at 95° C. for 2 min and 3 $\mu$i loaded directly on gels. Gel formulations used were 1) 6% acrylamide:Bis (2.6% crosslinking,), 10% glycerol, room temp, 45W; 2) 6% acrylamide:Bis (2.6% crosslinking), 4 60W; 3) 10% acrylamide-:Bis (1.3% crosslinking) 10% glycerol4, 60W; 4) 0.5×MDE (ATGC Corp, Malvern, Pa.), 10% glycerol4, 50W. Gels were run for 3–16 hours(3000Vh/100 bp), dried and exposed to X-ray film for 2–24 hrs. Heteroduplexes were identified from the double-stranded DNA at the bottom of the gels, and SSCPs from the single-stranded region.

Samples showing; variation were compared to other family members to assess segregation of the alleles, or to normal DNA from the same patient, in the case of tumors. PCR products with SSCP or heteroduplex variants were treated with shrimp alkaline phosphatase and exonuclease I (United States Biochemical) and cycle sequenced with Amplitaq FS™ (Perkin Elmer, Norwalk, Conn., USA). The products were analyzed on an Applied Biosystems model 373 DNA sequencer.

Results and Discussion

Fine Mapping by Linkage and Tumor Deletion Studies

Since the original mapping of the gene in 1992, linkage studies have narrowed the NBCCS region to a 4 cM interval between D9S180 and D9S196 (Goldstein et al. (1994) supra; Wicking et al. (1994) *Genomics,* 22: 505–511). Farndon et al (1994) supra, reported recombination involving an unaffected individual that tentatively placed the gene proximal to D9S287.

The present experiments identified one recombination between D9S287 and FACC in a three-generation family. The recombinant individual was a 1.5 year old female presumed to be affected on the basis of macrocephaly, strabismus, and frontal bossing. Some of the key features of the syndrome such as basal cell carcinomas, jaw cysts, and palmar pits, were lacking; but these features have age-dependent expression, and their presence in a young child would not be expected. With the assumption that she carried the gene, the recombination in this family placed NBCCS proximal to D9S287.

Allelic loss in BCCs was concordant with linkage mapping in placing the gene between D9S 196 and D9S 180. Most hereditary tumors with allelic loss deleted the entire region between the flanking markers. However, one hereditary cardiac fibroma showed loss at D9S287 but not D9S280 on the non-disease carrying allele suggesting that the gene is located distal to D9S280. In sporadic BCCs, four tumors were found that retained D9S287 and lost more distal markers, but also two tumors that lost the proximal marker D9S280, but not D9S287.

Several hypotheses can be proposed to explain this discrepancy in tumor deletion mapping, and between tumor deletions and linkage studies. A gene other than NBCCS could be responsible for the allelic loss in some sporadic tumors. NBCCS is almost certainly the target of allelic loss in hereditary tumors because these tumors always lose the copy of the NBCCS gene from the unaffected parent and retain the inherited mutation (Bonifas et al. (1994) Hum. Mol. Genet., 3: 447–448). If a second locus were driving allelic loss, then the alleles from the affected parent and the unaffected parent would be lost with equal frequency. However, there may be two different tumor suppressors on chromosome 9q that are both important in basal cell carcinomas. The APC gene and MCC gene, for example, are both mutated in colon cancer and lie within 1 Mb of each other on chromosome 5q (Hampton et al. (1992) Proc. Natl. Acad Sci. USA 89: 8249–8253). The observation of a clearly distinct pattern of allelic loss, involving, D9S180 but not D9S287, in squamous cell carcinoma of the skin supports the presence of more than one tumor suppressor in the 9q22.3 region. Additionally a putative tumor suppressor has been mapped to 9q21-31 in bladder cancers, and may be distinct from the NBCCS gene (Knowles et al. (1 995) Br. J Urol. 75: 57–66).

A second possibility is that regions on both sides of D9S287 are deleted in some tumors, but that the more proximal deletions are not always detected by available markers. In fact two tumors were observed that deleted markers both proximal and distal to D9S127, probably reflecting genetic instability in tumor cells. Finally, NBCCS could be a large gene that extends on both sides of the D9S287 locus. Taken together the data provided herein suggested that the most likely location of the NBCCS gene was between markers D9S280 and D9S287. Nevertheless, due to the discrepancies in tumor deletions, physical mapping and cDNA isolation from the entire region between D9S196 and D9S180 were undertaken.

Physical Mapping

Twenty-nine YACs containing markers from this region were obtained from the CEPH megaYAC library. Eighteen formed an overlapping contig between D9S196 and D9S180 with at least 2-fold redundancy. Based on this contig the minimum distance between the flanking markers was 1.5 Mb, but virtually all large YACs had internal deletions as judged by STS content. Additional YACs were obtained from the ICI library to provide redundancy in areas apparently prone to deletion. Cosmid and BAC contigs were constructed around known STSs and genes, and additional cosmids from the region were isolated by hybridizing YACs to the Lawrence Livermore gridded cosmid library. In total over 800 cosmids specific to this region were gridded into 96-well grid plates and contigs of BACS, P1s and cosmids covering 1.5 Mb were constructed (FIG. 1). Because of deletions in YACs and some gaps in the cosmid and BAC contig, pulsed field gel electrophoresis (PFGE) and FISH were used to integrate the cloned regions. Based on the sizes of restriction fragments in this region and FISH estimates, the physical distance from D9S180 to D9S196 was estimated at not less than 2 Mb.

Isolation of cDNAs

Harshman et al (1995), supra, showed that different methods of identifying cDNAs from a genomic region result in a surprisingly different array of candidate genes. Several methods were used to find genes that map to chromosome 9q22 including sample sequencing of cosmids, exon trapping, HTF island cloning, and direct selection of cDNAs from BACs and cosmids. In addition, genes known to lie in this general area were more finely mapped by use of somatic cell hybrids made from two NBCCS patients with visible 9q22 deletions (submitted to NIGMS repository), YAC contigs, and FISH. Ten genes, ten ESTs with sequences in GENBANK, and 31 anonymous selected cDNA fragments, HTF island clones, and trapped exons with no known homology were identified (Table 1).

Screening Patients for Germline Deletions or Rearrangements

Because chromosome 9q22 appeared to be very gene rich, an attempt was made to localize the NBCCS gene more precisely by searching for submicroscopic rearrangements in patients. Fifteen cosmids at approximately 100–200 kb intervals spanning the region between D9S196 and D9S180 were hybridized to PFGE blots of 82 unrelated NBCCS patients. In addition probes from genes known to map to the interval as well as those identified in the course of the study were included in this analysis. PFGE variants were identified in three patients with genomic probes from within the Fanconi's anemia complementation group C (FACC) gene. All three were heterozygous for SacII bands approximately 30 kb shorter than normal (310 vs 280 kb). The limit of resolution of PFGE was about 10 kb, so that it was not possible to determine whether the apparently identical variant SacII bands were exactly the same size. Other restriction enzymes including NotI, BssHII, MluI, SfiI, and NruI did not show variant bands. The variations were not consistent with germline deletions in these patients but could conceivably be caused by point mutations creating new restriction sites or other small alterations such as the recurrent inversions seen in the F8C gene of many hemophiliacs (Lakich et al. (1993) Nat. Genetics, 5: 236–241).

The nature of the DNA alterations causing these changes on PFGE has not yet been elucidated, but the data relating them to the disease are compelling. The families of two of the patients with variations were not available for study. However the third patient was a sporadic case of NBCCS, and neither parent had the SacII alteration. The finding of this variant in a patient but not in her parents could be interpreted as the result of hypermutability of some CG-rich region near FACC, but no variation in this region was identified in PFGE blots of over 100 normal chromosomes.

TABLE 1 cDNA clones from the NBCCS region on chromosome 9q22.3.

| Clone Designation[a] | Clone type[b] |
|---|---|
| cDNAs previously mapped to chromosome 9q and more finely mapped with somatic cell hybrids, PFGE, and YAC contigs. | |
| FACC | Gene |
| NCBP | Gene |
| HSD17B3 | Gene |

TABLE 1-continued cDNA clones from the NBCCS region on chromosome 9q22.3.

| Clone Designation[a] | Clone type[b] |
|---|---|
| TMOD | Gene |
| XPA | Gene |
| SYK | Gene |
| WI-11139 | EST (R14225) |
| WI-11414 | EST (T88697) |
| WI-8684 | EST (R14413) |
| D9S1697 | EST (R06574) |
| D9S1145 | EST (contains R17127 and Z38405) |

Novel clones or clones not previously mapped to chromosome 9q identified by sample sequencing exon trapping, HTF island cloning or cDNA selection.

| | |
|---|---|
| ZNF169 | Gene |
| FBP1 | Gene |
| PTC | Gene |
| Coronin homologue | Gene |
| 2F1a | EST (R39928) |
| 2F1b | EST (T11435) |
| 11F21 | EST (Z43835) |
| 31F3 | EST (R16281) |
| yo20g05.s1 | EST (Merck EST) | plus 31 anonymous selected cDNA fragments, HTF island clones, and trapped exons from YACs and cosmid pools[c]

[a]For known genes and anonymous cDNAs that have been submitted to the Genome Data Base (http://gdbwww.dgw.org/gdb), standard locus nomenclature is used. For ESTs without a GDB number, WI indicates a Whitehead Institute clone (http://www-genome.wi.mit.edu).
[b]NCNR accession numbers, where available, are given in parentheses for anonymous ESTs. Additional information can be obtained at http://www.ncgr.org/gsdb.
[c]Additional sequence data will be required to determine whether some of the anonymous cDNAs represent different portions of the same genes.

Evaluation of PTC as a Candidate Gene

Because variant PFGE bands were identified in the FACC region and one recombinant as well as tumor deletion studies suggested a possible location near this marker, candidate cDNAs that mapped to this area were examined. FACC, itself, was not considered as a candidate because heterozygous mutations in this gene do not cause NBCCS (Strathdee et al. (1992) Nature, 356: 763–767). FACC and PTC (a novel human gene with strong homology to Drosophila patched) hybridized to the same 650 kb NotI fragment and 675 kb and 1000 kb (partial) MluI fragments. Mouse interspecies backcross analysis determined that there were no recombinants between the PTC and FACC genes out of 190 meioses. PTC and D9S287 were both present on ICI YAC 2EF8 having, a size of 350 kb strongly suggesting that PTC lies between D9S287 and FACC.

Figure 2:
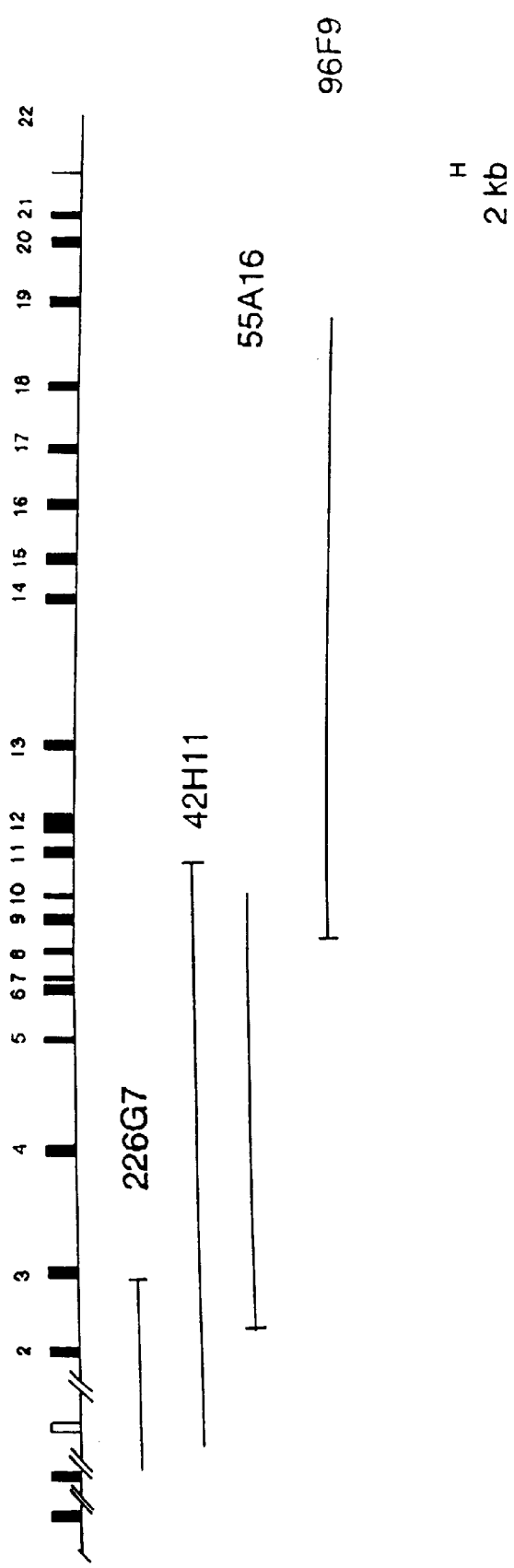
FIG. 2 shows a map of the PTC locus. The gene lies on 4 overlapping cosmids including 226G7, 42H11, 55A16, and 96F9 (LL09NCO1, 96-well coordinates). The coding exons of the gene are shown as filled boxes and non-coding (untranslated) exons as open boxes. Splice variants of the 5' non-coding, region of the gene indicate at least two alternate first exons and possibly a third alternate exon (see Example 2).
Figure 4:
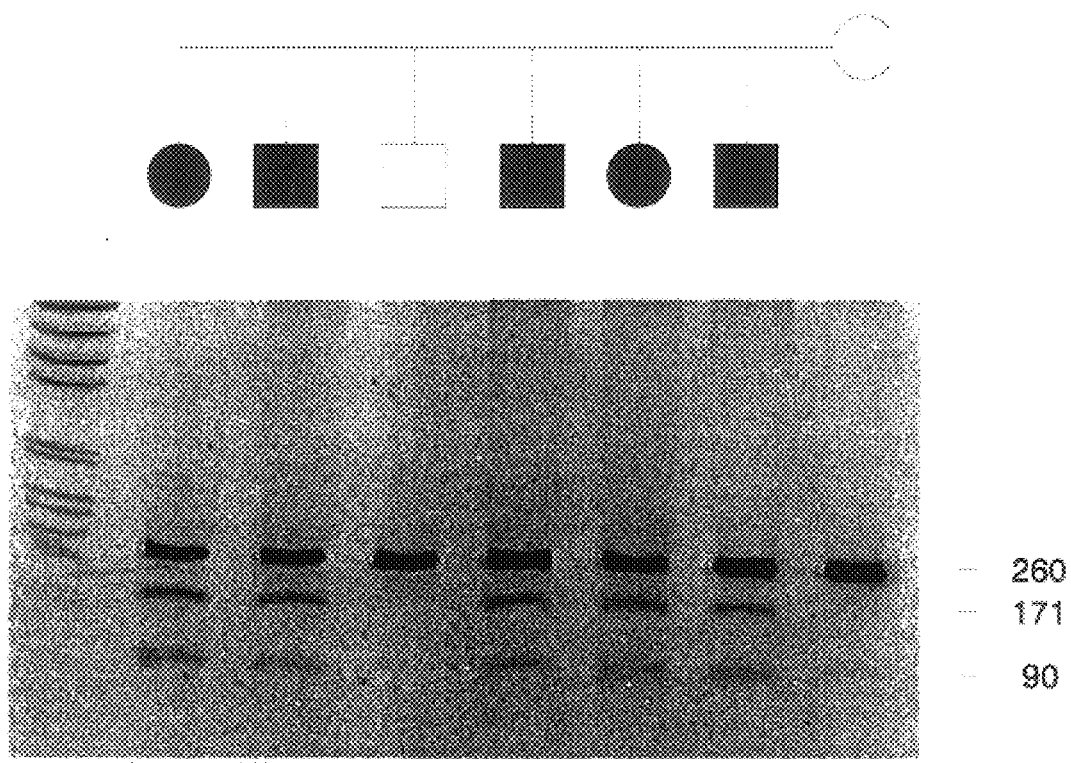
FIG. 4 illustrates segregation of a premature termination mutation of PTC in an NBCCS pedigree. The C1081T (Q210X) mutation segregating in this kindred creates a Bfal site. PCR with flanking primers produces a 260 bp product, which digests to 171 bp and 90 bp fragments in affected family members. The PCR product remains undigested in unaffected family members.

To screen for mutations in the PTC gene, the intron/exon boundaries of the gene were determined from genomic clones and long range PCR products. PTC consists of 21 exons and the gene spans approximately 34 kb (FIG. 2). Panels of unrelated NBCCS patients and BCCs were screened by single-stranded conformation polymorphism (SSCP) analysis (primers used for amplification of PTC exons are shown in Table 2). Patients displaying variations were compared to unaffected individuals of the same race, and variants found only in affected individuals were further characterized by DNA sequencing. Of the mutations identified in unrelated patients four were deletions or insertions resulting, in frameshifts and two were point mutations leading to premature stops (Table 3, FIGS. 4 and 5). An additional finding, confirming the relationship between mutations in PTC and the disease, was identification of a frameshift mutation in a sporadic NBCCS patient that was not present in either of her unaffected parents (FIG. 5).

Figure 6A:
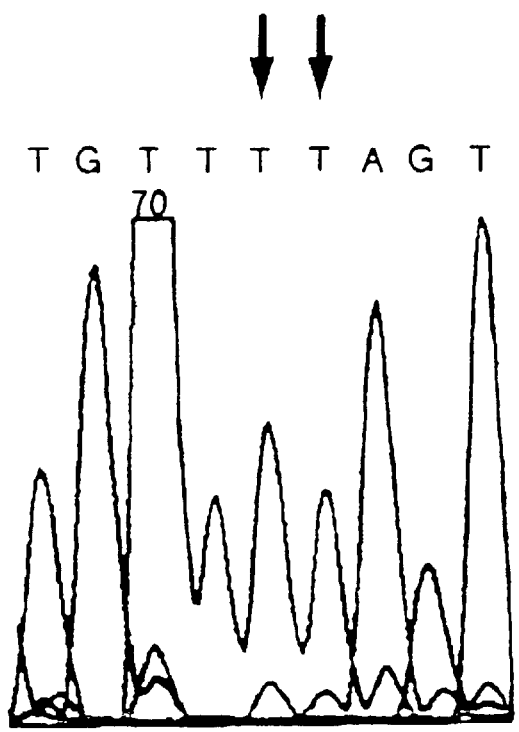
(FIG. 6A) CC to TT mutation (SEQ ID NO:77) in the remaining allele with allelic loss of the NBCCS region. This DNA alteration, which results in a premature stop, is typical of ultraviolet B mutagenesis.
Figure 6B:
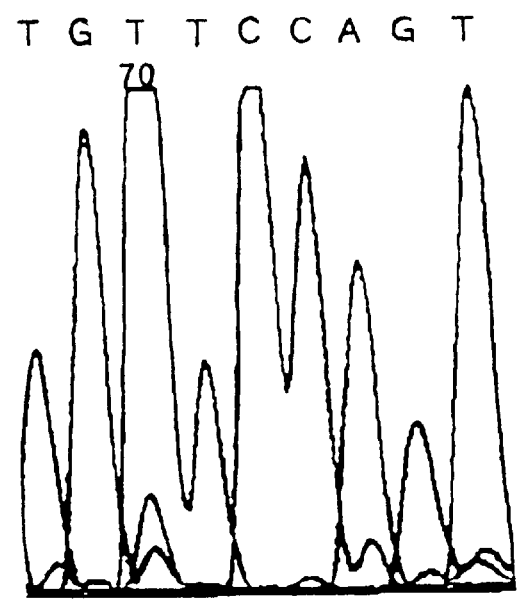
(FIG. 6B) Constitutional DNA from the patient has a normal sequence (SEQ ID NO:78).
Figure 7:
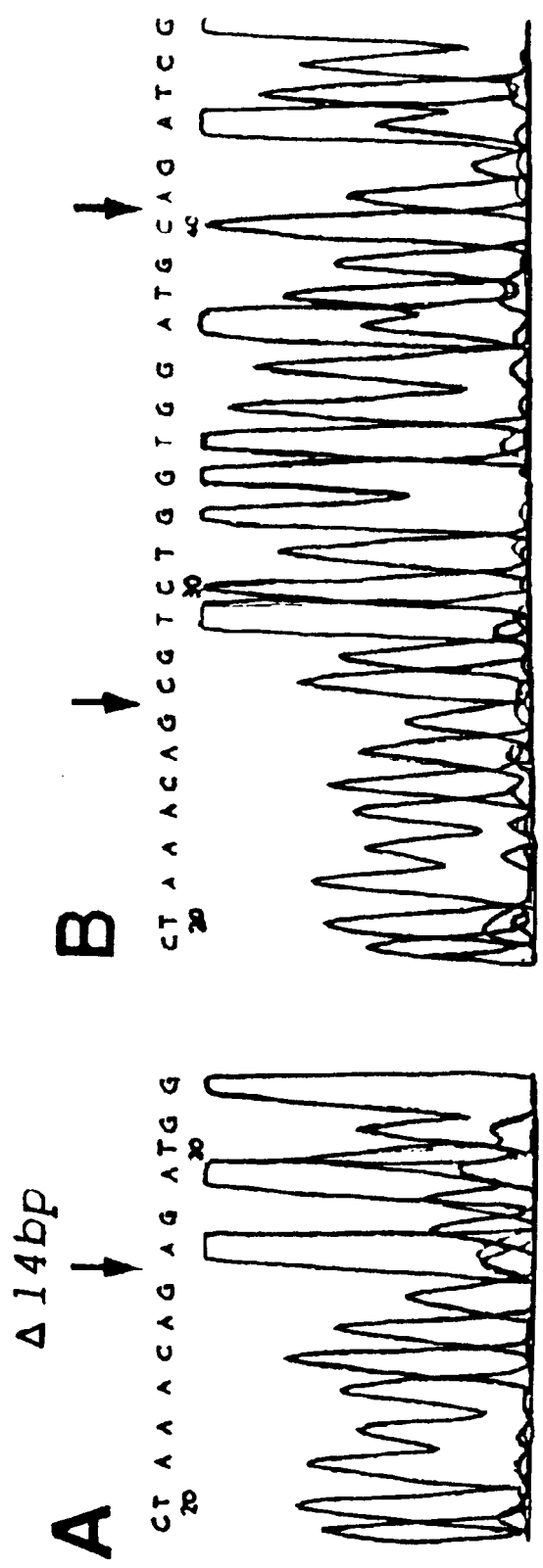
FIG. 7 shows a PTC deletion in a sporadic BCC.

To analyze the role of PTC in neoplasia, tumors related to the syndrome were screened for mutations. Two sporadic basal cell carcinomas with allelic loss of the NBCCS region had inactivating mutations of the remaining allele (FIGS. 6 and 7). A tumor removed from the cheek had a CC to TT alteration, typical of UVB mutagenesis. The second tumor from the nose had a 14 bp deletion, a mutation that cannot be related to any specific environmental accident. Mutations have not yet been identified in any sporadic BCC not showing allelic loss of chromosome 9q22, and alternative modes of pathogenesis may be operative in these neoplasms.

TABLE 2

Primers to amplify PTC exons.

| Exon | Position[a] | Exon Size (bp) | Primer Name | Primers[b] | SEQ ID NO: |
|---|---|---|---|---|---|
| 1 | 1–189 | 189 | PTCF18 | GAAGG CGAGC ACCCA GAC | 10 |
| | | | PTCR18 | TCTTT CCCTC CTCTC CCTTC | 11 |
| 1A | alternate first exon | >239 | PTCF22 | GCTAT GGAAA TGCGT CGG | 12 |
| | | | PTCR22 | CAGTC CTGCT CTGTC CATCA | 13 |
| 2 | 190–382 | 193 | PTCF19 | GTGGC TGAGA GCGAA GTTC | 14 |
| | | | PTCR19 | TTCCA CCCAC AGCTC CTC | 15 |
| 3 | 383–582 | 200 | PTCF27 | CTATT GTGTA TCCAA TGGCA GG | 16 |
| | | | PTCR27 | ATTAG TAGGT GGACG CGGC | 17 |
| 4 | 583–642 | 60 | PTCF20 | AGAG AA AT TTTT GTCT CTGC TTTT CA | 18 |
| | | | PTCR20 | CCTGA TCCAT GTAAC CTGTT TC | 19 |
| 5 | 643–734 | 92 | PTCF21 | GCAAA AATTT CTCAG GAACACC | 20 |
| | | | PTCR21 | TGGAA CAAAC AATGA TAAGCAA | 21 |
| 6 | 735–933 | 199 | PTCF15 | CCTAC AAGGT GGATG CAGTG | 22 |
| | | | 18R2 | TTTGC TCTCC ACCCT TCTGA | 23 |
| 7 | 934–1055 | 122 | 11e18F | GTGAC CTGCC TACTA ATTCCC | 24 |
| | | | 18R3 | GGCTA GCGAG GATAA CGGTTTA | 25 |
| 8 | 1056–1203 | 148 | PTCF2 | GAGGC AGTGG AAACT GCTTC | 26 |
| | | | PTCR2 | TTGCA TAACC AGCGA GTCTG | 27 |
| 9 | 1204–1492 | 288 | PTCF23 | GTGCT GTCGA GGCTT GTG | 28 |
| | | | PTCR23 | ACGGA CAGCA GATAA ATGGC | 29 |
| 10 | 1493–1591 | 97 | PTCF5 | GTGTT AGGTG CTGGT GGCA | 30 |
| | | | PTCR5 | CTTAG GAACA GAGGA AGCTG | 31 |

TABLE 2-continued

Primers to amplify PTC exons.

| Exon | Position[a] | Exon Size (bp) | Primer Name | Primers[b] | SEQ ID NO: |
|---|---|---|---|---|---|
| 11 | 1591–1835 | 245 | PTCF24PT | TCTGC CACGT ATCTG CTCAC | 32 |
|  |  |  | CR24 | CATGC TGAGA ATTGC AGGAA | 33 |
| 12 | 1836–2238 | 403 | PTCF16 | GGCCT ACACC GACAC ACAC | 34 |
|  |  |  | PTCR16 | TTTTT TTGAA GACAG GAAGA GCC | 35 |
|  |  |  | PTC13R | GTCAG CAGAC TGATT CAGGT | 36 |
|  |  |  | PTC37R | AAGAT GAGAG TGTCC ACTTCG | 37 |
| 13 | 2239–2548 | 310 | PTCF14 | GACAG CTTCT CTTTG TCCAG | 38 |
|  |  |  | PTCR14 | ACGCA AAAGA CCGAA AGGAC GA | 39 |
| 14 | 2549–2691 | 143 | PTCF13 | AGGGT CCTTC TGGCT GCGAG | 40 |
|  |  |  | PTCR13 | TCAGT GCCCA GCAGC TGGAG TA | 41 |
| 15 | 2692–2875 | 185 | PTCF7 | AACCC CATTC TCAAA GGCCT CTGTTC | 42 |
|  |  |  | PTCR7 | CACCT CTGTA AGTTC CCAGA CCT | 43 |
| 16 | 2876–3156 | 281 | PTCF12 | AACTG TGATG CTCTT CTACC CTGG | 44 |
|  |  |  | PTCR12 | AAACT TCCCG GCTGC AGAAA GA | 45 |
| 17 | 3157–3294 | 138 | PTCF8 | TTTGA TCTGA ACCGA GGACACC | 46 |
|  |  |  | PTCR8 | CAAAC AGAGC CAGAG GAAATGG | 47 |
| 18 | 3295–3437 | 143 | PTCF11 | TAGGA CAGAG CTGAG CATTT ACC | 48 |
|  |  |  | PTC21R | TACCT GACAA TGAAG TCG | 49 |
| 19 | 3437–3537 | 101 | PTCF11 | TAGGA CAGAG CTGAG CATTT ACC | 50 |
|  |  |  | PTC21R | TACCT GACAA TGAAG TCG | 51 |
| 20 | 3538–3792 | 255 | PTCF25 | AACAG AGGCC CCTGA AAAAT | 52 |
|  |  |  | PTCR25 | GATCA CTTGG TGGGC AGG | 53 |
| 21 | 3793–4330[c] | 537 | PTCF10 | TCTAA CCCAC CCTCA CCCTT | 54 |
|  |  |  | PTC31R | ATTGT TAGGG CCAGA ATGCC | 55 |
|  |  |  | PTCF26 | AGAAA AGGCT TGTGG CCAC | 56 |
|  |  |  | PTCR26 | TCACC CTCAG TTGGA GCTG | 57 |

[a]Positions of exons are shown in bp according to the numbering of the human cDNA sequence (GENBANK #U43148). The size of the exon is known in all cases except for exon 1a, for which the 5' end is not yet defined.
[b]The sequence of the primers is 5'–3'. There is a 45 bp intron between exons 18 and 19, and both exons are amplified with primers F11 and 21R. Updated primer sequences and PCR conditions are available by anonymous FTP (contact dean @fcrfv2.ncifcrf.gov).
[c]Position of the last bp of the final codon.

TABLE 3

Mutations in the PTC gene.

| Sample Type | Inheritance | Exon | Type of Mutation | Designation |
|---|---|---|---|---|
| NBCCS | F | 5 | premature stop | C1081T |
| NBCCS | F | 6 | 37 bp deletion | del 804–840 |
| NBCCS | F | 8 | premature stop | G1148A |
| NBCCS | F | 12 | 2 bp insertion | 2047insCT |
| NBCCS | S | 12 | 1 bp insertion | 2000insC |
| NBCCS | S | 14 | 1 bp deletion | 2583delC |
| BCC | S | 5 | premature stop | CC108ITT |
| BCC | S | 15 | 14 bp deletion | del 2704–2717 |

[a]NBCCS, germline mutations in a patient with the syndrome; BCC, somatic mutation in a basal cell carcinoma.
[b]F, familial; S, sporadic.

Discussion

These examples provide strong evidence that mutations of the NBCCS gene (PTC), the human homologue of Drosophila patched cause the nevoid basal cell carcinoma syndrome. Alterations predicted to inactivate the PTC gene product were found in six unrelated NBCCS patients. Frameshift mutations were found in two sporadic patients but not in their parents, and somatic mutations were identified in two sporadic tumors of the types seen in the syndrome. No known human tumor suppressor has sequence similarity to PTC, and functionally PTC may represent a novel type of neoplasia-related gene.

The Drosophila Patched Gene in Differentiation and Development

The patched gene is part of a signaling pathway that is conserved from flies to mammals. The Drosophila gene (ptc) encodes a transmembrane glycoprotein that plays a role in segment polarity (Hooper and Scott (1989) Cell 59: 751–765; Nakano et al. (1989) Nature 341: 508–513). Many alleles of ptc produce an embryonic lethal phenotype with mirror-image duplication of segment boundaries and deletion of the remainder of the segments (Nusslein-Volhard et al. (1980) Nature 287: 795–801), but hypomorphic alleles produce viable adults with overgrowth of the anterior compartment of the wing, loss of costal structures, and wing vein defects (Phillips et al. (1990) Development 10: 105–114). Genetic and functional studies have shown that one of the wild type functions of ptc is transcriptional repression of members of the Wnt and TGF-b gene families (Ingham et al. (1991) Curr. Opinion Genet. Develop. 5: 492–498; Capdevila et al. (1 994) EMBO J. 13: 71–82. The mechanism of this repression is not known, and many other downstream targets of ptc activity may exist.

The action of ptc is opposed by the action of members of the hedgehog gene family. Studies in Drosophila have demonstrated that hedgehog (hh) is a secreted glycoprotein which acts to transcriptionally activate both ptc-repressible genes and ptc itself (Tabata and Kombernc (1994) Cell, 76: 89–102; Basler and Struhl (1994) Nature, 368: 208–214). Thus, in a given cell type the activity of target genes results from a balance between hedgehog signaling from adjacent cells and ptc activation.

Mammalian Homologues of Patched

The human homologue (PTC) of Drosophila ptc, of this invention, displays no more than 67% identity at the nucleotide level and 61% identity at the amino acid level to the Drosophila gene. Thus identification of a human homolog would have been difficult using either a hybridization approach or by screening an expression library with antibodies to the fly protein. The present data strongly suggest that patched is a single copy gene in mammals.

Figure 3:
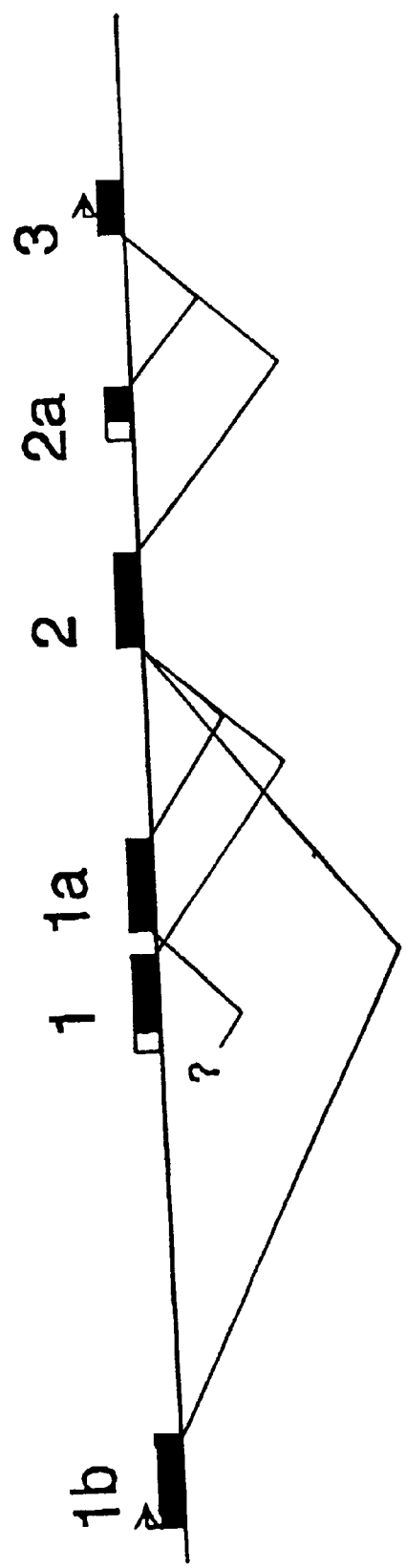
FIG. 3 provides a map of the promoter region of the NBCCS (PTC) gene.

Analysis of fetal brain cDNA clones, and RACE experiments with epidermal RNA revealed the presence of two different 5' ends for the human PTC gene (FIG. 3). The two human sequences diverge from the mouse PTC cDNA (from 8 dpc embryo RNA) at the same position, and the mouse N-terminus more closely matches the Drosophila and C. elegans proteins. Analysis of the upstream genomic sequence of the C. elegans gene failed to reveal any homology to the two alternate human ends. These data suggest that there are at least three different forms of the PTC protein in mammalian cells: the ancestral form represented by the murine sequence, and the two human forms. The first in-frame methionine codon for one of the human forms is in the 3rd exon, suggesting that this form of the mRNA either encodes an N-terminally truncated protein, or uses an alternate initiation codon. The second human form contains an open reading frame that extends through to the 5' end, and may be initiated by upstream sequences that have not yet been isolated. The identification of several potential forms of the PTC protein provides a mechanism whereby a single PTC gene could feasibly play a role in different pathways. It will be important to determine the regulation of the different splice forms of Ptc mRNA as this may shed light on the apparent role of the gene in both embryonic development and growth control of adult cells.

In adult humans PTC is expressed widely. Abundant transcript is found in the kidney, liver, lung, brain, heart, skeletal muscle, pancreas, and skin. During murine development Ptc is expressed first at 8.0 dpc in ventral neuroepithelial tissue in two separate domains along the midline. By day 9.5, transcripts are detected in the mesenchyme surrounding the neural tube as well. Expression is seen in the developing somites in a rostral-caudal gradient. From day 10.0 to 12.5 the transcript is present in the posterior ectoderm of each limb bud. Other sites of expression during this period include the inner surfaces of the pharyngeal arches, cells surrounding the placodes of the vibrissae, and the genital eminence.

Several homologues of Drosophila hedgehog (hh) have been identified in vertebrates and, like the Drosophila gene, appear to be involved in pattern organization during development. The most extensively studied of these is Sonic hedgehog (Shh). In the mouse, expression of Shh is normally detected in the notochord and the overlying floorplate region of the neural tube (Echelard et al. (1993) Cell 75: 1417–30). Apart from being involved in midline signaling in vertebrates, Shh is also expressed in a number of other tissues, including the developing limbs, where it appears that Shh normally mediates the activity of the zone of polarizing activity (ZPA).

The expression of murine Ptc is found in a variety of tissues known to be responsive to Shh signaling. A detailed expression analysis has indicated that the pattern of expression closely follows changes in Shh expression such that the transcripts are found mostly in adjacent, non-overlapping tissues. Ptc may be required for Shh signaling, and hh/ptc interactions appear to have been conserved during evolution. As in flies, Ptc transcription in mouse appears to be indicative of an adjacent hh signal. Accordingly, when interpreting the relationship between known sites of Ptc expression and the NBCCS phenotype, it may be of value to consider the expression pattern of hedgehog gene family members since they have been characterized in much more detail in vertebrates than ptc, specially in adult tissues.

While it is clear that genetically and functionally Ptc responds to hh signaling, its structure does not make it an obvious hh receptor. Rather, it has been proposed that Ptc may be a transporter and the substrates are molecules which regulate the transcription of target genes.

The Role of PTC in Neoplasia

The data presented in this study strongly suggest the NBCCS gene functions as a tumor suppressor. These examples show that germline mutations underlying the NBCCS phenotype are inactivating, and therefore hereditary tumors have no functional copy of the gene. In addition, these examples provide the first direct evidence that sporadic basal cell carcinomas (BCCs) can arise with somatic loss of both copies of the gene. The role of PTC in other tumors related to the syndrome remains to be explored.

That two known targets of ptc repression in Drosophila represent gene families involved in cell-cell communication and cell signaling provides a possible mechanism by which ptc could function as a tumor suppressor. The ptc pathway has recently been implicated in tumorigenesis by the cloning, of the pancreatic tumor suppressor gene, DPC4 (Hahn et al (1996) Science 271: 350–353), which shows sequence similarity to Drosophila mad (mothers against dpp). The mad gene interacts with dpp, a Drosophila TGF-b homologue specifically repressed by ptc.

The cell of origin of BCC has been greatly debated and current theory postulates a progenitor "stem cell" that is slow cycling, but of great proliferative potential (Miller (1991) J. Am. Acad. Dermatol. 24: 161–175). Through occasional cell division "transient amplifying cells" are formed, which further multiply before committing to terminal differentiation. The expression of patched and hedgehog gene family members in skin is not known. In Drosophila, ptc is found in membrane regions resembling cell adhesive junctions, and it colocalizes with PS2 integrins, suggesting that the human homolog may normally play a role in epidermal differentiation based upon cell/cell interactions. The correct localisation of Drosophilaptc protein to these regions is also dependent upon the interaction of the cells in a polarized epithelial sheet, an observation also supporting a role for ptc in cell adhesive structures (Capdevila et al. (1994) Development 120: 987–998). The present finding suggest that BCCs lack intracellular PTC signaling leading to an overexpression of the proliferative and cell/cell communication genes associated with hedgehog signaling. Alternatively, if PTC has a direct role in cell/cell interactions, proliferation may result from disruption at this level.

The Role of PTC in Developmental Anomalies

By analogy to embryonic expression of Ptc in the mouse, many of the features of NBCCS can be correlated with the presumed sites of expression of PTC in the developing human embryo (Table 4). For example, the skeletal anomalies involving the ribs, vertebrae and shoulders are most likely due to disruption of PTC expression in the sclerotome. In the mouse embryo Ptc expression is detected in the ventral-medial cells of the somites, a region which subsequently forms sclerotome (Hahn et al. (1996) supra.; Goodrich et al. (1996) Genes Dev. 10: 301–12). In addition, Shh has been implicated in the induction of sclerotome by long range signaling from the notochord (Fan et al. (1995) Cell 81: 457–465).

TABLE 4

Mouse Ptc expression and human NBCCS phenotype.

| Site of expression in mouse | NBCCS Phenotype |
| --- | --- |
| Pharyngeal arches | Facial malformations |
| | Jaw cysts (dental lamina derivative |
| Neural tube | Dysgenesis of the corpus callosum |
| | Eye anomalies |
| Somites | Spina bifida |
| | Vertebral filsion |
| | Rib anomalies |
| Limb buds | Short fourth metacarpals |
| | Polydactyly |

The polydactyly observed in a subset of NBCCS patients is likely to correlate with the expression of Ptc in the developing murine limb (Hahn et al. (1996) supra.; Goodrich et al. (1996) supra.). While the actual mechanisms remain unknown it seems clear that anterior posterior patterning of the limb is controlled by Shh signaling from the ZPA. In the early mouse limb bud Ptc expression correlates with Shh while at later stages expression is detected in the periphery of the digital condensations in cells adjacent to those expressing Indian hedgehog (Ihh) (Goodrich et al. (1996) supra.) Therefore the polydactyly present in NBCCS may result from perturbation of limb patterning due to modulation of PTC. Similarly the occurrence of immobile thumbs in a small percentage of NBCCS patients is consistent with an alteration to wild type PTC function.

Craniofacial dysmorphology correlates with expression of Ptc in the pharyngeal arches and derived structures. The jaw keratocysts and dental malformations, which are common features of NBCCS, are most likely explained by the observed expression of Ptc in the tooth bud and the enamel knot (Vaahtokari et al. (1996) *MOD*, 54: 39–43; Goodrich et al (1996) supra.). The pathogenesis of jaw cysts is almost certainly related to the embryologic dental precursors. The epithelial lining of keratocysts is believed to arise from aberrant derivatives of the dental lamina, the precursor of tooth buds. The progenitor cells may have migrated abnormally during development of the lamina or failed to involute at the appropriate stage of development.

The neurological components of NBCCS such as agenesis of the corpus collosum, retinal colobomas, and possibly strabismus and macrocephaly are consistent with the expression of Ptc in the developing brain and neural system. Mental retardation, seen occasionally in the syndrome, may be caused by contiguous gene deletions.

Under the classical two-hit model for the action of tumor suppressors (Knudson (1971) *Proc. Natl. Acad. Sci. USA*, 68: 820–823) the finding of developmental defects in a syndrome caused by hemizygous inactivation of this type of gene constitutes a paradox because loss of just one copy is thought to have little or no effect on cell function. It is possible that some of the discrete defects in NBCCS (e.g., spina bifida occulta, bifid ribs, and jaw cysts) can be explained by a two-hit mechanism. Like the neoplasms in cancer predisposition syndromes many of these defects are multiple and appear in a random pattern, but isolated defects of the same type are seen occasionally in the general population. These anomalies might result from homozygous inactivation of PTC in an early progenitor cell of the relevant tissue leading to abnormal migration or differentiation or perhaps failure to undergo programmed cell death. Allelic loss studies have in fact shown that keratocysts of the jaw are clonal abnormalities that arise with homozygous inactivation of the NBCCS gene (Levanat et al. (1996) *Nat. Genetics* 12: 85–87). However, generalized or symmetric features such as overgrowth, macrocephaly, and facial dysmorphology almost certainly defy the two-hit paradigm and are probably due to haploinsufficiency. It appears that many of the developmental defects seen in NBCCS patients result from perturbation of a dosage sensitive pathway during embryonic development. Based upon these observations one prediction would be that a heterozygous Ptc "knock-out" mouse would show relatively mild developmental anomalies and UV irradiation of the skin would result in multiple basal cell carcinomas.

Phenotypic Variation in NBCCS

NBCCS is a disorder with almost 100% penetrance, but many of the features show variable expression. An interesting correlate in Drosophila is that flies homozygous for non-lethal alleles show striking variability in expression of phenotypic features. Because these flies are isogenic, the phenotypic differences cannot be explained by different underlying, mutations or modifying genes (Phillips et al. (1990) supra.). Presumably the variability is a stochastic effect.

That there is more similarity in the human NBCCS phenotype within families than between families (Anderson et al. (1967) supra.) suggests that there may be some degree of genotype/phenotype correlation. At present there are no clearly defined patterns of mutation distribution in NBCCS and all mutations found so far are predicted to cause truncation of the PTC protein. In families with BRCA1 termination mutations, ovarian cancer is more common in patients with 5' mutations, perhaps because mutant peptides may retain some wild-type function in some cell types but not in others (Gayther et al. (1995) *Nature Genetics* 11: 428–433).

Example 3
Characterization of PTCH Germ Line Mutations in NBCCS
Materials and Methods
DNA Extraction Odontogenic keratocyst tissue was placed in 200 μl STE buffer (50 mM NaCl; 10 mM Tris-HCl pH8.0; 1 mM EDTA) containing 0.5% w/v SDS, 1 μg/μl proteinase K and incubated at 37° C. for 24 hours. Following inactivation of the proteinase K at 95° C. for 15 minutes, a sample of 1–5 μl (approximately 25 ng DNA) was used directly for PCR. Constitutional DNA was obtained from peripheral blood lymphocytes or buccal epithelial cells using standard DNA extraction procedures. Approximately 25 ng DNA was used directly for PCR.

Genbank Accession Numbers

DNA sequence data for the PTCH gene are available under accession numbers U43148 and U59464. The nucleotide numbering used in this Example corresponds to sequence U43148, whereas the amino acid residue numbering corresponds to U59464.

PCR-SSCP Analysis of the PTCH Gene

Each of the 23 exons comprising the patched gene were amplified separately using the primers and annealing conditions described in Hahn et al. (1996), supra. In brief, approximately 25 ng target DNA was amplified in 30 μl 1×PCR reaction buffer containing 50 mM KCl; 10 mM Tris-HCl (pH 9.0); 1.5 mM $MgCl_2$; 0.1% v/v Triton X-100; 200 μM each dATP, dGTP, dTTP, 20 μM dCTP; 10 picomoles of each primer; 1.0 μCi [$\alpha^{32}$P-dCTP] and 1.0 unit Taq. DNA polymerase (Promega, UK). Following 35 cycles of amplification, 5 μl PCR product was added to 35 μg 10 mM EDTA, 0.1% w/v SDS. 2 μl of this was added to 2 μl loading buffer containing 95% v/v deionised formamide/20 mM EDTA/0.05% w/v bromophenol blue/0.05% w/v xylene cyanol, heated to 100° C. for 5 minutes, quenched on ice and loaded onto a 1×TBE/6% w/v non-denaturing polyacrylamide gel (5%C) containing (5%C) containing 5% v/v glycerol. Electrophoresis was at 350V for 18 hours. Gels were dried under vacuum and autoradiographed for 16 hours at room temperature with intensifying screens.

Restriction SSCP

PCR products obtained by amplification of exons 14 and 17 were restriction enzyme digested with AluI and HinfI, respectively, prior to SSCP analysis. An aliquot of 10 μl PCR product was digested in a total volume of 20 μl 1× reaction buffer according to manufacturers' instructions. 2 μl of restriction enzyme digested PCR product was mixed with 2 μl loading buffer and subjected to SSCP analysis as described above.

DNA Sequencing of PTCH Exons

Exonic PCR products displaying altered mobilities by SSCP analysis were purified using commercially available columns (Wizard PCR columns, Promega). PCR products were eluted in 20 μl TE and 2 μl used for DNA Thermosequenase (Amersham International plc) cycle sequencing according to manufacturer's instructions. Sequencing primers were end-labelled with $\gamma^{32}$P-ATP (3000 Ci/mmol) using T4 polynucleotide kinase. DNA sequencing reactions were fractionated in 6% w/v polyacrylamide/8M urea/1×TBE gels for 2 hours at 2000V. Gels were dried under vacuum and autoradiographed for 8 hours at room temperature with intensifying screens.

Results

Keratocyst DNA from a total of 16 NBCCS patients was screened by SSCP-PCR. 10 single exonic PCR products displaying altered electrophoretic mobilities were detected and analyzed further by DNA sequence analysis. In addition, variant bands in multiple samples (i.e. indicative of common polymorphisms) were also seen in PCR products encompassing 4 exons.

Four mutations were identified following direct DNA sequencing of PCR amplified exons displaying SSCP variant bands. Mutations could not be detected in the remaining 6 variant PCR products. Therefore, all 23 exons from the samples in which a mutation had not been identified initially were amplified and sequenced in their entirety. However, only one additional mutation was detected by this method.

Exon 5 693 insC

A single cytosine residue insertion at position 693 was detected in a 42 year old male NBCCS patient. This introduces a frameshift mutation by the creation of a premature stop codon at amino acid residue 252. This mutation also creates a BstNI restriction enzyme site. DNA from the patient and 4 unaffected family members was amplified and restriction enzyme digested with BstNI. As predicted, only the product from the NBCCS patient was cut by the restriction enzyme.

Exon 17 2988 del8bp

Following HinfI restriction enzyme digestion of exon 17 PCR products and SSCP analysis, 2 variant bands were seen. Direct DNA cycle sequencing of these amplicons revealed 2 mutations. An 8 bp deletion was detected in DNA from a 12 year old male NBCCS patient. This frameshift mutation introduces a stop codon at amino acid residue 1141. The patient has macroephaly, hypertelorism, supra-orbital ridges, prognathism, plantar but not palmar pitting and an accessory nipple. In addition, at age 10 years, the patient had undergone surgical removal of 3 maxiallary and mandibular odontogenic keratocysts.

Exon 17 3014 insA

An adenosine insertion at base 3014 was detected in an 18 year old female NBCCS patient. This results in a frameshift mutation (tyrosine to STOP) codon at amino acid residue 1009. This patient was frontal bossing, hypertelorism, falx calcification, bifid 3rd, 4th, 5th and 6th ribs and has undergone enucleation of 5 maxillary and mandibular odontogenic keratocysts.

Exon 21 3538 de1G

A guanosine base deletion at residue 3538 was identified in a 38 year old female NBCCS patient. This frameshift mutation introduces a stop codon at amino acid residue 1190. The causal nature of the mutation was confirmed by analysis of DNA from the proband's father, from whom she has inherited the disorder. Direct DNA sequencing of exon 21 from the father also revealed a guanosine base deletion at residue 3538.

Exon 22 G4302T

Direct DNA sequencing of 23 exons from a 30 year old female NBCCS patient revealed a G-T substitution at nucleotide 4302. This causes a glutamic acid to aspartic acid (E-D) substitution at amino acid residue 1438. The patient has been confirmed as a case of NBCCS and has undergone removal of 11 basal cell carcinomas.

PTCH Gene Polymorphisms

Using the SSCP conditions described, the inventors observed polymorphisms in PCR products amplified from exons 6, 11, 14 and 15. No DNA sequence alterations were detected following analysis of exonic sequences. Therefore, it is likely that these represent intronic DNA sequence polymorphisms. Also, an exonic DNA sequence polymorphism (C306T) was disclosed in exon 2. This base substitution was observed in DNA from subject LDI-1, in which a "causative" 3538de1G mutation had already been identified, as well as other unrelated NBCCS patients.

In this example, the inventors identified 5 novel, germ line mutations from patients with the NBCC cell, consistent with the role of patched as a human tumour suppressor gene. Four mutations cause frame-shift or non-sense mutations resulting in a truncated PTCH protein; the fifth mutation is a glutamic acid to aspartic acid substitution close to the 3'-carboxyl terminus of the PTCH protein. This was the only base change detected following direct DNA sequencing of all 23 PTCH exons from patient #5. Although this represents a conservative amino acid substitution and, therefore, may be a polymorphism and not a mutation, this glutamic acid residue is conserved between human, mouse and chicken PTCH proteins and is likely to be functionally important.

Example 4

Mutations of the Ptc Gene in NBCCS Define Clinical Phenotype

Example 3 defined mutations in individuals with NBCC syndrome. In this Example, further mutations are identified.

Materials and Methods

The patients were diagnosed according to the clinical criteria of Shanley et al (1994). Seventy NBCCS patients were fully analyzed by single strand conformation polymorphism (SSCP) and heteroduplex analysis as previously described (Hahn et al., supra.) with primers for all coding exons except for exon I b (alternative first exon). Primer sequences were as hereinbefore described as well as Hahn et al (1996) with the exception of exons 12, 12b and 20. Exon 12b is an additional exon resulting from the discovery that exon 12 (Hahn et al. 1996) consists of two distinct exons. The PTC gene, therefore, consists of 23 coding exons. Where possible, DNA was also analyzed from the parents of cases in which PTC mutations were found in order to determine at a molecular level whether the mutation was sporadic or familial. Any samples showing SSCP variants were sequenced as previously described (Wicking et al. (1997) *Am. J. Hum. Genet.* 60: 21–26).

Paternity testing was carried out using microsatellite markers in the parents of the eight sporadic cases using fluorescent primers and Genescan.
Results PTCH mutations were identified in a total of 32 NBCCS cases. Twenty-eight of these are described in Example 3. This Example presents four novel mutations (Table 5). Of these, three are frameshift mutations and one is a putative splice variant. The inventors have, therefore, detected PTCH mutations in 32/70 (46%) NBCCS cases by analysis of all exons except exon lb. The majority of these (27/32; 84%) are

TABLE 5

PTCH MUTATIONS IN NBCCS INDIVIDUALS

| Patient | Exon | Mutation | Effect on coding |
|---|---|---|---|
| JK211 | 12 | 1711insC | Frameshift, truncation |
| MB229 | 12 | 1639insA | Frameshift, truncation |
| CW424 | 16 | 2707delC | Frameshift, truncation |
| NB88 | Intron 17 | 3157-2A->G | Putative splice variant |

TABLE 6

MUTATIONS OF PTCH IN NBCCS PATIENTS

| Patient | Mutation | Effect | Parental phenotype |
|---|---|---|---|
| DD25 | C2050T | Nonsense | Parents both clinically and radiologically negative but multiple BCCs in history of grandmother. |
| JHG547 | C391T | Nonsense | Father has had > 10 BCCs from 6th decade but radiologically negative. Mother clinically and radiologically negative. |
| BK273 | 244delCT | Frameshift | Father has high arched palate, macrocephaly and dense falcine calcification (age 53) but below maximum biparietal diameter. The Mother clinically and radiologically negative. |
| JHK551 | 271insA | Frameshift | Negative family history but neither parent examined. |
| JRN250 | 929delC | Frameshift | Both parents clinically and radiologically negative. |
| MP264 | 2183delTC | Frameshift | Father has high arched palate, macrocephaly and three "pits" on soles but radiologically negative. Mother clinically and radiologically negative. |
| KS356 | 2583delC | Frameshift | Father has had three unconfirmed BCCs (age 65) but radiologically negative. Mother negative clinically. No radiological examinations. |
| JK211 | 1711insC | Frameshift | Father has high arched palate and has had about 20 BCCs (from age 70) but also multiple solar keratoses, keratoacanthoma and squmous cell carcinomas. He is radiologically negative. Mother clinically and radiologically negative. | protein terminating mutations. In addition, eight sporadic cases were identified by the absence of the relevant disease-associated mutation in either parent (Table 6). Paternity testing was performed in these eight cases, using four microsatellite markers and in none was any inconsistency identified.

This Example presents eight individuals with NBCCS whom the inventors have shown to carry mutations in the PTCH gene. In all cases, the parent did not carry the disease-related mutation, and non-paternity was shown to be unlikely by analysis of highly informative microsatellite markers. In addition, the inventors report four NBCCS individuals with germline PTCH mutations. Three out of four of these would result in premature protein truncation.

The ability to confirm the diagnostic status of relatives of NBCCS cause by DNA analysis allows further definition of the clinical and radiological criteria used to diagnose NBCCS. Of the eight NBCCS individuals shown to have new mutations in the PTCH gene in this study only two (JRN250, DD25) clearly represented sporadic cases based on clinical and radiological examination of both parents. In one case (JHK551) neither parent had been examined. In all other cases one parent showed at least one feature associated with NBCCS such as multiple BCCS, a high arched palate or macroephaly.

Example 5
Medulloblastomas of the Desmoplastic Variant Carry Mutation of the Human Ptc Gene In this Example, the inventors detected non-conservative PTC mutations in three of 11 sporadic cases of desmoplastic medulloblastomas (Mbs) but none in 57 tumours with classical (non-desmoplastic) histology. In two of the tumours with mutations and in two additional desmoplastic cases, LOH was found at 9q22. These findings suggest that PTC represents a tumour suppressor gene involved in the development of the desmoplastic variant of MB.

Materials and Methods
Patient and Tumours, Cell Lines

A total of 68 medulloblastoma samples were analyzed, 64 samples were obtained from MB tumors and 4 from the previously described medulloblastoma cell lines D283Med, D341Med, Daoy, and MHH-MED-1 (Pietsch et al. (1994) Cancer Res. 54: 3278–3287). In two patients, the inventors were able to study both the primary and the recurrent tumors. Constitutional DNA from peripheral blood was available in 40 patients. DNA samples from peripheral blood from healthy Caucasian volunteers were used as controls. A sample of normal cerebellum was analyzed. This biopsy specimen was from an adult patient with a cerebellar vascular malformation and was found to be normal upon histopathological review. The patients' age ranged from 1 month to 59 years; there were 46 males and 20 females. None of the patients had clinical signs of NBCCS or had first degree relatives with NBCCS. All tumors were diagnosed according to the revised WHO classification of brain tumors using standard histological methods including HE and reticulin stains and immunohistochemical reactions (Kleihues et al. (1993) *Histological typing of tumours of the central nervous system,* Springer Verlag, New York). Differentiation was assessed by immunostaining for embryonal neural cell adhesion molecule (NCAM), neuron-specific enolase, synaptophysin and glial acidic fibrillary protein. Frozen tumour samples were obtained at the time of surgical resection, snap frozen in liquid nitrogen and stored at −80° C.

DNA Extraction, LOH Analysis

Tumour fragments were selected for extraction of DNA after careful examination of corresponding frozen sections to exclude contaminating necrotic debris or normal cerebellar tissue and to determine the histological characteristics of the tumors. DNA was extracted by standard proteinase K digestion and phenol/chloroform extraction (Albrecht et al, 1994). Loss of heterozygosity was determined by microsatellite analysis with the markers D9S287 and D9S197 which were tightly linked to the PTC gene and with two additional markers on 9q (D9S302, D9S303) essentially as previously described (Albrecht et al. (1994) *Neuropathol. Appl. Neurobiol.* 20:74–81; Kraus et al. (1996) *Int. J. Cancer* 67: 11–15).

SSCP Analysis and DNA Sequencing

SSCP analysis of exons 2–22 was performed using 22 primer pairs (previous Examples and Hakin et al, 1996). PCR containing 50 mM KCl, 1.0–2.5 mM $MgCl_2$, 10 mM Tris-HCl (pH 8.5), 0.01% w/v gelatin and 200 mM of each dNTP, 2 $\mu$M of the primers and 0.25 units Taq polymerase (Gibco-BRL) on a Uno Thermoblock cycler (Biometra). The products were analyzed on polyacrylamide gels with different acrylamide concentrations and acrylamide/bisacrylamide ratios. Gel composition and electrophoresis conditions were optimized for each individual primer pair. The single and double strands were visualized by silver staining as previously described (Albrecht et al, 1994). PCR products which showed a gel mobility shift were excised from the wet gel, eluted (Koch et al, 1996) and reamplified by PCR with the same primers. The resulting products were purified using spin columns (Qiagen quick spin), and 20 ng used to cycle sequencing with a fluorescent dideoxy terminator kit (ABI). The products were analyzed on an Applied Biosystems model 373A DNA sequencer.

Isolation of RNA, Quantitative RT-PCR for PTCH mRNA

Figure 10A:
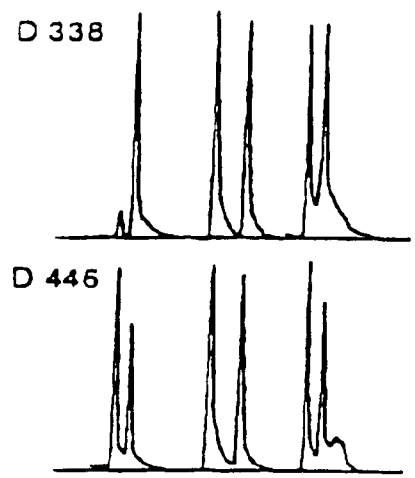
FIG. 10A: PTC mRNA expression in two representative tumors of the classical variant of MB.
Figure 10B:
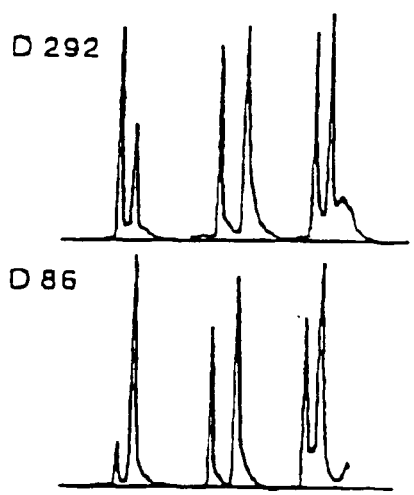
FIG. 10B: expression in desmoplastic MBs.
Figure 10C:
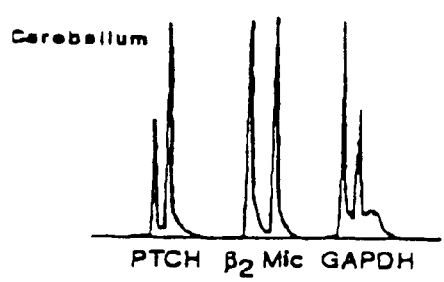
FIG. 10C: expression in adult human cerebellum.

Total cellular RNA was extracted by lysis in guanidinium isothiocyanate and ultracentrifugation through a cesium chloride cushion (Koch et al, 1996) or by extraction with the Trizol™ reagent (Gibco-BRL) following the manufacturer's instructions. Again, individual samples were preexamined by frozen section histology to document the histopathological appearance of the specimen. Contaminating residual genomic DNA was removed by digestion with RNAse free DNAse (Boehringer). RNA standards with internal deletions for human PTC and the housekeeping genes $\beta_2$-microglobulin and GAPDH were generated by in vitro mutagenesis and in vitro transcription (Horton and Pease (1991) in *Direct Mutagenesis—A Practical Approach,* McPerson, ed., pp. 217–247 (IRL Press, Oxford). In order to achieve a semi-quantitative assessment, pre-evaluated amounts of the specific standards RNAs covering the equimolar range of the corresponding mRNA transcripts were added to the MB sample RNAs which were then reverse transcribed using the SuperScript™ Preamplification System (Gibco-BRL) with random hexamers as primers in a final volume of 10 $\mu$l. 0.5 $\mu$l of the cDNA was used as a template in RT-PCR reactions for amplification of PTCH, and the housekeeping genes. The primers used were: PTCH, 5'ACATGTACAACAGGCAGTGG-3 [SEQ ID NO:61] and 5'-GCAAGGAGGTTTACCTAGG-3' [SEQ ID NO.62], product size, wild type 192bp, standard 182 bp; GAPDH, 5'-TGCCAAGGCTGTGGGCAAGG-3' [SEQ ID NO:63] and 5'-GCTTCACCACCTTCTTGATG-3' [SEQ ID NO:64] product size, wild type 152bp, standard 142bp; $\beta_2$-microglobulin, 5'-GCTGTGACAAAGTCACATGG-3' [SEQ ID NO:65] and 5'-GATGCTGCTTACATGTCTCG-3' [SEQ ID NO:66], product size, wild type 148bp, standard 130bp. One of the primers for each gene was labeled with a fluorescent dye. All primers were chosen from adjacent exons spanning intronic sequences in order to avoid signals of the cDNA product size caused by residual genomic DNA. The PCR products were separated and analyzed on an Applied Biosystems model 373A DNA sequencer using the Genescan software (ABI). The expression levels of the individual genes were calculated from the signal ratios of the samples to the standards. The relative expression of PTCH mRNA to the housekeeping genes was defined as the ratio of the respective expression levels (FIG. 10).

Figure 9A:
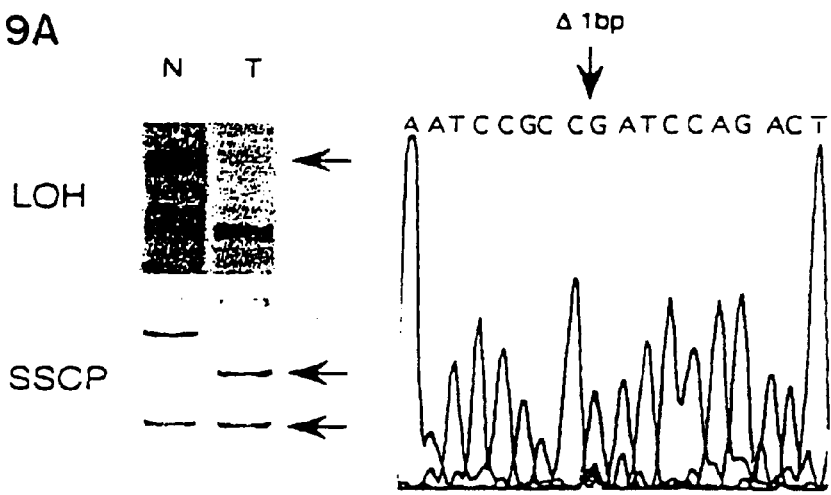
FIG. 9A: microsatellite D9S302 shows loss of heterozygosity in tumor D322. In this tumor, the remaining allele of exon 6 exhibits an altered mobility. DNA sequencing shows a single base pair deletion in the tumor DNA which results in a frameshift and resulting truncation of the PTC protein (SEQ ID NO:81).
Figure 9B:
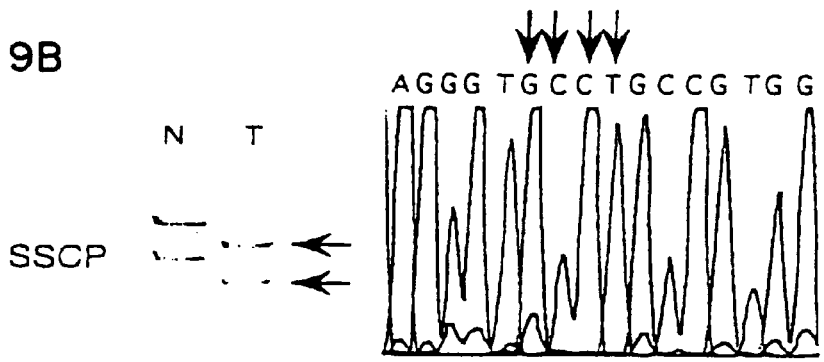
FIG. 9B shows SSCP variants in exon 10 in tumor D292 without allelic loss of chromosome 9q. Sequencing of the altered allele shows a four base pair insertion at position 1393 (SEQ ID NO:82).
Figure 9C:
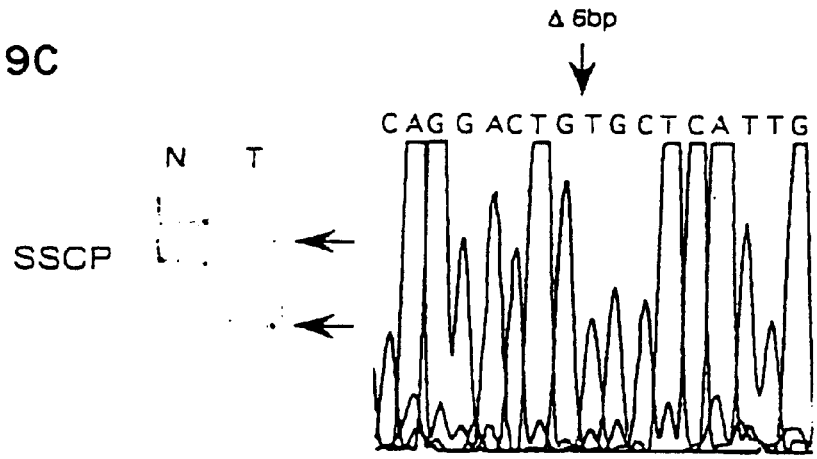
FIG. 9C shows the sequencing of exon 10 in tumor D86 (SEQ ID NO: 83). This tumor, which has LOH, has a six base pair in-frame deletion at position 1444 (CTG GGC). This leads to a deletion of two amino acids (glycine and leucine) in transmembrane region 3.

The human PTCH gene spans 34 kB and has at least 23 exons. SSCP screening of DNA samples from 68 sporadic MBs revealed band shifts in 6 samples (Table 7). Three of these were identified as silent polymorphisms. In three other tumors, the variants were not found in the corresponding germline DNA or in normal control DNA samples. Two mutations in exons 6 and 10, respectively, resulted in a frame shift with premature truncation of the protein (Table 7 and FIG. 9). The third mutation (D86) was a six base pair in frame deletion in exon 10 leading to the deletion of two amino acids in transmembrane region 3. This deletion may cause significant structural alterations of the PTCH protein and may result in loss of function. This was the case in tumours D86 and D322 which showed LOH as well as mutated PTC allele. In case D292 without detectable LOH at 9q, only a single SSCP band shift was found (in exon 10). Mutations of the other allele may be present but may not have been detected by SSCP screening because of the limited sensitivity of SSCP. Only the coding exons were screened so that mutations in other regions such as regulatory domains would not have been identified with this approach. A systematic sequencing analysis may uncover additional PTCH mutations in Mbs.

In this Example, mutations were detected in a distinct histopathological variant or medulloblastomas (MB), the so-called modular or "desmoplastic" MB. According to the WHO classification this variant is characterized by islands of lower cellularity surrounded by densely packed, highly proliferative cells which produce a dense intercellular reticulin fiber network. The more frequent "classical" MB lacks this nodular appearance and reticulin pattern.

TABLE 7

MUTATIONAL ANALYSIS of the PTCH GENE IN MEDULLOBLASTOMAS

| Tumour | MB variant | Age/sex | LOH on 9q | Exon | Nucleotide change | Protein change |
|---|---|---|---|---|---|---|
| a, Mutations | | | | | | |
| D 86 | desmoplastic | 4 y, male | yes | 10 | 1444del6 | del Gly-Leu |
| D 292 | desmoplastic | 1 y, female | no | 10 | 1393insTGCC truncation | frameshift, |
| D 322 | desmoplastic | 51 y, male | yes | 6 | 887delG truncation | frameshift, |
| b, Polymorphisms | | | | | | |
| D 230 11 | classical | 13 y, female | no | 13 | C2037T | no |
| D 338 | classical | 13 y, male | n.a. | 2 | C306T | no |
| D 358 | classical | 10 y, female | n.a. | 2 | C306T | no |

TABLE 8

EXPRESSION OF THE PTCH GENE IN MEDULLOBLASTOMAS

| Sample | MB subtype | LOH on 9q | PTCH mutation detected by SSCP | mRNA expression ratio PTCH/GAPDH | mRNA expression ratio PTCH/$\beta$2-microglobulin |
|---|---|---|---|---|---|
| D 338 | classical | n.a.* | no | 5.8(3.9-7.4)** | 10.3(8.2-14.2) |
| D 230 II | classical | no | no | 1.7 | n.a. |
| D 286 | classical | n.a. | no | 1.2 | n.a. |
| D 245 II | classical | no | no | 0.7 | n.a. |
| D 446 | ciassical | no | no | 1.8(0.8-2.8) | 1.5(1.0-1.8) |
| D 447 | classical | no | no | 0.6 | n.a. |
| D 86 | desmopl. | yes | yes, exon 10 | 3.6(1.4-5.4) | 2.6(1.7-3.9) |
| D 292 | desmopl. | no | yes, exon 10 | 0.6(0.6-0.6) | 0.3(0.3-0.4) |
| D 322 | desmopl. | yes | yes, exon 6 | 1.1 | n.a. |
| D 448 | desmopl. | yes | no | 4.3(3.3-5.5) | 2.9(2.5-3-6) |
| D 398 | desmopl. | no | no | 26.5(22.4-30.0) | 18.4(12.0-24.4) |
| D 444 | desmopl. | yes | no | 4.1(3.7-4.7) | 4.5(3.3-5.5) |
| D 365*** | desmopl. | n.a. | no | 0.3(0.2-0.4) | 0.1(0.1-0.2) |
| Cerebellum - | | n.a. | n.a. | 2.5(1.55-3.64) | 1.76(1.42-2.09) |

*n.a., not analyzed;
**mean and range of relative expression (analyzed by semi-quantitative RT-PCR);
***D365, cell line Daoy.

Example 6

Most Germ Line Mutations in the NBCCS Gene Lead to a Premature Termination of the PATCHED Protein

In this Example, the inventors screened DNA samples from 71 unrelated NBCCS individuals for mutations in the PTCH exons using single strand conformational polymorphism (SSCP) analysis. In total, 28 mutations were identified and characterised by direct sequencing of PCR products. The majority of these mutations (86%) lead to premature truncation of the PTCH protein. Analysis of phenotype in individuals with truncating mutations revealed no statistically significant correlation between genotype and phenotype in NBCCS.

Materials and Methods

Subjects and Samples

The patients, most of whom were from Australia and New Zealand, were diagnosed according to the clinical criteria in Shanley et al. (1994) supra. Of the 71 NBCCS patients analyzed 25 show clear familial presentation and 46 are apparently sporadic.

SSCP Analysis

A combined SSCP and heteroduplex analysis was performed as previously described (Hahn et al. (1996) supra). DNA from 71 unrelated NBCCS individuals was amplified with primers to all but exons 1b (alternative first exon homologous to murine exon 1), 12 and 20 (for which acceptable primers are not yet available) of the human PTCH gene. Primer sequences and conditions were as hereinbefore described as well as (Hahn et al. (1996) supra.).

Sequencing

DNA from samples showing SSCP variants was reamplified and purified for automated sequencing using PCR Spinclean Columns (Progen Industries). DNA concentration was ascertained by agarose gel electrophoresis and 25–35ng of product was used for each automated sequencing run. Cycle sequencing was performed using Amplitaq FS polymerase and dye labelled terminator chemistry (Perkin Elmer Cetus), and samples were analyzed on an PEC 373A electrophoresis apparatus. Where mutations were confirmed by manual sequencing the purified products were ligated into GEM-T vector (Promega) and the resulting clones were sequenced with a T7 Sequencing Kit (Pharmacia).

Southern Analysis

Southern blots were made as previously described (Chenevix-Trench et al 1992), using EcoRI and HindIII restriction enzymes and hybridized with PTCH cDNA probes 13B and 16C.

Statistical Analysis

Linear regression analysis was used to examine genotype-phenotype associations.

Results

Identification of PTCH Mutations

Figure 11:
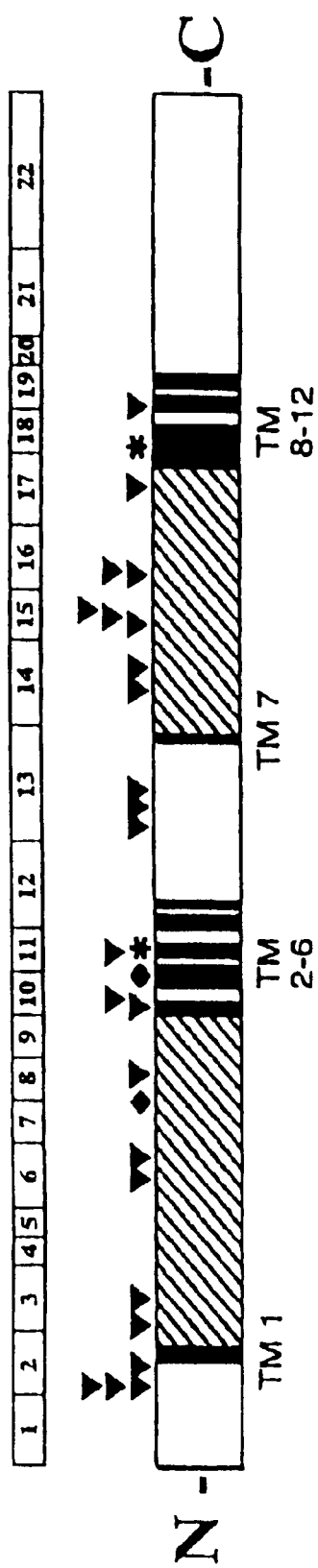
FIG. 11 is a schematic diagram of the PTC protein with the location of germ line mutations indicated. The putative transmembrane domains are designated "TM1" to "TM12"; the hatched boxes represent the two putative extracellular loops. An asterisk (*) denotes a missense; a triangle (▼) denotes a nonsense or frameshift; and a diamond (♦) denotes putative splicing variants. Open boxes above correspond to exons encoding relevant domains.

DNA from 71 individuals with NBCCS was screened for mutations in the PTC gene by a combined SSCP/heteroduplex analysis. Based upon sequencing of samples showing SSCP variation, 28 putative disease-associated mutations have been fully characterised (Table 9). While one mutation, a CT deletion at nucleotide position 244, was seen in 3 apparently unrelated individuals, all other mutations were only detected in a single NBCCS family. No clustering of mutations has been observed, with mutations identified in most exons and in positions corresponding to all of the major domain types of the PTC protein (FIG. 11).

The majority (24/28; 86%) of mutations detected are predicted to result in truncation of the PTCH protein either by introduction of a stop codon or by frameshift due to insertion or deletion (Table 9). Two of the mutations were predicted to be splice variants based on the fact that one altered a consensus 3' splice site, while the other involved an insertion of 21 bp in intron 10, 8 bp upstream of the start of exon 11. This second mutation was presumed to cause aberrant splicing based on the fact that it moves the branch site from position 27 to 48 bp upstream of the 3' splice site. This 7 bp consensus sequence is generally located approximately 18 to 37 bp upstream of the splice site, and its location is considered to be important in the splicing reaction. The remaining two mutations are missense mutations which both alter residues within transmembrane domains of the PTCH protein. One (PP) is a transversion of GAT to TAT at nucleotide 1525, substituting a tyrosine for an aspartate in the fourth transmembrane domain; the other (RS) is a transversion of a GGC to CGC at nucleotide 3193, substituting an arginine for a glycine in the ninth transmembrane domain of the PTCH protein.

In addition to disease-associated mutations, several variants were designated polymorphisms based on their presence in unaffected individuals, or the finding that the underlying sequence changes did not alter the encoded amino acids. For samples in which no SSCP variation was found, the sequence of each exon of the PTC gene is currently being determined. DNA from 38 patients in which a mutation was not found by SSCP was also examined by Southern analysis using probes which span the gene. Variants were detected in two patients. In each case, a single additional band (3 and 3.75 kb respectively) was seen on HindIII blots. No variants were present in these individuals on EcoRI, BamHI and Pst I digests, therefore, those seen on HindIII blots are unlikely to represent gross rearrangements. The probability of at least one of these variants being a disease-related point mutation is increased by its segregation with disease in a family. No family members were available for study in the case of the second variant. The underlying mutations in these individuals are yet to be determined.

Analysis of Genotype-phenotype Associations

Although most of the mutations found to date are predicted to truncate the protein, it remains to be determined whether all ablate its function. In order to address this, preliminary analysis of genotype-phenotype associations in this complex syndrome was performed, based on the 24 families with protein-truncating mutations. Several aspects of the NBCCS phenotype were used as approximate parameters of disease severity. The inventors examined the number of major features (BCCs, jaw cysts, pitting and falcine calcification) seen in individuals at the time of diagnosis, the age at which the individual manifested BCCs and the age at which jaw cysts were detected. Individuals under the age of 20 years were not included in this analysis due to the age-dependent expression of these features. Similarly, analysis of age of BCC onset was restricted to Australasian patients to limit the influence of ultraviolet exposure in promoting BCC development. When a mutation was known to be present in a number of individuals within a family, phenotypic data were averaged across all relevant family members. No correlations between the age of onset of BCCs ($R^2=0.001$) or jaw cysts ($R^2=0.023$), or the number of major features ($R^2=0.015$), and nucleotide position of the mutation, were found, indicating that for these features at least, there is no clear correlation between phenotype and location of the truncating mutation. Although it was not appropriate to use statistical analyses to compare truncating mutations with missense and splice variants due to the small number of the latter type of mutations, the individuals the inventors have analyzed with missense and splice mutations show a classic NBCCS phenotype and would not be classed as mildly affected.

The phenotypes of individuals in the three families which share a common mutation (244delCT) were evaluated, and shown to vary considerably. All five affected members of family CB have a cleft or very high arched palate but this was not observed in the HC or BK families, both of whom show the typical range of NBCCS features. This suggests that the molecular nature of the PTC mutation is not entirely responsible for the phenotype in NBCCS. Interestingly, BK carries a new mutation of PTC so this mutation must have arisen at least twice.

The inventors have identified mutations in the PTC gene in 28 unrelated individuals with NBCCS and found no evidence of any association between genotype and phenotype. In 24 families with protein-truncating mutations, no significant correlation between phenotype and location of the truncating mutation was found. This differs from breast and ovarian cancer where 3' mutations in the BRCAI gene are less likely to predispose to ovarian cancer than are 5' mutations presumably because of residual activity of proteins resulting from 3' mutations.

TABLE 9

GERM-LINE MUTATIONS IN THE PTC GENE IN NBCCS INDIVIDUALS

| PATIENT[a] | EXON | MUTATION[b] | EFFECT ON CODING[c] |
|---|---|---|---|
| | | Missense | |
| PP(S) | 11 | G1525T | D-Y at 513 |
| RS(S) | 18 | G3193C | G-R at 1069 |
| JHG(S) | 3 | C391T | R-X at 135 |
| JM(F) | 8 | G1148A[d] | W-X at 387 |
| TM(S) | 10 | G1368A | W-X at 460 |
| DD(S) | 13 | C2050T | Q-X at 688 |
| BH(S) | 13 | C2068T | Q-X at 694 |

TABLE 9-continued

GERM-LINE MUTATIONS IN THE PTC GENE IN NBCCS INDIVIDUALS

| PATIENT[a] | EXON | MUTATION[b] | EFFECT ON CODING[c] |
|---|---|---|---|
| PB(F) | 17 | C3015A | Y-X at 1009 |
| *Insertions, Deletions, and Duplications* | | | |
| HC, CB(F); BK(S)[e] | 2 | 244delCT | Frameshift |
| JHK (S) | 2 | 271insA | Frameshift |
| GS (S) | 3 | 464insAC | Frameshift |
| MC (F) | 6 | 804del37[d] | Frameshift |
| JRN (S) | 6 | 929delC | Frameshift |
| DS (F) | 10 | 1370del76 | Frameshift |
| CM (S) | 11 | 1497dup8 | Frameshift |
| MP (F) | 13 | 2183delTC | Frameshift |
| TH (F) | 14 | 2320insA | Frameshift |
| LK (S) | 14 | 2392delA | Frameshift |
| DC (S) | 15 | 2574delA | Frameshift |
| KS (S)[e] | 15 | 2583delC[d] | Frameshift |
| WS (F) | 15 | 2596complex[f] | Frameshift |
| DE (F) | 16 | 2748insC | Frameshift |
| JRD (F) | 16 | 2749dup7 | Frameshift |
| JW (S) | 19 | 3352delAT | Frameshift |
| *Splicing* | | | |
| AE (F) | Intron 7 | A1055-2C | 3' splice site |
| IMc (S) | Intron 10 | 1493-8ins21 | Putative splice variant |
| *Polymorphisms[g]* | | | |
| | 2 | A or T at 312 | No change I108 |
| | 3 | T or C at 417 | No change T143 |
| | 4 | A or G at 588 | No change E200 |
| | 5 | A or G at 723 | No change T245 |
| | 7 | T or C at 1023 | No change G345 |
| | Intron10 | G or C at 1493 − 39 | |
| | Intron11 | A or T at 1591 + 29 | |
| | Intron18 | delTT at 3294 + 27 | |
| | 22 | T or C at 3933 | No change L1315 |

[a]S = sporadic mutation; F = familial mutation.
[b]As per Genbank entry U43148.
[c]As per Genbank entry U59464.
[d]As previously reported by Hahn et al., 1996.
[e]Sporadic cases in which parents were analyzed and no mutation was seen.
[f]Complex mechanism involving insertion and deletion.
[g]Polymorphisms in exons 3, 4, and 7 are rare.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated nucleic acid encoding a human nevoid basal cell carcinoma syndrome (NBCCS) (PTC) protein, wherein said protein has a sequence consisting of SEQ. ID. NO:60.

2. The nucleic acid of claim 1, wherein the nucleic acid further comprises a recombinant vector.

3. An isolated nucleic acid wherein said nucleic acid has one missense, nonsense, or frameshift mutation compared to SEQ ID NO:1.

4. The nucleic acid of claim 3, wherein the mutation or mutations is selected from the group consisting of Exon 5 693 insC, Exon 17 2988 del8bp, Exon 17 3014 insA, Exon 21 3538 delG, Exon 22 G4302T, Exon 12 1711insC, Exon 12 1639insA, Exon 16 2707delC, and Intron 17 3157-2A→G.

5. The nucleic acid of claim 3, wherein the mutation is a nonsense mutation.

6. The nucleic acid of claim 3, wherein the mutation is a frameshift mutation.

7. The nucleic acid of claim 6, wherein the mutation is selected from the group consisting of 244delCT, 271insA, 464insAC, 693insC, 804del37, 877delG, 929delC, 1370del76, 1393insTGCC, 1639insA, 1711insC, 2000insC, 2047insCT, 2183delTC, 2320insA, 2392delA, 2583delC, del 2704–2717, 2707delC, 2748insC, 2988del8bp, 3014insA, 3352delAT, and 3538delG.

8. The nucleic acid of claim 3, wherein the mutation is a missense mutation.

9. The nucleic acid of claim 8, wherein the mutation is selected from the group consisting of G1148A, G1368A, G1525T, C2068T, C3015A, G3193C, and G4302T.

10. The nucleic acid of claim 6, wherein the mutation alters mRNA splicing of an exon selected from the group consisting of 1, 1a, and 2a.

11. The nucleic acid of claim 3, wherein the mutation is selected from the group consisting of A1055-2C, and 3157-2A→G.

12. The nucleic acid of claim 3, wherein the mutation is selected from C391T, C1081T, G1148A, CC1081TT, 1444del6, and C2050T.

13. An isolated nucleic acid encoding at least 10 contiguous amino acid residues of a portion of a human nevoid basal cell carcinoma syndrome (NBCCS)(PTC) protein, which nucleic acid encoding said portion of said protein is selected from the group consisting of
   (a) a portion of SEQ ID NO:1 amplified from a human genomic library by primers SEQ ID NO:10 and 11,
   (b) a portion of SEQ ID NO:1 amplified from a human genomic library by primers SEQ ID NO:12 and 13, and
   (c) the sequence GGAGGACGAGGAAAGGGGGGCCAGGGAAAAAAATTGATGTGAAATCCAAGCCCGCGCTCCGAGCAGGGGTTGACGGCCGGCTATG (exon 2a, SEQ ID NO: 84), and
   (d) a nucleic acid that differs from a portion of SEQ ID NO: 1 amplified by the primers of (a) or (b) or encoded by the sequence of (c) by encoding a protein with a conservative substitution of an amino acid relative to the sequence encoded by SEQ ID NO: 1.

14. The nucleic acid of claim 13, wherein said portion of said protein is encoded by a nucleic acid selected from the group consisting of a nucleic acid sequence amplified by primers SEQ ID NO:10 and 11, a nucleic acid sequence amplified by primers SEQ ID NO:12 and 13, and a nucleic acid sequence GGAGGACGAGGAAAGGGGGGCCAGGGAAAAAAATTGATGTGAAATCCAAGCCCGCGCTCCGAGCAGGGGTTGACGGCCGGCTATG (exon 2a, SEQ ID NO: 84).

15. A recombinant vector comprising a nucleic acid of claim 13.

16. An isolated nucleic acid encoding a human nevoid basal cell carcinoma (NBCCS) (PTC) polypeptide comprising at least 10 contiguous amino acids from a polypeptide sequence encoded by a nucleic acid selected from the group consisting of
   (a) a nucleic acid sequence amplified from a human genomic library by primers SEQ ID NO:10 and 11,
   (b) a nucleic acid sequence amplified from a human genomic library by primers SEQ ID NO:12 and 13, and
   (c) a nucleic acid sequence GGAGGACGAGGAAAGGGGGGCCAGGGAAAAAAATTGATGTGAAATCCAAGCCCGCGCTCCGAGCACGGGTTGACGGCCGGCTATG (exon 2a, SEQ ID NO: 84), wherein:
      said polypeptide, when presented as an antigen, elicits the production of an antibody which specifically binds to a human nevoid basal cell carcinoma (NBCCS) (PTC) polypeptide encoded by SEQ ID NO:1.

17. A recombinant vector comprising a nucleic acid of claim 16.

18. An isolated nucleic acid, which nucleic acid encodes a human nevoid basal cell carcinoma (NBCCS) (PTC) polypeptide comprising at least 10 contiguous amino acids from a polypeptide sequence encoded by a nucleic acid selected from the group consisting of
   (a) a nucleic acid sequence amplified from a human genomic library by primers SEQ ID NO:10 and 11,
   (b) a nucleic acid sequence amplified from a human genomic library by primers SEQ ID NO:12 and 13, and
   (c) a nucleic acid sequence GGAGGACGAGGAAAGGGGGGCCAGGGAAAAAAATTGATGTGAAATCCAAGCCCGCGCTCCGAGCAGGGGTTGACGGCCGGCTATG (exon 2a, SEQ ID NO: 84).

19. An isolated nucleic acid encoding a human nevoid basal cell carcinoma syndrome (NBCCS) (PTC) protein, wherein said nucleic acid has the sequence of SEQ ID NO:1.

20. An isolated nucleic acid having a coding region encoding a polypeptide, which coding region has at least 98% sequence identity to a nucleic acid sequence of nucleotides 442 to 4329 of SEQ ID NO:1.

21. A recombinant vector comprising the nucleic acid of claim 20.

* * * * *

SEQUENCE LISTING (1) GENERAL INFORMATION:

(iii) NUMBER OF SEQUENCES: 84

(2) INFORMATION FOR SEQ ID NO:1:

(i) SEQUENCE CHARACTERISTICS:
       (A) LENGTH: 6568 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: -
       (B) LOCATION: 1..6568
       (D) OTHER INFORMATION: /note= "human nevoid basal cell
           carcinoma syndrome (NBCCS)
           (PATCHED (PTC)) cDNA"

(ix) FEATURE:
       (A) NAME/KEY: CDS
       (B) LOCATION: 442..4332

(xi) SEQUENCE DESCRIPTION: SEQ ID NO:1:

GAAGGCGAGC ACCCAGACGG GGGCCCGCCG GGGTCGCGGC CAGCGCCGGG GAAATGCCGC      60

GCCGGGGAGC AGCATGCGCC GGCCTGAGCC CTTCCCTTTG CACTCGGCTG TTTTTTACGT     120

TTAACCAGAA AGGAAGGGAG AGGAGGGAAA GATCCATGTG GCTGCCCTCT TCCGATCACA     180

AATATTGTCG GGAAGGCTAC TGGCCGGAAA GCGCCGCTGT GGCTGAGAGC GAAGTTTCAG     240

-continued

```
AGACTCTTAT TTAAACTGGG TTGTTACATT CAAAAAAACT GCGGCAAGTT CTTGGTTGTG    300
GGCCTCCTCA TATTTGGGGC CTTCGCGGTG GGATTAAAAG CAGCGAACCT CGAGACCAAC    360
GTGGAGGAGC TGTGGGTGGA AGTTGGAGGA CGAGTAAGTC GTGAATTAAA TTATACTCGC    420
CAGAAGATTG GAGAAGAGGC TATGTTTAAT CCTCAACTCA TGATACAGAC CCCTAAAGAA    480
GAAGGTGCTA ATGTCCTGAC CACAGAAGCG CTCCTACAAC ACCTGGACTC GGCACTCCAG    540
GCCAGCCGTG TCCATGTATA CATGTACAAC AGGCAGTGGA AATTGGAACA TTTGTGTTAC    600
AAATCAGGAG AGCTTATCAC AGAAACAGGT TACATGGATC AGATAATAGA ATATCTTTAC    660
CCTTGTTTGA TTATTACACC TTTGGACTGC TTCTGGGAAG GGGCGAAATT ACAGTCTGGG    720
ACAGCATACC TCCTAGGTAA ACCTCCTTTG CGGTGGACAA CTTCGACCC TTTGGAATTC     780
CTGGAAGAGT TAAAGAAAAT AAACTATCAA GTGGACAGCT GGGAGGAAAT GCTGAATAAG    840
GCTGAGGTTG GTCATGGTTA CATGGACCGC CCCTGCCTCA ATCCGGCCGA TCCAGACTGC    900
CCCGCCACAG CCCCCAACAA AAATTCAACC AAACCTCTTG ATATGGCCCT TGTTTTGAAT    960
GGTGGATGTC ATGGCTTATC CAGAAAGTAT ATGCACTGGC AGGAGGAGTT GATTGTGGGT   1020
GGCACAGTCA GAACAGCAC TGGAAAACTC GTCAGCGCCC ATGCCCTGCA GACCATGTTC    1080
CAGTTAATGA CTCCCAAGCA AATGTACGAG CACTTCAAGG GGTACGAGTA TGTCTCACAC   1140
ATCAACTGGA ACGAGGACAA AGCGGCAGCC ATCCTGGAGG CCTGGCAGAG GACATATGTG   1200
GAGGTGGTTC ATCAGAGTGT CGCACAGAAC TCCACTCAAA AGGTGCTTTC CTTCACCACC   1260
ACGACCCTGG ACGACATCCT GAAATCCTTC TCTGACGTCA GTGTCATCCG CGTGGCCAGC   1320
GGCTACTTAC TCATGCTCGC CTATGCCTGT CTAACCATGC TGCGCTGGGA CTGCTCCAAG   1380
TCCCAGGGTG CCGTGGGGCT GGCTGGCGTC CTGCTGGTTG CACTGTCAGT GGCTGCAGGA   1440
CTGGGCCTGT GCTCATTGAT CGGAATTTCC TTTAACGCTG CAACAACTCA GGTTTTGCCA   1500
TTTCTCGCTC TTGGTGTTGG TGTGGATGAT GTTTTCTTC TGGCCCACGC CTTCAGTGAA    1560
ACAGGACAGA ATAAAAGAAT CCCTTTTGAG GACAGGACCG GGGAGTGCCT GAAGCGCACA   1620
GGAGCCAGCG TGGCCCTCAC GTCCATCAGC AATGTCACAG CCTTCTTCAT GGCCGCGTTA   1680
ATCCCAATTC CCGCTCTGCG GGCGTTCTCC CTCCAGGCAG CGGTAGTAGT GGTGTTCAAT   1740
TTTGCCATGG TTCTGCTCAT TTTTCCTGCA ATTCTCAGCA TGGATTTATA TCGACGCGAG   1800
GACAGGAGAC TGGATATTTT CTGCTGTTTT ACAAGCCCCT GCGTCAGCAG AGTGATTCAG   1860
GTTGAACCTC AGGCCTACAC CGACACACAC GACAATACCC GCTACAGCCC CCCACCTCCC   1920
TACAGCAGCC ACAGCTTTGC CCATGAAACG CAGATTACCA TGCAGTCCAC TGTCCAGCTC   1980
CGCACGGAGT ACGACCCCCA CACGCACGTG TACTACACCA CCGCTGAGCC GCGCTCCGAG   2040
ATCTCTGTGC AGCCCGTCAC CGTGACACAG GACACCCTCA GCTGCCAGAG CCCAGAGAGC   2100
ACCAGCTCCA CAAGGGACCT GCTCTCCCAG TTCTCCGACT CCAGCCTCCA CTGCCTCGAG   2160
CCCCCCTGTA CGAAGTGGAC ACTCTCATCT TTTGCTGAGA AGCACTATGC TCCTTTCCTC   2220
TTGAAACCAA AAGCCAAGGT AGTGGTGATC TTCCTTTTTC TGGGCTTGCT GGGGGTCAGC   2280
CTTTATGGCA CCACCCGAGT GAGAGACGGG CTGGACCTTA CGGACATTGT ACCTCGGGAA   2340
ACCAGAGAAT ATGACTTTAT TGCTGCACAA TTCAAATACT TTCTTTCTA CAACATGTAT   2400
ATAGTCACCC AGAAAGCAGA CTACCCGAAT ATCCAGCACT TACTTTACGA CCTACACAGG   2460
AGTTTCAGTA ACGTGAAGTA TGTCATGTTG GAAGAAAACA AACAGCTTCC CAAAATGTGG   2520
CTGCACTACT TCAGAGACTG GCTTCAGGGA CTTCAGGATG CATTTGACAG TGACTGGGAA   2580
```

```
                                    -continued

ACCGGGAAAA TCATGCCAAA CAATTACAAG AATGGATCAG ACGATGGAGT CCTTGCCTAC    2640

AAACTCCTGG TGCAAACCGG CAGCCGCGAT AAGCCCATCG ACATCAGCCA GTTGACTAAA    2700

CAGCGTCTGG TGGATGCAGA TGGCATCATT AATCCCAGCG CTTTCTACAT CTACCTGACG    2760

GCTTGGGTCA GCAACGACCC CGTCGCGTAT GCTGCCTCCC AGGCCAACAT CCGGCCACAC    2820

CGACCAGAAT GGGTCCACGA CAAAGCCGAC TACATGCCTG AAACAAGGCT GAGAATCCCG    2880

GCAGCAGAGC CCATCGAGTA TGCCCAGTTC CCTTTCTACC TCAACGGCTT GCGGGACACC    2940

TCAGACTTTG TGGAGGCAAT TGAAAAAGTA AGGACCATCT GCAGCAACTA TACGAGCCTG    3000

GGGCTGTCCA GTTACCCCAA CGGCTACCCC TTCCTCTTCT GGGAGCAGTA CATCGGCCTC    3060

CGCCACTGGC TGCTGCTGTT CATCAGCGTG GTGTTGGCCT GCACATTCCT CGTGTGCGCT    3120

GTCTTCCTTC TGAACCCCTG GACGGCCGGG ATCATTGTGA TGGTCCTGGC GCTGATGACG    3180

GTCGAGCTGT TCGGCATGAT GGGCCTCATC GGAATCAAGC TCAGTGCCGT GCCCGTGGTC    3240

ATCCTGATCG CTTCTGTTGG CATAGGAGTG GAGTTCACCG TTCACGTTGC TTTGGCCTTT    3300

CTGACGGCCA TCAGCGACAA GAACCGCAGG GCTGTGCTTG CCCTGGAGCA CATGTTTGCA    3360

CCCGTCCTGG ATGGCGCCGT GTCCACTCTG CTGGGAGTGC TGATGCTGGC GGGATCTGAG    3420

TTCGACTTCA TTGTCAGGTA TTTCTTTGCT GTGCTGGCAA TCCTCACCAT CCTCGGCGTT    3480

CTCAATGGGC TGGTTTTGCT TCCCGTGCTT TTGTCTTTCT TTGGACCATA TCCTGAGGTG    3540

TCTCCAGCCA ACGGCTTGAA CCGCCTGCCC ACACCCTCCC CTGAGCCACC CCCCAGCGTG    3600

GTCCGCTTCG CCATGCCGCC CGGCCACACG CACAGCGGGT CTGATTCCTC CGACTCGGAG    3660

TATAGTTCCC AGACGACAGT GTCAGGCCTC AGCGAGGAGC TTCGGCACTA CGAGGCCCAG    3720

CAGGGCGCGG GAGGCCCTGC CCACCAAGTG ATCGTGGAAG CCACAGAAAA CCCCGTCTTC    3780

GCCCACTCCA CTGTGGTCCA TCCCGAATCC AGGCATCACC CACCCTCGAA CCCGAAACAG    3840

CAGCCCCACC TGGACTCAGG GTCCCTGCCT CCCGGACGGC AAGGCCAGCA GCCCCGCAGG    3900

GACCCCCCCA GAAAAGGCTT GTGGCCACCC CTCTACAGAC CGCGCAGAGA CGCTTTTGAA    3960

ATTTCTACTG AAGGGCATTC TGGCCCTAGC AATAGGGCCC GCTGGGGCCC TCGCGGGGCC    4020

CGTTCTCACA ACCCTCGGAA CCCAACGTCC ACTGCCATGG GCAGCTCCGT GCCCGGCTAC    4080

TGCCAGCCCA TCACCACTGT GACGGCTTCT GCCTCCGTGA CTGTCGCCGT GCACCCGCCG    4140

CCTGTCCCTG GGCCTGGGCG GAACCCCCGA GGGGGACTCT GCCCAGGCTA CCCTGAGACT    4200

GACCACGGCC TGTTTGAGGA CCCCCACGTG CCTTTCCACG TCCGGTGTGA GAGGAGGGAT    4260

TCGAAGGTGG AAGTCATTGA GCTGCAGGAC GTGGAATGCG AGGAGAGGCC CCGGGGAAGC    4320

AGCTCCAACT GAGGGTGATT AAAATCTGAA GCAAAGAGGC CAAAGATTGG AAACCCCCCA    4380

CCCCCACCTC TTTCCAGAAC TGCTTGAAGA GAACTGGTTG GAGTTATGGA AAAGATGCCC    4440

TGTGCCAGGA CAGCAGTTCA TTGTTACTGT AACCGATTGT ATTATTTTGT TAAATATTTC    4500

TATAAATATT TAAGAGATGT ACACATGTGT AATATAGGAA GGAAGGATGT AAAGTGGTAT    4560

GATCTGGGCC TTCTCCACTC CTGCCCCAGA GTGTGGAGGC CACAGTGGGG CCTCTCCGTA    4620

TTTGTGCATT GGGCTCCGTG CCACAACCAA GCTTCATTAG TCTTAAATTT CAGCATATGT    4680

TGCTGCTGCT TAAATATTGT ATAATTTACT TGTATAATTC TATGCAAATA TTGCTTATGT    4740

AATAGGATTA TTTTGTAAAG GTTTCTGTTT AAAATATTTT AAATTTGCAT ATCACAACCC    4800

TGTGGTAGTA TGAAATGTTA CTGTTAACTT TCAAACACGC TATGCGTGAT AATTTTTTTG    4860

TTTAATGAGC AGATATGAAG AAAGCACGTT AATCCTGGTG GCTTCTCTAG GTGTCGTTGT    4920

GTGCGGTCCT CTTGTTTGGC TGTGCGTGTG AACACGTGTG TGAGTTCACC ATGTACTGTA    4980
```

```
CTGTGATTTT TTTTTTTGTC TTGTTTTGTT TCTCTACACT GTCTGTAACC TGTAGTAGGC    5040

TCTGACCTAT TCAGGCTGGA AAGCGTCAGG ATATCTTTTC TTCGTGCTGG TGAGGGCTGG    5100

CCCTAAACAT CCACCTAATC CTTTCAAATC AGCCCGGCAA AAGCTAAACT CTCCTCGTGT    5160

CTACGGGCAT CTGTTATGAT CATTGGCTGC CATCCAGGAC CCCAATTTGT GCTTCAGGGG    5220

GATAATCTCC TTCTCTCGGA TCATTGTGAT GGATGCTGGA ACCTCAGGGT ATGGAGCTCA    5280

CATCAGTTCA TCATGGTGGG TGTTAGAGAA TTCGGTGACA TGCCTAGTGC TGAGCCTTGG    5340

CTGGGCCATG AGAGTCTGTA TAATAAAAAA AGCATGCAGC ATGGTGCCCC TCTTTTGACC    5400

AACACACACA AGACCCCTCC CCCAACACCC CCAAATTCAA GAGTGGATGT GGCCCTGTCA    5460

CAGGTAGAAA AACCTATTTA GTTAATTCTT TCTTGGCCCA CAGTCTCCCA GAAATGATGT    5520

TTTGAGTCCC TATAGTTTAA AGTCCCTCTC TTAAATGGAG CAGCTGGTTT GAGGTTTCTA    5580

AATCTGTTTG CATTTTCTTT AAAATTAAGT GGTGAGCATG CATTGTGGTG TAGAGGCAGG    5640

CATTATGTAG GATAAGAGCT CCGGGGGGAT TCTTCATGCA CCAGTGTTTA GGGTACGTGC    5700

TTCCTAAGTA AATCCAAACA TTGTCTCCAT CCTCCCCGTC ATTAGTGCTC TTTCAATGTG    5760

ATGTGGGAAA GCAGGAGGAT GGACACACCC CACTGAAAGA TGTAGGCAGG GGCAGGTCTC    5820

TCAACCAGGC ATATTTTTAA AAGTTGCTTC TGTACTGGTT CTCTTCTTTT GCTCTGAGGT    5880

GTGGGCTCCC TCATCTCGTA ACCAGAGACC AGCACATGTC AGGGAAGCAC CCAGTGTCGG    5940

CTCCCCATCC CAATCCACAC CAGCACCTTG TTACAGACAA GAAGTCAGAG GAAAGGGCGG    6000

GGTCCCTGCA GGGCTGAAGC CTAAGCTACT GTGAGGTGCT CACAAGTGGC AGCTCCTGTA    6060

ATCCCTTTTA AATTACGTGG GAATCTTAAC AGAAAGTAAT GGGCCCCCAG AAATACCCAC    6120

AGCATAGGAC NTCAGACCCT GAACTCACCA CAAAATTTTA AGATGCTGAT TGGGAGCCGC    6180

TTGTGGCTGC TGGATGNGTG TGTGTGTGTG TGTGTGTGCG TGCGTGCGTG TGTGTGTGTG    6240

TCTGNTGGGG ACCCTGGCCA CCCCCCTGCT GCTGTCTTGG TGCCTGTCAC CCACATGGTC    6300

TGCCATCCTA ACACCCAGCT CTGCTCAGAA AACGTCCTGC GTGGAGGAGG GATGATGCAG    6360

AATTCTGAAG TCGACTTCCC TCTGGCTCCT GGCGTGCCCT CGCTCCCTTC CTGAGCCCAG    6420

CTCGTGTTGC GCCGGAGGCT GCGCGGCCCC TGATTTCTGC ATGGTGTAGA ACTTTCTCCA    6480

ATAGTCACAT TGGCAAAGGG AGAACTGGGG TGGGCGGGGG GTGGGCTGG CAGGGAATTA    6540

GCATTTCTCT CTCTCTTTTA ATAGTTAA                                      6568

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "PTC1 primer"

(xi) SEQUENCE DESCRIPTION: SEQ ID NO:2:

TTGCATAACC AGCGAGTCT                                                   19

(2) INFORMATION FOR SEQ ID NO:3:

(i) SEQUENCE CHARACTERISTICS:
```

(A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..22
            (D) OTHER INFORMATION: /note= "PTC2 primer"

(xi) SEQUENCE DESCRIPTION: SEQ ID NO:3:

CAAATGTACG AGCACTTCAA GG                                              22

(2) INFORMATION FOR SEQ ID NO:4:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..18
            (D) OTHER INFORMATION: /note= "W18F3 primer"

(xi) SEQUENCE DESCRIPTION: SEQ ID NO:4:

CTGTCAAGGT GAATGGAC                                                   18

(2) INFORMATION FOR SEQ ID NO:5:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..19
            (D) OTHER INFORMATION: /note= "W18R3 primer"

(xi) SEQUENCE DESCRIPTION: SEQ ID NO:5:

GGGGTTATTC TGTAAAAGG                                                  19

(2) INFORMATION FOR SEQ ID NO:6:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:6:

GAGGCTATGT                                                            10

(2) INFORMATION FOR SEQ ID NO:7:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

GCCGCCATGG                                                                          10

(2) INFORMATION FOR SEQ ID NO:8:

(i) SEQUENCE CHARACTERISTICS:
             (A) LENGTH: 6 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:8:

AATAAA                                                                              6

(2) INFORMATION FOR SEQ ID NO:9:

(i) SEQUENCE CHARACTERISTICS:
             (A) LENGTH: 5 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:9:

ATTTA                                                                               5

(2) INFORMATION FOR SEQ ID NO:10:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: -
             (B) LOCATION: 1..18
             (D) OTHER INFORMATION: /note= "PTCF18 primer"

(xi) SEQUENCE DESCRIPTION: SEQ ID NO:10:

GAAGGCGAGC ACCCAGAC                                                                 18

(2) INFORMATION FOR SEQ ID NO:11:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: -
             (B) LOCATION: 1..20
             (D) OTHER INFORMATION: /note= "PTCR18 primer"

(xi) SEQUENCE DESCRIPTION: SEQ ID NO:11:

TCTTTCCCTC CTCTCCCTTC                                                               20

(2) INFORMATION FOR SEQ ID NO:12:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "PTCF22 primer"

(xi) SEQUENCE DESCRIPTION: SEQ ID NO:12:

GCTATGGAAA TGCGTCGG                                                   18

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCR22 primer"

(xi) SEQUENCE DESCRIPTION: SEQ ID NO:13:

CAGTCCTGCT CTGTCCATCA                                                 20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCF19 primer"

(xi) SEQUENCE DESCRIPTION: SEQ ID NO:14:

GTGGCTGAGA GCGAAGTTTC                                                 20

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "PTCR19 primer"

(xi) SEQUENCE DESCRIPTION: SEQ ID NO:15:

TTCCACCCAC AGCTCCTC                                                   18
```

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "PTCF27 primer"

(xi) SEQUENCE DESCRIPTION: SEQ ID NO:16:

CTATTGTGTA TCCAATGGCA GG                                                22

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "PTCR27 primer"

(xi) SEQUENCE DESCRIPTION: SEQ ID NO:17:

ATTAGTAGGT GGACGCGGC                                                     19

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..26
        (D) OTHER INFORMATION: /note= "PTCF20 primer"

(xi) SEQUENCE DESCRIPTION: SEQ ID NO:18:

AGAGAAATTT TTGTCTCTGC TTTTCA                                      26

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "PTCR20 primer"

(xi) SEQUENCE DESCRIPTION: SEQ ID NO:19:

CCTGATCCAT GTAACCTGTT TC                                                22

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "PTCF21 primer"

(xi) SEQUENCE DESCRIPTION: SEQ ID NO:20:

GCAAAAATTT CTCAGGAACA CC                                              22

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "PTCR21 primer"

(xi) SEQUENCE DESCRIPTION: SEQ ID NO:21:

TGGAACAAAC AATGATAAGC AA                                              22

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCF15 primer"

(xi) SEQUENCE DESCRIPTION: SEQ ID NO:22:

CCTACAAGGT GGATGCAGTG                                                 20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "18R2 primer"

(xi) SEQUENCE DESCRIPTION: SEQ ID NO:23:

TTTGCTCTCC ACCCTTCTGA                                                 20

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "11e18F primer"

(xi) SEQUENCE DESCRIPTION: SEQ ID NO:24:

GTGACCTGCC TACTAATTCC C                      21

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "18R3 primer"

(xi) SEQUENCE DESCRIPTION: SEQ ID NO:25:

GGCTAGCGAG GATAACGGTT TA                     22

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCF2 primer"

(xi) SEQUENCE DESCRIPTION: SEQ ID NO:26:

GAGGCAGTGG AAACTGCTTC                       20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCR2 primer"

(xi) SEQUENCE DESCRIPTION: SEQ ID NO:27:

```
TTGCATAACC AGCGAGTCTG                                                      20
```

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "PTCF23 primer"

(xi) SEQUENCE DESCRIPTION: SEQ ID NO:28:

```
GTGCTGTCGA GGCTTGTG                                                        18
```

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCR23 primer"

(xi) SEQUENCE DESCRIPTION: SEQ ID NO:29:

```
ACGGACAGCA GATAAATGGC                                                      20
```

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "PTCF5 primer"

(xi) SEQUENCE DESCRIPTION: SEQ ID NO:30:

```
GTGTTAGGTG CTGGTGGCA                                                       19
```

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..20
        (D) OTHER INFORMATION: /note= "PTCR5 primer"

(xi) SEQUENCE DESCRIPTION: SEQ ID NO:31:

```
CTTAGGAACA GAGGAAGCTG                                                    20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCF24PT primer"

(xi) SEQUENCE DESCRIPTION: SEQ ID NO:32:

TCTGCCACGT ATCTGCTCAC                                                    20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "CR24 primer"

(xi) SEQUENCE DESCRIPTION: SEQ ID NO:33:

CATGCTGAGA ATTGCAGGAA                                                    20

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "PTCF16 primer"

(xi) SEQUENCE DESCRIPTION: SEQ ID NO:34:

GGCCTACACC GACACACAC                                                     19

(2) INFORMATION FOR SEQ ID NO:35:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..23
        (D) OTHER INFORMATION: /note= "PTCR16 primer"
```

(xi) SEQUENCE DESCRIPTION: SEQ ID NO:35:

TTTTTTTGAA GACAGGAAGA GCC                                                    23

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTC13R primer"

(xi) SEQUENCE DESCRIPTION: SEQ ID NO:36:

GTCAGCAGAC TGATTCAGGT                                                        20

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "PTC37R primer"

(xi) SEQUENCE DESCRIPTION: SEQ ID NO:37:

AAGATGAGAG TGTCCACTTC G                                                      21

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCF14 primer"

(xi) SEQUENCE DESCRIPTION: SEQ ID NO:38:

GACAGCTTCT CTTTGTCCAG                                                        20

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "PCTR14 primer"

(xi) SEQUENCE DESCRIPTION: SEQ ID NO:39:

ACGCAAAAGA CCGAAAGGAC GA                                                22

(2) INFORMATION FOR SEQ ID NO:40:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note= "PCTF13 primer"

(xi) SEQUENCE DESCRIPTION: SEQ ID NO:40:

AGGGTCCTTC TGGCTGCGAG                                                   20

(2) INFORMATION FOR SEQ ID NO:41:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..22
            (D) OTHER INFORMATION: /note= "PTCR13 primer"

(xi) SEQUENCE DESCRIPTION: SEQ ID NO:41:

TCAGTGCCCA GCAGCTGGAG TA                                                22

(2) INFORMATION FOR SEQ ID NO:42:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..26
            (D) OTHER INFORMATION: /note= "PTCF7 primer"

(xi) SEQUENCE DESCRIPTION: SEQ ID NO:42:

AACCCCATTC TCAAAGGCCT CTGTTC                                            26

(2) INFORMATION FOR SEQ ID NO:43:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..23

(D) OTHER INFORMATION: /note= "PTCR7 primer"

(xi) SEQUENCE DESCRIPTION: SEQ ID NO:43:

CACCTCTGTA AGTTCCCAGA CCT                                    23

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "PTCF12 primer"

(xi) SEQUENCE DESCRIPTION: SEQ ID NO:44:

AACTGTGATG CTCTTCTACC CTGG                                   24

(2) INFORMATION FOR SEQ ID NO:45:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "PTCR12 primer"

(xi) SEQUENCE DESCRIPTION: SEQ ID NO:45:

AAACTTCCCG GCTGCAGAAA GA                                     22

(2) INFORMATION FOR SEQ ID NO:46:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /note= "PTCF8 primer"

(xi) SEQUENCE DESCRIPTION: SEQ ID NO:46:

TTTGATCTGA ACCGAGGACA CC                                     22

(2) INFORMATION FOR SEQ ID NO:47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -

(B) LOCATION: 1..22
            (D) OTHER INFORMATION: /note= "PTCR8 primer"

(xi) SEQUENCE DESCRIPTION: SEQ ID NO:47:

CAAACAGAGC CAGAGGAAAT GG                                              22

(2) INFORMATION FOR SEQ ID NO:48:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..23
        (D) OTHER INFORMATION: /note= "PTCF11 primer"

(xi) SEQUENCE DESCRIPTION: SEQ ID NO:48:

TAGGACAGAG CTGAGCATTT ACC                                             23

(2) INFORMATION FOR SEQ ID NO:49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "PTC21R primer"

(xi) SEQUENCE DESCRIPTION: SEQ ID NO:49:

TACCTGACAA TGAAGTCG                                                   18

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCF25 primer"

(xi) SEQUENCE DESCRIPTION: SEQ ID NO:50:

AACAGAGGCC CCTGAAAAAT                                                 20

(2) INFORMATION FOR SEQ ID NO:51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:

```
        (A) NAME/KEY: -
        (B) LOCATION: 1..18
        (D) OTHER INFORMATION: /note= "PTCR25 primer"

(xi) SEQUENCE DESCRIPTION: SEQ ID NO:51:

GATCACTTGG TGGGCAGG                                              18

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTCF10 primer"

(xi) SEQUENCE DESCRIPTION: SEQ ID NO:52:

TCTAACCCAC CCTCACCCTT                                            20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "PTC31R primer"

(xi) SEQUENCE DESCRIPTION: SEQ ID NO:53:

ATTGTTAGGG CCAGAATGCC                                            20

(2) INFORMATION FOR SEQ ID NO:54:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "PTCF26 primer"

(xi) SEQUENCE DESCRIPTION: SEQ ID NO:54:

AGAAAAGGCT TGTGGCCAC                                             19

(2) INFORMATION FOR SEQ ID NO:55:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA
```

```
    (ix) FEATURE:
         (A) NAME/KEY: -
         (B) LOCATION: 1..19
         (D) OTHER INFORMATION: /note= "PTCR26 primer"

(xi) SEQUENCE DESCRIPTION: SEQ ID NO:55:

TCACCCTCAG TTGGAGCTG                                                    19

(2) INFORMATION FOR SEQ ID NO:56:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:56:

GAGTACGACC CCCACACG                                                     18

(2) INFORMATION FOR SEQ ID NO:57:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:57:

GAGTACGACC CCCCACACG                                                    19

(2) INFORMATION FOR SEQ ID NO:58:

(i) SEQUENCE CHARACTERISTICS:
         (A) LENGTH: 1734 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 310..327
         (D) OTHER INFORMATION: /note= "MuPTC1 primer sequence"

(ix) FEATURE:
         (A) NAME/KEY: misc_feature
         (B) LOCATION: complement (486..505)
         (D) OTHER INFORMATION: /note= "MuPTCR1 primer sequence"

(ix) FEATURE:
         (A) NAME/KEY: exon
         (B) LOCATION: 310..510
         (D) OTHER INFORMATION: /note= "exon 1b"

(ix) FEATURE:
         (A) NAME/KEY: misc_feature
         (B) LOCATION: 1252..1269
         (D) OTHER INFORMATION: /note= "PTCF18 primer sequence"

(ix) FEATURE:
         (A) NAME/KEY: misc_feature
         (B) LOCATION: complement (1384..1403)
         (D) OTHER INFORMATION: /note= "PTCR18 primer sequence"

(ix) FEATURE:
         (A) NAME/KEY: exon
         (B) LOCATION: 1252..1440
         (D) OTHER INFORMATION: /note= "exon 1"
```

(ix) FEATURE:
    (A) NAME/KEY: misc_feature
    (B) LOCATION: 1497..1514
    (D) OTHER INFORMATION: /note= "PTCF22 primer sequence"

(ix) FEATURE:
    (A) NAME/KEY: misc_feature
    (B) LOCATION: complement (1645..1664)
    (D) OTHER INFORMATION: /note= "PTCR22 primer sequence"

(ix) FEATURE:
    (A) NAME/KEY: misc_feature
    (B) LOCATION: 1732
    (D) OTHER INFORMATION: /note= "end of exon 1a"

(xi) SEQUENCE DESCRIPTION: SEQ ID NO:58:

```
ATCTTCCGCG AACTGGATGT GGGCAGCGGC GGCCAGCAGA GACCTCGGGA CCCCGCGCAA        60
TGTGGCAATG GAAGGCGCAG GGTCTGACTC CCCGGCAGCG GCCGCGGCCG CAGCGGCAGC       120
AGCGCCCGCC GTGTGAGCAG CAGCAGCGGC TGGTCTGTCA ACCGGAGCCC GAGCCCGAGC       180
AGCGAGCGGC CAGCAGCGTC CTCGCAAGCC GAGCGCCCAG GCGCGCCAGG AGCCCGCAGC       240
AGCGGCAGCA GCGCGCCGGG CCGCCCGGGA AGCCTCCGTC CCCGCGGCGG CGGCGGCGGC       300
GGCGGCAACA TGGCCTCGGC TGGTAACGCC GCCGAGCCCC AGGACCGCGG CGGCGGCGGC       360
AGCGGCTGTA TCGGTGCCCC GGGACGGCCG GCTGGAGGCG GGAGGCGCAC ACGGACGGGG       420
GGGCTGCGCC GTGCTGCCGC GCCGGACCGG GACTATCTGC ACCGGCCCAG CTACTGCGAC       480
GCCGCCTTCG CTCTGGAGCA GATTTCCAAG GTGCATTTCA GACTCTCTCC TCCCACTTTC       540
TCTTCCCTCC TCTAACTCTT TGGGATCGCC CCCGCCACAC ACAAACACAC ACACTCTCTT       600
CCTCTCTCTC TCACACACAC ACACACATGC TCACGCTGCT GCCTCCACGA AAAGCAGCAG       660
AGACAAATGG GGATTGAAAA ATTCAAACCC TCCCTCTGGT CCTGGGAGGA AAGGGCTGTC       720
TGAGGTCCGA AGGGGGTGGA GGTGTGTGTG TGTGCGTGTG TGTGTGTGTA TACACACGCC       780
CTCCCTGGTG TGCCTTTTCC GGAGCACTGG AAAGCCGTCC ACGGCGGACC ACCTCAAGGG       840
CGGCCGCGGC ACTGTCCTGC CCCGTGCCCC CTGCCCTGAA CTTCTTCCTC CTGCGCCCCT       900
GCCCCTATTT GCAGCCTAAA CTCCTGTACG GCTGCCACAT TTCTTAACAT CTTGGAAGGG       960
GAGCGGAGTG GAGAGAGAGC GGAGAGAGGA AGGGGGGAGG GGAGCCGAAA TAAAGGTGGT      1020
TTCCTTTTTT GCAGCCAGTT TTGTTGAGCA TGAAATCTCT GCTCCATTAA AAAATTATTN      1080
TCGGAAAAAG ATATCCCCCC AGTTTTCCAG GTTTTGAGCC GCCTCTCCTT AGGGCCTGGT      1140
CGGGGGAGGA AAAGTTGTAA ACAAATTGCC ACATTAAATT CGCGGTGCGA GTCTGCGGAG      1200
CTGCCGGGTT CATTGTGTNT ACGAGGCTCG CTGAAATGTG TGGAATCCAG GGAAGGCGAG      1260
CACCCAGACG GGGGCCCGCC GGGGTCGCGG CCAGCGCCGG GGAAATGCCG CGCCGGGGAG      1320
CAGCATGCGC CGGCCTGAGC CCTTCCCTTT GCACTCGGCT GTTTTTTACG TTTAACCAGA      1380
AAGGAAGGGA GAGGAGGGAA AGATCCATGT GGCTGCCCTC TTCCGATCAC AAATATTGTC      1440
GTAAGTTGCA GCTGGCTGCC CCACTTCCTA ATTCAGCTCA CACAGCCTCT CCCCACGCTA      1500
TGGAAATGCG TCGGGAGTGA ACTCCGGCGG CCGCGCTCAC CACGTGGATC CCCACTTACT      1560
ACCATTCTCG GCGGGGTCC AGTTGGGGGA ACCCGCAATA TGTTGTTCCA AAGAGCGCTC      1620
GCCCCTAGCG CCCGTCCCCG AGGGTGATGG ACAGAGCAGG ACTGGTTTGC TGGCTCCTGA      1680
ACCTTGGGCT CCATCGCTGG GATTACGCAG CCCCTCCCTT CTCAGCTCTG GGT            1734
```

(2) INFORMATION FOR SEQ ID NO:59:

(i) SEQUENCE CHARACTERISTICS:
    (A) LENGTH: 659 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: exon
    (B) LOCATION: 305..390
    (D) OTHER INFORMATION: /note= "exon 2a"

(ix) FEATURE:
    (A) NAME/KEY: misc_feature
    (B) LOCATION: 336..357
    (D) OTHER INFORMATION: /note= "PTCXF1 primer sequence"

(ix) FEATURE:
    (A) NAME/KEY: misc_feature
    (B) LOCATION: complement (365..379)
    (D) OTHER INFORMATION: /note= "PTCXR1 primer sequence"

(xi) SEQUENCE DESCRIPTION: SEQ ID NO:59:

```
GGATCCGTCA CGTGACCCTG ACAGTTCCTG CTTATGGCGC GGCAGACCAC CCACGCCGAG    60

GGCCATGGAA CTGCTTAATA GAAACAGGCT TGTAATTGTG AGTCCGCGCT GCACTCCGCC   120

GAAAGCTTCC GGCGGCCCAG CGCGCCGGGG TTTTTACACT TTCCGTTCCT TTTGTAAAGA   180

CGGAGGAGGA GGAGAAGAAG AAGAAGAAAA CGGAGGAGAA GAAAAAGACG ACAGGGGAGA   240

CAAAGAGACC CGCAGCGACA AGGCAAGGGG GAGACGAGGG AAGACTGGGA GAAGACGGAG   300

GAGCGGAGGA CGAGGAAAGG GGGGCCAGGG AAAAAAAATT GATGTGAAAT CCAAGCCCGC   360

GCTCCGAGCA GGGGTTGACG GCCGGCTATG GTNAGTGCAG CCAGCGCGGC NGCCGCCGAC   420

GCCACCTCGC CTCTCGCGCC NTGCTCCTCG GGCGGCGCGG GGACNCTGGG ACNCGGGACG   480

CCCCNCNCGG CGGACGGANG AGCNAGCCCC GATCGCCGGG CNGGAGGGGC GGGCCNCGCG   540

CCNGGGCCGT GGATCCGGGT GGGCTGCGCC GCCTGGGCTC NGGANCNCTG GTCNCGCTCC   600

TCCNCTCTCN CTCGCACNCC CGGGCCCCCG CCCCCNATGC NATCCCCTCT TGGCNGGGA    659
```

(2) INFORMATION FOR SEQ ID NO:60:

(i) SEQUENCE CHARACTERISTICS:
        (A) LENGTH: 1296 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..1296
        (D) OTHER INFORMATION: /note= "amino acids encoded by human
            nevoid basal cell carcinoma syndrome
            (NBCCS) (PATCHED (PTC)) cDNA"

(xi) SEQUENCE DESCRIPTION: SEQ ID NO:60:

```
Met Phe Asn Pro Gln Leu Met Ile Gln Thr Pro Lys Glu Glu Gly Ala
 1               5                  10                  15

Asn Val Leu Thr Thr Glu Ala Leu Leu Gln His Leu Asp Ser Ala Leu
            20                  25                  30

Gln Ala Ser Arg Val His Val Tyr Met Tyr Asn Arg Gln Trp Lys Leu
        35                  40                  45

Glu His Leu Cys Tyr Lys Ser Gly Glu Leu Ile Thr Glu Thr Gly Tyr
    50                  55                  60
```

```
-continued

Met Asp Gln Ile Ile Glu Tyr Leu Tyr Pro Cys Leu Ile Ile Thr Pro
 65                  70                  75                  80

Leu Asp Cys Phe Trp Glu Gly Ala Lys Leu Gln Ser Gly Thr Ala Tyr
                 85                  90                  95

Leu Leu Gly Lys Pro Pro Leu Arg Trp Thr Asn Phe Asp Pro Leu Glu
                100                 105                 110

Phe Leu Glu Glu Leu Lys Lys Ile Asn Tyr Gln Val Asp Ser Trp Glu
            115                 120                 125

Glu Met Leu Asn Lys Ala Glu Val Gly His Gly Tyr Met Asp Arg Pro
        130                 135                 140

Cys Leu Asn Pro Ala Asp Pro Asp Cys Pro Ala Thr Ala Pro Asn Lys
145                 150                 155                 160

Asn Ser Thr Lys Pro Leu Asp Met Ala Leu Val Leu Asn Gly Gly Cys
                165                 170                 175

His Gly Leu Ser Arg Lys Tyr Met His Trp Gln Glu Glu Leu Ile Val
            180                 185                 190

Gly Gly Thr Val Lys Asn Ser Thr Gly Lys Leu Val Ser Ala His Ala
        195                 200                 205

Leu Gln Thr Met Phe Gln Leu Met Thr Pro Lys Gln Met Tyr Glu His
    210                 215                 220

Phe Lys Gly Tyr Glu Tyr Val Ser His Ile Asn Trp Asn Glu Asp Lys
225                 230                 235                 240

Ala Ala Ala Ile Leu Glu Ala Trp Gln Arg Thr Tyr Val Glu Val Val
                245                 250                 255

His Gln Ser Val Ala Gln Asn Ser Thr Gln Lys Val Leu Ser Phe Thr
            260                 265                 270

Thr Thr Thr Leu Asp Asp Ile Leu Lys Ser Phe Ser Asp Val Ser Val
        275                 280                 285

Ile Arg Val Ala Ser Gly Tyr Leu Leu Met Leu Ala Tyr Ala Cys Leu
    290                 295                 300

Thr Met Leu Arg Trp Asp Cys Ser Lys Ser Gln Gly Ala Val Gly Leu
305                 310                 315                 320

Ala Gly Val Leu Leu Val Ala Leu Ser Val Ala Ala Gly Leu Gly Leu
                325                 330                 335

Cys Ser Leu Ile Gly Ile Ser Phe Asn Ala Ala Thr Thr Gln Val Leu
            340                 345                 350

Pro Phe Leu Ala Leu Gly Val Gly Val Asp Asp Val Phe Leu Leu Ala
        355                 360                 365

His Ala Phe Ser Glu Thr Gly Gln Asn Lys Arg Ile Pro Phe Glu Asp
    370                 375                 380

Arg Thr Gly Glu Cys Leu Lys Arg Thr Gly Ala Ser Val Ala Leu Thr
385                 390                 395                 400

Ser Ile Ser Asn Val Thr Ala Phe Phe Met Ala Ala Leu Ile Pro Ile
                405                 410                 415

Pro Ala Leu Arg Ala Phe Ser Leu Gln Ala Ala Val Val Val Val Phe
            420                 425                 430

Asn Phe Ala Met Val Leu Leu Ile Phe Pro Ala Ile Leu Ser Met Asp
        435                 440                 445

Leu Tyr Arg Arg Glu Asp Arg Arg Leu Asp Ile Phe Cys Cys Phe Thr
    450                 455                 460

Ser Pro Cys Val Ser Arg Val Ile Gln Val Glu Pro Gln Ala Tyr Thr
465                 470                 475                 480

Asp Thr His Asp Asn Thr Arg Tyr Ser Pro Pro Pro Tyr Ser Ser
```

-continued

```
                485                 490                 495
His Ser Phe Ala His Glu Thr Gln Ile Thr Met Gln Ser Thr Val Gln
                500                 505                 510

Leu Arg Thr Glu Tyr Asp Pro His Thr His Val Tyr Tyr Thr Thr Ala
            515                 520                 525

Glu Pro Arg Ser Glu Ile Ser Val Gln Pro Val Thr Val Thr Gln Asp
        530                 535                 540

Thr Leu Ser Cys Gln Ser Pro Glu Ser Thr Ser Ser Thr Arg Asp Leu
545                 550                 555                 560

Leu Ser Gln Phe Ser Asp Ser Ser Leu His Cys Leu Glu Pro Pro Cys
                565                 570                 575

Thr Lys Trp Thr Leu Ser Ser Phe Ala Glu Lys His Tyr Ala Pro Phe
                580                 585                 590

Leu Leu Lys Pro Lys Ala Lys Val Val Ile Phe Leu Phe Leu Gly
                595                 600                 605

Leu Leu Gly Val Ser Leu Tyr Gly Thr Thr Arg Val Arg Asp Gly Leu
            610                 615                 620

Asp Leu Thr Asp Ile Val Pro Arg Glu Thr Arg Glu Tyr Asp Phe Ile
625                 630                 635                 640

Ala Ala Gln Phe Lys Tyr Phe Ser Phe Tyr Asn Met Tyr Ile Val Thr
                645                 650                 655

Gln Lys Ala Asp Tyr Pro Asn Ile Gln His Leu Leu Tyr Asp Leu His
                660                 665                 670

Arg Ser Phe Ser Asn Val Lys Tyr Val Met Leu Glu Glu Asn Lys Gln
            675                 680                 685

Leu Pro Lys Met Trp Leu His Tyr Phe Arg Asp Trp Leu Gln Gly Leu
        690                 695                 700

Gln Asp Ala Phe Asp Ser Asp Trp Glu Thr Gly Lys Ile Met Pro Asn
705                 710                 715                 720

Asn Tyr Lys Asn Gly Ser Asp Asp Gly Val Leu Ala Tyr Lys Leu Leu
                725                 730                 735

Val Gln Thr Gly Ser Arg Asp Lys Pro Ile Asp Ile Ser Gln Leu Thr
            740                 745                 750

Lys Gln Arg Leu Val Asp Ala Asp Gly Ile Ile Asn Pro Ser Ala Phe
        755                 760                 765

Tyr Ile Tyr Leu Thr Ala Trp Val Ser Asn Asp Pro Val Ala Tyr Ala
770                 775                 780

Ala Ser Gln Ala Asn Ile Arg Pro His Arg Pro Glu Trp Val His Asp
785             790                 795                 800

Lys Ala Asp Tyr Met Pro Glu Thr Arg Leu Arg Ile Pro Ala Ala Glu
                805                 810                 815

Pro Ile Glu Tyr Ala Gln Phe Pro Phe Tyr Leu Asn Gly Leu Arg Asp
            820                 825                 830

Thr Ser Asp Phe Val Glu Ala Ile Glu Lys Val Arg Thr Ile Cys Ser
        835                 840                 845

Asn Tyr Thr Ser Leu Gly Leu Ser Ser Tyr Pro Asn Gly Tyr Pro Phe
        850                 855                 860

Leu Phe Trp Glu Gln Tyr Ile Gly Leu Arg His Trp Leu Leu Leu Phe
865                 870                 875                 880

Ile Ser Val Val Leu Ala Cys Thr Phe Leu Val Cys Ala Val Phe Leu
                885                 890                 895

Leu Asn Pro Trp Thr Ala Gly Ile Ile Val Met Val Leu Ala Leu Met
            900                 905                 910
```

```
Thr Val Glu Leu Phe Gly Met Met Gly Leu Ile Gly Ile Lys Leu Ser
            915                 920                 925
Ala Val Pro Val Val Ile Leu Ile Ala Ser Val Gly Ile Gly Val Glu
            930                 935                 940
Phe Thr Val His Val Ala Leu Ala Phe Leu Thr Ala Ile Ser Asp Lys
945                 950                 955                 960
Asn Arg Arg Ala Val Leu Ala Leu Glu His Met Phe Ala Pro Val Leu
            965                 970                 975
Asp Gly Ala Val Ser Thr Leu Leu Gly Val Leu Met Leu Ala Gly Ser
            980                 985                 990
Glu Phe Asp Phe Ile Val Arg Tyr Phe Phe Ala Val Leu Ala Ile Leu
            995                 1000                1005
Thr Ile Leu Gly Val Leu Asn Gly Leu Val Leu Leu Pro Val Leu Leu
            1010                1015                1020
Ser Phe Phe Gly Pro Tyr Pro Glu Val Ser Pro Ala Asn Gly Leu Asn
1025                1030                1035                1040
Arg Leu Pro Thr Pro Ser Pro Glu Pro Pro Ser Val Val Arg Phe
            1045                1050                1055
Ala Met Pro Pro Gly His Thr His Ser Gly Ser Asp Ser Ser Asp Ser
            1060                1065                1070
Glu Tyr Ser Ser Gln Thr Thr Val Ser Gly Leu Ser Glu Glu Leu Arg
            1075                1080                1085
His Tyr Glu Ala Gln Gln Gly Ala Gly Gly Pro Ala His Gln Val Ile
            1090                1095                1100
Val Glu Ala Thr Glu Asn Pro Val Phe Ala His Ser Thr Val Val His
1105                1110                1115                1120
Pro Glu Ser Arg His His Pro Ser Asn Pro Lys Gln Gln Pro His
            1125                1130                1135
Leu Asp Ser Gly Ser Leu Pro Pro Gly Arg Gln Gly Gln Gln Pro Arg
            1140                1145                1150
Arg Asp Pro Pro Arg Lys Gly Leu Trp Pro Pro Leu Tyr Arg Pro Arg
            1155                1160                1165
Arg Asp Ala Phe Glu Ile Ser Thr Glu Gly His Ser Gly Pro Ser Asn
            1170                1175                1180
Arg Ala Arg Trp Gly Pro Arg Gly Ala Arg Ser His Asn Pro Arg Asn
1185                1190                1195                1200
Pro Thr Ser Thr Ala Met Gly Ser Ser Val Pro Gly Tyr Cys Gln Pro
            1205                1210                1215
Ile Thr Thr Val Thr Ala Ser Ala Ser Val Thr Val Ala Val His Pro
            1220                1225                1230
Pro Pro Val Pro Gly Pro Gly Arg Asn Pro Arg Gly Leu Cys Pro
            1235                1240                1245
Gly Tyr Pro Glu Thr Asp His Gly Leu Phe Glu Asp Pro His Val Pro
            1250                1255                1260
Phe His Val Arg Cys Glu Arg Arg Asp Ser Lys Val Glu Val Ile Glu
1265                1270                1275                1280
Leu Gln Asp Val Glu Cys Glu Glu Arg Pro Arg Gly Ser Ser Ser Asn
            1285                1290                1295
```

(2) INFORMATION FOR SEQ ID NO:61:

(i) SEQUENCE CHARACTERISTICS:
        (A) LENGTH: 20 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:61:

ACATGTACAA CAGGCAGTGG                                                    20

(2) INFORMATION FOR SEQ ID NO:62:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:62:

GCAAGGAGGT TTACCTAGG                                                     19

(2) INFORMATION FOR SEQ ID NO:63:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:63:

TGCCAAGGCT GTGGGCAAGG                                                    20

(2) INFORMATION FOR SEQ ID NO:64:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:64:

GCTTCACCAC CTTCTTGATG                                                    20

(2) INFORMATION FOR SEQ ID NO:65:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:65:

GCTGTGACAA AGTCACATGG                                                    20

(2) INFORMATION FOR SEQ ID NO:66:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:66:

GATGCTGCTT ACATGTCTCG                    20

(2) INFORMATION FOR SEQ ID NO:67:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:67:

Ile Arg His Val Thr Leu Thr Val Pro Ala Tyr Gly Ala Ala Asp His
1               5                   10                  15

Pro Arg Arg Gly Pro Trp Asn Cys Leu Ile Glu Thr Gly Leu
            20                  25                  30

(2) INFORMATION FOR SEQ ID NO:68:

(i) SEQUENCE CHARACTERISTICS:
        (A) LENGTH: 81 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

Val Arg Ala Ala Leu Arg Arg Lys Leu Pro Ala Ala Gln Arg Ala Gly
1               5                   10                  15

Val Phe Thr Leu Ser Val Pro Phe Val Lys Thr Glu Glu Glu Glu Lys
                20                  25                  30

Lys Lys Lys Lys Thr Glu Glu Lys Lys Lys Thr Thr Gly Glu Thr Lys
            35                  40                  45

Arg Pro Ala Ala Thr Arg Gln Gly Gly Asp Glu Gly Arg Leu Gly Glu
        50                  55                  60

Asp Gly Gly Ala Glu Asp Glu Glu Arg Gly Ala Arg Glu Lys Lys Leu
65                  70                  75                  80

Met (2) INFORMATION FOR SEQ ID NO:69:

(i) SEQUENCE CHARACTERISTICS:
        (A) LENGTH: 84 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:69:

Asn Pro Ser Pro Arg Ser Glu Gln Gly Leu Thr Ala Gly Tyr Gly Xaa
1               5                   10                  15

Cys Ser Gln Arg Gly Xaa Arg Arg His Leu Ala Ser Arg Ala Xaa
            20                  25                  30

Leu Leu Gly Arg Arg Gly Asp Xaa Gly Thr Arg Asp Ala Pro Xaa Gly
            35                  40                  45

Gly Arg Xaa Ser Xaa Pro Arg Ser Pro Gly Xaa Arg Gly Gly Pro Arg
        50                  55                  60

```
Ala Xaa Ala Val Asp Pro Gly Gly Leu Arg Arg Leu Gly Ser Gly Xaa
 65          70                  75                  80

Leu Val Xaa Leu
```

(2) INFORMATION FOR SEQ ID NO:70:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:70:

```
Gly Ser Val Thr
 1
```

(2) INFORMATION FOR SEQ ID NO:71:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

```
Gln Phe Leu Leu Met Ala Arg Gln Thr Thr His Ala Glu Gly His Gly
 1               5                  10                  15

Thr Ala
```

(2) INFORMATION FOR SEQ ID NO:72:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:72:

```
Lys Gln Ala Cys Asn Cys Glu Ser Ala Leu His Ser Ala Glu Ser Phe
 1               5                  10                  15

Arg Arg Pro Ser Ala Pro Gly Phe Leu His Phe Pro Phe Leu Leu
                 20                  25                  30
```

(2) INFORMATION FOR SEQ ID NO:73:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:73:

```
Arg Arg Arg Arg Arg Arg Arg Arg Arg Lys Arg Arg Arg Lys
 1               5                  10                  15

Arg Arg Gln Gly Arg Glu Arg Arg Thr Arg Lys Gly Gly Pro Gly Lys
                 20                  25                  30

Lys Asn
```

(2) INFORMATION FOR SEQ ID NO:74:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:74:

```
Cys Glu Ile Gln Ala Arg Ala Pro Ser Arg Gly
1               5                   10
```

(2) INFORMATION FOR SEQ ID NO:75:

(i) SEQUENCE CHARACTERISTICS:
        (A) LENGTH: 74 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:75:

```
Arg Pro Ala Met Val Ser Ala Ala Ser Ala Ala Ala Ala Asp Ala Thr
1               5                   10                  15

Ser Pro Leu Ala Pro Cys Ser Ser Gly Gly Ala Gly Thr Leu Gly Xaa
                20                  25                  30

Gly Thr Pro Xaa Xaa Ala Asp Gly Xaa Ala Ser Pro Asp Arg Arg Ala
            35                  40                  45

Gly Gly Ala Gly Xaa Ala Pro Gly Pro Trp Ile Arg Val Gly Cys Ala
50                  55                  60

Ala Trp Ala Xaa Xaa Xaa Trp Ser Arg Ser
65                  70
```

(2) INFORMATION FOR SEQ ID NO:76:

(i) SEQUENCE CHARACTERISTICS:
        (A) LENGTH: 180 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:76:

```
Asp Pro Ser Arg Asp Pro Asp Ser Ser Cys Leu Trp Arg Gly Arg Pro
1               5                   10                  15

Pro Thr Pro Arg Ala Met Glu Leu Leu Asn Arg Asn Arg Leu Val Ile
                20                  25                  30

Val Ser Pro Arg Cys Thr Pro Pro Lys Ala Ser Gly Gly Pro Ala Arg
            35                  40                  45

Arg Gly Phe Tyr Thr Phe Arg Ser Phe Cys Lys Asp Gly Gly Gly Gly
        50                  55                  60

Glu Glu Glu Glu Glu Asn Gly Gly Glu Glu Lys Asp Arg Gly Asp
65                  70                  75                  80

Ser Gly Gly Arg Gly Lys Gly Gly Gln Gly Lys Lys Ile Asp Val Lys
                85                  90                  95

Ser Lys Pro Ala Leu Arg Ala Gly Val Asp Gly Arg Leu Trp Xaa Val
            100                 105                 110

Gln Pro Ala Arg Xaa Pro Pro Thr Pro Arg Leu Ser Arg Xaa Ala
```

```
                115                 120                 125
Pro Arg Ala Ala Arg Gly Xaa Trp Asp Xaa Gly Arg Pro Xaa Arg Arg
    130                 135                 140

Thr Xaa Glu Xaa Ala Pro Ile Ala Gly Xaa Glu Gly Arg Ala Xaa Arg
145                 150                 155                 160

Xaa Gly Arg Gly Ser Gly Trp Ala Ala Pro Pro Gly Leu Xaa Xaa Xaa
                165                 170                 175

Gly Xaa Ala Pro
        180
```

(2) INFORMATION FOR SEQ ID NO:77:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

TGTTTTAGT    9

(2) INFORMATION FOR SEQ ID NO:78:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

TGTTCCAGT    9

(2) INFORMATION FOR SEQ ID NO:79:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:79:

CTAAACAGAG ATGG    14

(2) INFORMATION FOR SEQ ID NO:80:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:80:

CTAAACAGCG TCTGGTGGAT GCAGATGG    28

(2) INFORMATION FOR SEQ ID NO:81:

(i) SEQUENCE CHARACTERISTICS:
        (A) LENGTH: 18 base pairs

-continued

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:81:

AATCCGCCGA TCCAGACT                                                18

(2) INFORMATION FOR SEQ ID NO:82:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:82:

AGGGTGCCTG CCGTGG                                                  16

(2) INFORMATION FOR SEQ ID NO:83:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

CAGGACTGTG CTCATTG                                                 17

(2) INFORMATION FOR SEQ ID NO:84:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..85
        (D) OTHER INFORMATION: /note= "exon 2a"

(xi) SEQUENCE DESCRIPTION: SEQ ID NO:84:

GGAGGACGAG GAAAGGGGGG CCAGGGAAAA AAATTGATGT GAAATCCAAG CCCGCGCTCC   60

GAGCAGGGGT TGACGGCCGG CTATG                                        85
```